US009605250B2

(12) United States Patent
Appaiah et al.

(10) Patent No.: US 9,605,250 B2
(45) Date of Patent: Mar. 28, 2017

(54) CHIMERIC ANTIBACTERIAL POLYPEPTIDES

(75) Inventors: Chemira B. Appaiah, Bangalaore (IN); Sriram Padmanabhan, Bangalaore (IN); R. Sanjeev Saravanan, Bangalaore (IN); Bharathi Sriram, Bangalaore (IN)

(73) Assignee: Gangagen, Inc., Newark, CA (US)

(*) Notice: Subject to any disclaimer, the term of this patent is extended or adjusted under 35 U.S.C. 154(b) by 30 days.

(21) Appl. No.: 14/111,531

(22) PCT Filed: Apr. 12, 2012

(86) PCT No.: PCT/IN2012/000261

§ 371 (c)(1), (2), (4) Date: Oct. 11, 2013

(87) PCT Pub. No.: WO2012/140676

PCT Pub. Date: Oct. 18, 2012

(65) Prior Publication Data

US 2014/0050713 A1 Feb. 20, 2014

(30) Foreign Application Priority Data

Apr. 12, 2011 (IN) ........................... 1277/CHE/2011

(51) Int. Cl.

| | |
|---|---|
| ***A61K 38/43*** | (2006.01) |
| ***C12N 9/24*** | (2006.01) |
| ***C12N 9/36*** | (2006.01) |
| ***C12N 1/06*** | (2006.01) |
| ***C12N 15/62*** | (2006.01) |
| ***C07K 14/47*** | (2006.01) |
| ***C12N 9/48*** | (2006.01) |
| ***C07K 14/005*** | (2006.01) |
| *A61K 38/00* | (2006.01) |

(52) U.S. Cl.

CPC .......... *C12N 9/2462* (2013.01); *C07K 14/005* (2013.01); *C07K 14/47* (2013.01); *C07K 14/4742* (2013.01); *C12N 1/06* (2013.01); *C12N 9/24* (2013.01); *C12N 9/48* (2013.01); *C12N 15/62* (2013.01); *A61K 38/00* (2013.01); *C07K 2319/03* (2013.01); *C12N 2795/00022* (2013.01); *C12N 2795/00033* (2013.01); *C12N 2795/10122* (2013.01); *C12N 2795/10133* (2013.01); *C12N 2795/10322* (2013.01); *C12N 2795/10333* (2013.01)

(58) Field of Classification Search

CPC .................................. A61K 38/43; C12N 9/24

USPC ......................................................... 530/350

See application file for complete search history.

(56) References Cited

U.S. PATENT DOCUMENTS

2009/0324576 A1* 12/2009 Padmanabhan et al. .. 424/94.63

FOREIGN PATENT DOCUMENTS

| | | | |
|---|---|---|---|
| WO | 97/35009 | A1 | 9/1997 |
| WO | 2007/130655 | A2 | 11/2007 |
| WO | 2008/001342 | A1 | 1/2008 |
| WO | 2010/149792 | A2 | 12/2010 |

OTHER PUBLICATIONS

Extended European Search Report dated Dec. 10, 2014 for EP Application No. 12770916.0, 5 pages.
Chinese Office Action dated Jan. 30, 2015 for Chinese Patent Application No. 201280026193.7, 14 pages, with English translation.
Briers et al., "Muralytic activity and modular structure of endolysins of *Pseudomonas aeruginosa* bacteriophages ϕKZ and EL", *Molecular Microbiology*, vol. 65, No. 5, pp. 1334-1344 (2007).
Office Action in MX/a/2013/011853 mailed Feb. 21, 2016, 7 pages.
Xu et al., "A Single-Arrest Sequence Mediates Export and Control of the Phage P1 Endolysin," PNAS, Apr. 27, 2004, vol. 101, No. 17, pp. 6415-6420.
Office Action dated Feb. 24, 2016 in JP 2014-504452.
Structural Protein Containing C-Terminal Lysozyme Domain [Pseudomonas phage phiKMV], NP_877475, GenPept [online], Apr. 17, 2009 uploaded [retrieved on Feb. 8, 2016], URL, http://www.ncbi.nlm.nih.gov/protein/NP_877475.
Examination Report in EP 12 770 916.0 mailed Aug. 31, 2016.
Cserzo, et al., "Prediction of Transmembrane α-helices in Prokaryotic Membrane Proteins: The Dense Alignment Surface Method," *Protein Engineering*, vol. 10, No. 6, pp. 673-676 (1997).

* cited by examiner

*Primary Examiner* — Maryam Monshipouri

(74) *Attorney, Agent, or Firm* — Kilpatrick Townsend & Stockton LLP

(57) ABSTRACT

Provided herein are antibacterial compositions and methods of making and using the compositions.

8 Claims, 4 Drawing Sheets

A.

B.

A.

B.

A.

B.

C.

CHIMERIC ANTIBACTERIAL POLYPEPTIDES

FIELD OF INVENTION

The present invention provides methods and compositions to reduce growth of microbial colonies, including infections, and includes therapeutic compositions, methods for treatment of infections, and methods for identifying additional such compositions.

BACKGROUND OF THE INVENTION

Bacteria are ubiquitous, ecologically diverse, and find unusual niches for survival. They are present throughout the environment, e.g., soil, dust, water, and on virtually all surfaces.

Pathogenic bacteria can cause infectious diseases in humans, other animals, and plants. Some bacteria can only infect or cause problems for a particular host, while others have a broader host specificity, and can cause trouble in a number of hosts. Diseases caused by bacteria are almost as diverse as the bacteria themselves, e.g., food poisoning, tooth decay, anthrax, general infectious diseases, and even certain forms of cancer.

Certain bacteria are normally innocuous, but become pathogenic at the appropriate opportunity, or become problematic upon introduction to an abnormal site or situation. Persons lacking effective immune systems are most vulnerable, and certain bacteria use weakened hosts to proliferate and disperse throughout the population.

Antibiotics have revolutionized clinical medicine over the last half century. Since the original discovery of antibiotic phenomenon, the mechanism of action and development of this class of remarkable therapeutic entities has made enormous progress. See, e.g., Therrien and Levesque (2000) *FEMS Microbiol Rev.* 24:251-62; Durgess (1999) *Chest* 115(3 Suppl):19S-23S; Medeiros (1997) *Clin. Infect. Dis.* 24(Suppl 1):S19-45; Jones (1996) *Am. J. Med.* 100(6A):3S-12S; Ford and Hait (1993) *Cytotechnology* 12(1-3):171-212; and Liu (1992) *Compr Ther.* 18:35-42. Antibiotics had about $32 B worldwide sales in 2002.

Yet the widespread appearance of antibiotic-resistant bacteria has emphasized the vulnerability of current antimicrobial treatments to bacterial adaptation. See, e.g., Walsh (1992) *Antibiotics: Actions, Origins, Resistance Amer. Soc. Microbiol.*; Cunha (1992) *Antibiotic Essentials* (Physicians Press); Amyes (2003) *Magic Bullets, Lost Horizons: The Rise and Fall of Antibiotics* (Taylor & Francis); Axelsen (2001) *Essentials of Antimicrobial Pharmacology: A Guide to Fundamentals for Practice* (Humana Press); and Mainous and Pomeroy (eds. 2001) *Management of Antimicrobials in Infectious Diseases: Impact of Antibiotic Resistance* (Humana Press). Multiple resistance plasmid NDM-1 has been reported (Kumarasamy et al. (2010) *Lancet Infectious Diseases* 10:597-602; and Walsh et al. (2011) *Lancet Infectious Diseases*, Early Online Publication, 7 Apr. 2011, doi:10.1016/S1473-3099(11)70059-7).

Thus, improved methods for decreasing bacterial growth and survival, or limiting bacterial pathogenicity, find great utility, especially for antibiotic resistant bacteria, which are most commonly Gram-negative. Antimicrobial effects are applicable to environmental, local, topical, and particularly in vivo colonization. The present invention addresses these and other significant issues.

BRIEF SUMMARY OF THE INVENTION

Provided herein are antibacterial chimeric polypeptides comprising a component for traversing the outer membrane of a Gram negative bacteria (i.e., a membrane traversing domain, or MTD) and a component for degrading the bacterial cell wall (i.e., a muralytic domain, or MD).

Provided are chimeric polypeptides comprising an MD derived from one of the MD sources listed in Table A and an MTD derived from one of the MTD sources listed in Table B. In some embodiments, the chimeric polypeptide reduces CFU of a culture of Gram negative bacteria compared to an untreated control culture. In some embodiments, 1-100 nmol of the chimeric polypeptide lyses at least 50% of $10^7$ Gram negative bacteria in a CFU drop assay. In some embodiments, the bacteria are selected from the group consisting of *Pseudomonas aeruginosa, Klebsiella pneumoniae, Escherichia coli, Klebsiella pneumoniae, Acinetobacter baumanii, Salmonella typhimurium, Salmonella infantis, Shigella, Proteus mirabilis*, and *Burkholderia thailandensis*.

In some embodiments, the MTD comprises a sequence selected from the group consisting of: amino acids 16-39 of SEQ ID NO:4; amino acids 242-264 of SEQ ID NO:15; amino acids 242-271 of SEQ ID NO:17; amino acids 220-406 of SEQ ID NO:19; amino acids 220-400 of SEQ ID NO:21; amino acids 220-885 of SEQ ID NO:23; and variants thereof with a DAS profile between 1.2-2.6. In some embodiments, the variant thereof has 1-6 hydrophobic amino acids substituted with amino acids with a hydropathy score of −2 or lower. In some embodiments, the DAS profile of the MTD is under 2.5. In some embodiments, the DAS profile of the chimeric polypeptide is under 2.5. In some embodiments, the MTD comprises a sequence selected from the group consisting of: amino acids 16-39 of SEQ ID NO:4; amino acids 242-264 of SEQ ID NO:15; amino acids 242-271 of SEQ ID NO:17; amino acids 220-406 of SEQ ID NO:19; amino acids 220-400 of SEQ ID NO:21; amino acids 220-885 of SEQ ID NO:23; and variants thereof with at least 80% (e.g., at least 85, 87, 90, 92, 95, 98, or 99%) identity to a sequence selected from the group consisting of: amino acids 16-39 of SEQ ID NO:4; amino acids 242-264 of SEQ ID NO:15; amino acids 242-271 of SEQ ID NO:17; amino acids 220-406 of SEQ ID NO:19; amino acids 220-400 of SEQ ID NO:21; amino acids 220-885 of SEQ ID NO:23.

In some embodiments, the chimeric polypeptide comprises a sequence selected from the group consisting of: SEQ ID NOs:9, 11, 13, 15, 17, 19, 21, and 23, and variants thereof having at least 90% (e.g., at least 92, 93, 94, 95, 96, 97, 98, or 99%) identity to SEQ ID NO:9, 11, 13, 15, 17, 19, 21, or 23. In some embodiments, the variant thereof has 1-10 of the cysteine or methionine amino acids substituted with non-cysteine, non-methionine amino acids.

In some embodiments, the chimeric polypeptide comprises an MD comprising a sequence of amino acids 737-875 of SEQ ID NO:2, or a variant thereof capable of lysing chloroform treated Gram negative bacteria. In some embodiments, the variant thereof has at least 90% (e.g., at least 92, 93, 94, 95, 96, 97, 98, or 99%) identity to amino acids 737-875 of SEQ ID NO:2. In some embodiments, the MD comprises a sequence of amino acids 683-889 or SEQ ID NO:2 or a variant thereof having at least 90% (e.g., at least 92, 93, 94, 95, 96, 97, 98, or 99%) identity to amino acids 683-889 of SEQ ID NO:2. In some embodiments, 1-100 nmol of the MD lyses at least 50% of $10^7$ chloroform-treated *Pseudomonas aeruginosa* bacteria in a CFU drop assay. In some embodiments, the variant thereof has 1-7 of the methionine amino acids substituted with non-methionine amino acids.

In some embodiments, the chimeric polypeptide comprises an MD comprising a sequence at least 90% identical to amino acids 737-875 of SEQ ID NO:2 and an MTD comprising a sequence at least 80% identical to amino acids 16-39 of SEQ ID NO:4. In some embodiments, the chimeric polypeptide comprises a sequence having at least 95% (e.g., 96, 97, 98, 99, or 100%) identity to SEQ ID NO:11 or 13.

In some embodiments, the MTD and MD are joined by a linker comprising 3-5 positively charged amino acids (e.g., R, H, K, and combinations thereof). In some embodiments, the positively charged amino acids are consecutive or in close proximity (e.g., with 1-3 intervening non-positive amino acids). In some embodiments, the MD is flanked on the N- and C-terminal ends with 3-5 positively charged amino acids. In some embodiments, the chimeric polypeptide is attached to a PAG or PEG molecule.

Further provided are antibacterial compositions comprising a chimeric polypeptide as described above. In some embodiments, the antibacterial composition comprises the chimeric polypeptide an agent that reduces oxidation. In some embodiments, the antibacterial composition is a pharmaceutical composition comprising the chimeric polypeptide and a pharmaceutically acceptable excipient.

Further provided are methods of treating a bacterial infection in an individual, e.g., inhibiting bacterial cell growth and/or reducing the number of target bacteria in the individual. In some embodiments, the method comprises administering a pharmaceutical composition comprising the chimeric polypeptide to the individual in an amount effective to inhibit cell growth of the target bacteria in the individual, e.g., compared to an untreated control. In some embodiments, the method comprises administering a pharmaceutical composition comprising the chimeric polypeptide to the individual in an amount effective to reduce the number of target bacteria in the individual compared to the number of target bacteria present prior to treatment. In some embodiments, the target bacteria (the bacteria infecting the individual) are selected from the group consisting of *Pseudomonas aeruginosa, Klebsiella pneumoniae, Escherichia coli, Klebsiella pneumoniae, Acinetobacter baumanii, Salmonella typhimurium, Salmonella infantis, Shigella, Proteus mirabilis*, and *Burkholderia thailandensis*.

Further provided are methods of reducing the number of target bacteria or inhibiting bacterial cell growth in an environment comprising applying a chimeric as described herein to the environment. In some embodiments, the target bacteria bacteria are selected from the group consisting of *Pseudomonas aeruginosa, Klebsiella pneumoniae, Escherichia coli, Klebsiella pneumoniae, Acinetobacter baumanii, Salmonella typhimurium, Salmonella infantis, Shigella, Proteus mirabilis*, and *Burkholderia thailandensis*. In some embodiments, the environment is a surface (e.g., for food preparation or medical use), a pharmaceutical composition, a medical device, a water or liquid source, or a food product.

The present invention is based in part upon the recognition that phage-encoded cell wall degrading activities, e.g., murein-degrading (or muralytic) enzymes, which are the core of the phage lysis functions, are also found as structural components of the phage virion where they can be required for infection of the bacteria. Gram-negative bacteria are characterized by a thin peptidoglycan cell wall surrounded by an outer membrane, which is lacking in Gram-positive bacteria. While a muralytic enzyme can digest the thin peptidoglycan layer of a Gram-negative cell, the outer membrane typically prevents access of the muralytic activity from the outside medium. Linking an enzymatically active muralytic segment (fragment) to an agent (entity) that provides for transfer of the segment across the outer membrane allows the enzymatic activity to contact the peptidoglycan layer, leading to degradation of the peptidoglycan layer. The failure of the peptidoglycan layer causes the cell to rupture due to the enormous osmotic pressure across the inner cell membrane.

The invention provides a recombinant chimeric polypeptide comprising:

a) a segment comprising at least 20 amino acid matches to amino acids 16-39 of BPI TMD; and b) a plurality of distinct segments of a least 20 amino acids exhibiting at least 85% identity to amino acids 683-898 of GP36, which segments do not overlap.

In some embodiments, the segment of at least 20 amino acid matches is at least 22, 23, or 24 matches. In some embodiments, the plurality numbers at least three. In some embodiments, the distinct segments include one of at least 40 amino acids exhibiting at least 92% identity. In some embodiments, the chimeric polypeptide exhibits at least 25, 30, 35, 40, 50, 55, 60, 75, 80, 85, 90, 95% or higher % muralytic activity on purified peptidoglycan from a Gram-negative bacterial host as compared to GP36. In some embodiments, the chimeric polypeptide exhibits at least 25, 30, 35, 40, 50, 55, 60, 75, 80, 85, 90, 95% or higher % muralytic activity on an intact Gram-negative bacterial host as compared to the polypeptide of SEQ ID NO:9. In some embodiments, the polypeptide exhibits at least 85, 90, 92, 95, 96, 97, 98, 99, or 100% sequence identity to the polypeptide of SEQ ID NO: 9. In some embodiments, the chimeric polypeptide comprises at least amino acids 16-39 of BPI TMD. In some embodiments, the chimeric polypeptide comprises a sequence with at least 85, 90, 92, 95, 96, 97, 98, 99, or 100% identity to amino acids 683-889 or 737-875 of GP36. In some embodiments, the chimeric polypeptide comprises or consists of SEQ ID NO: 9.

In some embodiments, the chimeric polypeptide is substantially free of other phage proteins; or is substantially free of other proteinaceous materials. In some embodiments, the chimeric polypeptide is combined with another antimicrobial agent, including an antibiotic or depolymerase agent. In some embodiments, the chimeric polypeptide is admixed with a pharmaceutical excipient or is in a buffered or sterile composition.

In some; exhibits a bacterial cell wall degrading activity selected from muralytic, glucosamidase, muraminidase, amidase, or endopeptidase activity. In some embodiments, the cell wall degrading (e.g., muralytic) activity is effective on multiple Gram-negative bacteria strains. In some embodiments, the cell wall degrading (e.g., muralytic) activity is effective on a *Pseudomonas, Burkholderia*, or *Escherichia* bacteria strain. In some embodiments, the cell wall degrading (e.g., muralytic) activity is effective on one or more strains described as a *Klebsiella, Acinetobacter, Salmonella, Proteus, Neisseria, Moraxella, Hemophilus, Enterobacter, Serratia, Legionella*, or *Helicobacter* species.

The invention provides an expression vector comprising an isolated or recombinant nucleic acid encoding the chimeric polypeptides described herein. In some embodiments, the invention provides a recombinant cell comprising the expression vector. In some embodiments, the cell is a eukaryote or prokaryote cell, e.g., to express the nucleic acid to produce or secrete the protein.

Methods are provided, e.g., of enzymatically degrading the cell wall of a bacteria by exposing the bacteria to the chimeric polypeptide described herein. In some embodiments, the method results in at least a 50, 60, 70, 80 or 90% decrease in a sensitive bacterial population on a surface (e.g., hospital, work, or furniture, etc.). In some embodiments, the method comprises introducing the chimeric polypeptide into an animal (e.g., human or other mammal), and results in at least a 20% decrease in the population of sensitive bacteria in a selected location in or on the animal. In some embodiments, the chimeric polypeptide is contacted with (applied to) an animal surface or compartment (e.g., digestive tract). In some embodiments, the chimeric polypeptide is applied to (administered to) an individual to treat a bacterial infection of the skin, mucosal tissue, blood, urinary tract, respiratory tract, or gastrointestinal tract. In some embodiments, the method comprises using the chimeric polypeptide in order to inoculate (induce an immune response in) an individual with dead or lysed bacteria (see, e.g., WO2003/026690).

The invention also provides a chimeric polypeptide comprising: a muralytic domain comprising at least two non-overlapping segments of at least 15 contiguous amino acids from amino acids 683-898 of SEQ ID NO: 2, and an outer membrane translocation domain comprising amino acids 16-39 of SEQ ID NO: 4, wherein the muralytic domain has cell wall degrading activity against a target bacterium. In some embodiments, the muralytic domain comprises a plurality of non-overlapping segments of at least 15 contiguous amino acids from a virion associated muralytic activity of a lytic phage. In some embodiments, the muralytic domain comprises a plurality of non-overlapping segments of at least 15 contiguous amino acids encoded by a prophage structural gene. In some embodiments, the muralytic domain is from a myoviridae or podoviridae phage. In some embodiments, the muralytic domain is derived from the muralytic domain used by the phage to infect a host cell In some embodiments, the target bacterium is a Gram-negative bacterium (has a bacterial outer membrane. In some embodiments, the target bacterium is a *Pseudomonas, Escherichia, Burkholderia, Klebsiella, Acinetobacter, Salmonella, Proteus, Neisseria, Moraxella, Hemophilus, Enterobacter, Serratia, Legionella*, or *Helicobacter* species. In some embodiments, the target bacterium is resistant to one or more common therapeutically used antimicrobial agent (e.g., antibiotic resistant).

In some embodiments, the invention provides methods for treating a bacterial infection in a subject in need of treatment (e.g. an individual having a bacterial infection, or at risk of developing an infection) comprising: administering a chimeric polypeptide as described herein to the subject, thereby treating the bacterial infection (e.g., reducing the number of target bacteria in the individual). The subject can be a medical or veterinary patient including a human, a primate, a show animal, or a companion animal. In some embodiments, the method results in a decrease CFU of a target Gram-negative bacterial population of at least 20, 25, 30, 50, 60, 70, 80 or higher % in the individual, or at least 50, 60, 70, 80, 85, 90, 95, or higher % in culture (or in an in vitro application, e.g., on a surface). The invention further provides methods of disinfecting a surface or liquid by contacting the surface or liquid with the chimeric polypeptide (or a composition thereof).

In some embodiments, the invention provides methods for producing the chimeric polypeptide comprising expressing a nucleic acid encoding the chimeric polypeptide, e.g., in a eukaryotic cell. In some embodiments, the nucleic acid is in an expression vector such as a plasmid.

In some embodiments, the invention provides a recombinant muralytic protein comprising amino acids 16-39 of BPI TMD linked to a muralytic domain, wherein the protein has bacterial outer membrane traversing capacity (activity) and peptidoglycan degrading activity. In some embodiments, the muralytic protein has a peptidoglycan degrading activity of 50, 55, 60, 75, 80, 85, 90, 95% or higher % on purified peptidoglycan from a Gram-negative bacterium as compared to GP36. In some embodiments the amino acids 16-39 of BPI TMD and the muralytic domain are linked using a non-peptide bond. In some embodiments, the muralytic protein is a chimeric protein. Further provided are a recombinant nucleic acid that encodes the muralytic protein, and a host cell comprising the nucleic acid. In some embodiments, the invention provides methods for killing a bacterium possessing an outer membrane, comprising contacting the bacterium with the muralytic protein.

In some embodiments, the invention provides a recombinant muralytic protein comprising amino acids 737-875 of GP36 (or amino acids 683-889 of GP36) linked to a membrane transfer domain, wherein the protein has bacterial outer membrane traversing capacity and peptidoglycan degrading activity. In some embodiments, the muralytic protein has bacterial outer membrane traversing activity of 50, 55, 60, 75, 80, 85, 90, 95% or higher % as compared to BPI-TMD. In some embodiments the amino acids 16-39 of BPI TMD and the muralytic domain are linked using a non-peptide bond. In some embodiments, the muralytic protein is a chimeric protein. Further provided are a recombinant nucleic acid that encodes the muralytic protein, and a host cell comprising the nucleic acid. In some embodiments, the invention provides methods for killing a bacterium possessing an outer membrane comprising contacting the bacterium with the muralytic protein.

In some embodiments, the invention provides an isolated recombinant muralytic protein comprising a muralytic domain (providing peptidoglycan degrading activity) linked to a membrane transfer domain (providing bacterial outer membrane traversing capacity). Further provided is a recombinant nucleic acid encoding the muralytic protein and a host cell comprising the nucleic acid. The invention further provides methods for killing a bacterium possessing an outer membrane by contacting the bacterium with the muralytic protein.

In some embodiments, the invention provides an antibody specific for the new combination of a muralytic domain and a membrane transfer domain, e.g., that recognizes an epitope unique to the combined polypeptide. In some embodiments, the antibody is specific for the polypeptide of SEQ ID NO:9, and polypeptides having at least 85, 90, 92, 95, or higher % identity to SEQ ID NO:9, but does not significantly bind to a polypeptide of SEQ ID NO:4 or a polypeptide of SEQ ID NO:5. In some embodiments, the invention provides methods to detect or isolate a chimeric polypeptide as described herein comprising contacting the antibody with a liquid or surface comprising the chimeric polypeptide.

DETAILED DESCRIPTION OF THE INVENTION

I. Introduction

Figure 1:
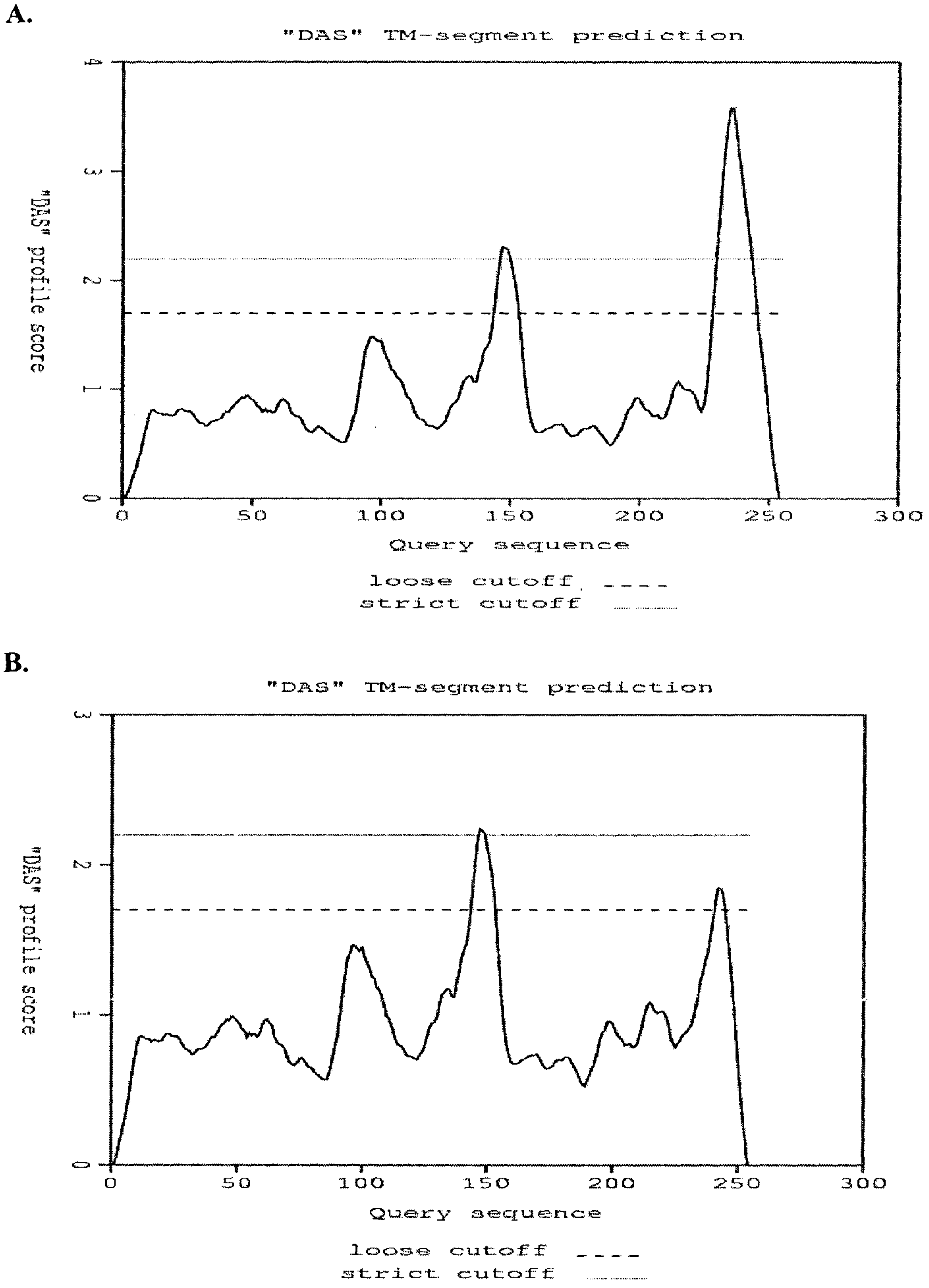
FIG. 1 shows the DAS hydrophobicity plots of (A) P266 and (B) P275. Relative hydrophobicity is shown along the length of the protein, with the N terminus on the left and C terminus on the right. Note the C terminal spike for P266 that is reduced in the modified P275 protein.

The peptidoglycan (murein) sacculus is an essential structural component of the cell wall of most bacteria. Made of glycan strands cross-linked by short peptides, the sacculus forms a closed, bag-shaped structure surrounding the bacteria cytoplasmic membrane. The sacculus must withstand up to 25 atmospheres of osmotic pressure. The sacculus is flexible, allowing reversible expansion under pressure, which allows diffusion of even large protein molecules. See, e.g., Silhavy et al. (2010) *CSH Persp. Biol.,* 2:a000414; Vollmer et al. (2008) *FEMS Microbio. Revs* 32:149-167; Bos et al. (2007) *Ann. Rev. Microbiol.* 61:191-214; and Costerton et al. (1974) Bact. Revs. 38:87-110.

Many antibiotics act on the peptidoglycan layer of a target bacteria species. This structure is thus a critical component in the survival of a bacterial target. Attack of the peptidoglycan is a rational strategy for killing target bacterial hosts. Although the peptidoglycan layer is typically about 1-3 layers thick, the outer membrane serves as a permeability barrier that prevents externally applied muralytic enzymes from reaching their substrate.

The present invention links the muralytic function to a membrane permeability function to achieve a new entity. The chimeric (and linked) constructs described herein combine a peptidoglycan degrading enzyme activity with a membrane traversing function. In some embodiments, the traversing function is achieved with a protein segment which allows the protein with muralytic activity to be transferred across the bacterial outer membrane. In some embodiments, the traversing segment itself mediates a membrane transfer event, thereby moving the muralytic activity from outside of the bacterial outer membrane to the inside, and allowing contact between the enzyme and its peptidoglycan substrate. In some embodiments, the traversing segment takes advantage of an endogenous translocation system in the outer membrane by presenting earmark motifs which signal the system to import the molecule into the periplasmic space. In some embodiments, the traversing segment directs the muralytic polypeptide to the outer leaflet of the outer membrane, and the muralytic polypeptide flips from the outer leaflet of the outer membrane to the inner leaflet, thereby delivering the muralytic segment to the peptidoglycan substrate.

II. Murein-Degrading Enzymes; Lysozymes and Lysins

Muralytic domains (also called catalytic domains herein) include, e.g., lysozyme proteins (Salazar and Asenjo (2007) *Biotechnol. Lett.* 29:985-94). Breakdown of the peptidoglycan structure occurs naturally in at least four contexts. One is biosynthesis of the structure itself; as the bacterial cell grows and divides, it must necessarily must break down the structure. See, e.g., Vollmer (2008) *FEMS Microbiol Rev.* 32:287-306; Scheurwater, et al. (2008) *Int. J. Biochem. Cell Biol.* 40:586-91; Keep, et al. (2006) *Trends Microbiol.* 14:271-276, and Baba and Schneewind (1998) *EMBO J.* 17:4639-4646. There are additional situations when the cell itself must rearrange or modify structure which was synthesized earlier. These activities can be derived from the bacteria themselves. Second, eukaryotic hosts degrade the structure upon clearing of an infection, e.g., using mutanolysin or lysozymes. See, e.g., Callewaert and Michiels (2010) *J. Biosci.* 35:127-60; Harder, et al. (2007) *Endocr. Metab. Immune Disord Drug Targets* 7:75-82; and Lichtman, et al. (1992) *J. Clin. Invest.* 90:1313-1322. These activities will typically be derived from eukaryote hosts in or on which the bacteria live or can colonize. A third area is in phage replication, where the phage typically employs an endolysin to release the replicated phages and lyse the bacterial host cell. See, e.g., Srividhya and Krishnaswamy (2007) *J. Biosci.* 32:979-90; and Loessner (2005) *Curr. Opin. Microbiol.* 8:480-487. These activities will typically be found in the bacteriophage genome. This is a lysis of the peptidoglycan layer of cells from within. A fourth context is where phage infection requires that the peptidoglycan barrier be traversed, as described in Padmanabhan, et al. WO2007/130655. This is degradation of the peptidoglycan layer from the exterior of the cell. These activities will be found as a component of the phage virion, and will typically be encoded in the phage genome.

Each of these mechanisms involve some means to disassemble the peptidoglycan structure. Thus, muralytic activities are found in genomes of eukaryotic hosts for bacteria, in bacteria genomes themselves, and in phage (and related prophages) which target bacteria as hosts. Muralytic domains can be found by homology to any of these sources, and informatics can be used to identify candidates genes with their respective canonical motifs.

Peptidoglycan "degrading activities" can be converted into highly effective bacteriocidal activities for use against Gram-negative bacterial pathogens under therapeutic conditions, and can include muraminidase, glucosaminidase, amidase, or endopeptidase activities. Exemplary muralytic domains can be identified, incorporated into chimeric constructs to be delivered to the peptidoglycan substrate, produced, purified, and confirmed to have bactericidal activity against bacterial hosts with an outer membrane. Recombinant constructs comprising such activities have significant advantageous properties as antimicrobial compositions and formulations. Many of the peptidoglycan degrading activities of the invention are directed to Gram-negative bacteria, or bacteria which possess an outer membrane, but others will have target specificity which may include either or both Gram-negative and Gram-positive bacteria. The peptidoglycan structures of the two types of bacteria share certain linkages and structures, which may be susceptible to a selected muralytic activity. Thus, muralytic domains which can hyrdrolyze shared linkages may have broader target range than those which do not.

An example of the linked polypeptides of the invention uses a fragment comprising a lysozyme domain from *Pseudomonas* phage P134, which is closely related to phage phiKMV. The ORF36 in phage P134 that corresponds to that in phiKMV lyses Gram-negative bacterial cells whose outer membrane has been removed. Contacting the construct to a variety of different Gram-negative bacteria after the outer membrane was removed resulted in the cells being broken down. These results demonstrate that the peptidoglycans from different Gram-negative bacteria species are susceptible to the muralytic activity.

Sequence homology searches identify various other similar domains which can be used as alternative sources for peptidoglycan degrading activities. The small size of the polypeptides exhibiting these activities affords efficient large scale production. Accessibility to relevant cell wall target components, e.g., peptidoglycans, at the bacterial target is provided, as are pharmacological distribution upon in vivo administration.

Relevant muralytic activities can be found within the lysozyme-like superfamily, lytic transglycosylase (LT), goose egg white lysozyme (GEWL); the Superfamily C100442 containing Lysozyme_like domain, which contains several members including the Soluble Lytic Transglycosylases (SLT), Goose Egg-White Lysozymes (GEWL), Hen Egg-White Lysozymes (HEWL), Chitinases, Bacteriophage lambda lysozymes, Endolysins, Autolysins, Chitosanases. All these members are involved in the hydrolysis of beta-1,4-linked polysaccharides. The Cysteine Histidine dependent Amidohydrolase/Peptidase (CHAP) domain is found in phage endolysins and bacterial autolysins. Most proteins containing a CHAP domain function as peptidoglycan hydrolases and are commonly associated with amidases. See Bateman and Rawlings (2003) *Trends Biochem. Sci.* 5:234-237; and Pritchard, et al. (2004) *Microbiology* 150: 2079-2087. See also the Carbohydrate-Active enZYmes Database found at cazy.org. The CAZY database describes the families of structurally related catalytic and carbohydrate-binding modules (or functional domains) of enzymes that degrade, modify, or create glycosidic bonds. Another source for endopeptidases is the database from the website found at merops.sanger.ac.uk/cgi-bin/clan_index?type=P. Table A provides an exemplary list of enzymes having peptidoglycan degrading activities that can be used in the present invention. Additional similar or analogous activities may be found which are similarly annotated, share characteristic motifs with, or are homologous to members of the list.

TABLE A

| Muralytic Domain (MD) sources | |
|---|---|
| Description | Details |
| Phage lysozyme | Lysozyme helps to release mature phage particles from the cell wall by breaking down the peptidoglycan. The enzyme hydrolyses the 1,4-beta linkages between N-acetyl-D-glucosamine and N-acetylmuramic acid in peptidoglycan heteropolymers of prokaryotic cell walls. |
| C-type lysozyme/alpha-lactalbumin family | C-type lysozymes are secreted bacteriolytic enzymes that cleave the peptidoglycan of bacterial cell walls. Structure is a multi-domain, mixed alpha and beta fold, containing four conserved disulfide bonds. |
| Gene 25-like lysozyme | This family includes the phage protein Gene 25 from T4 which is a structural component of the outer wedge of the baseplate that has acidic lysozyme activity |
| A1 propeptide | Most eukaryotic endopeptidases (Merops Family A1) are synthesised with signal and propeptides. The animal pepsin-like endopeptidase propeptides form a distinct family of propeptides, which contain a conserved motif approximately 30 residues long. |
| Prophage endopeptidase tail | This family is of prophage tail proteins that are probably acting as endopeptidases. (e.g.: prophage tail protein gp18 (NP_465809.1) from Listeria monocytogenes |
| REPROLYSIN (M12B) FAMILY | The members of this family are enzymes that cleave peptides. These |
| ZINC METALLOPROTEASE | proteases require zinc for catalysis. Members of this family are also known as adamalysins. Most members of this family are snake venom endopeptidases, but there are also some mammalian proteins such as P78325 and fertilin. |
| Virion associated muralytic enzymes from phages (VAMEs) | |
| Mutanolysin | Muramidase derived from *Streptomyces globisporus* |
| Peptidoglycan hydrolases eg: Mur-1 N-acetylmuramidase , Mur-2 N-acetylglucosaminidase | From *Enterococcus hirae* ATCC9790 |
| Phage PhiKMV | gp36<br>Protein domain: Lysozyme like superfamily |
| Phage LKD16 | orf3<br>Protein domain: Lysozyme like superfamily |
| Phage LICD19 | gp36<br>Protein domain: Lysozyme like superfamily |
| Phage phikF77 | gp40<br>Protein domain: Lysozyme like superfamily |
| Phage PT2 | gp42<br>Protein domain: Lysozyme like superfamily |
| Phage PT4 | gp40<br>Protein domain: Lysozyme like superfamily |
| Phage 201 | gp276<br>Protein domain: Lytic Transglycosylase (LT) or Goose Egg White Lysozyme (GEWL) |
| Phage F8 | orf38<br>Protein domain: Lytic Transglycosylase (LT) or Goose Egg White Lysozyme (GEWL) |
| Phage 14-1 | gp39<br>Protein domain: Lytic Transglycosylase (LT) or Goose Egg White Lysozyme (GEWL) |
| Phage LBL3 | gp36<br>Protein domain: Lytic Transglycosylase (LT) or Goose Egg White Lysozyme (GEWL) |

TABLE A-continued

| Muralytic Domain (MD) sources | |
|---|---|
| Description | Details |
| Phage LMA2 | gp38<br>Protein domain: Lytic Transglycosylase (LT) or Goose Egg White Lysozyme (GEWL) |
| Phage PB1 | gp39 |
| Phage SN | gp40<br>Protein domain: Lytic Transglycosylase (LT) or Goose Egg White Lysozyme (GEWL) |
| Phage phiKZ | orf181<br>Protein domain: Lytic Transglycosylase (LT) or Goose Egg White Lysozyme (GEWL) |

III. Membrane Traversing Domains

To reach the interior and effectively infect a host cell, a phage must cross the structural layers which surround the cell. In a Gram-positive bacterial cell, from the outside, these are the peptidoglycan layer and the inner cell membrane. In a Gram-negative bacterial cell, there is an additional lipid bilayer outer membrane surrounding the peptidoglycan layer. This additional lipid bilayer forms another compartment between the outer and inner membranes, which is the periplasmic space. See, e.g., Silhavy, et al. (2010) *CSH Persp. Biol.* 2:a000414; Bos, et al. (2007) *Ann. Rev. Microbiol.* 61:191-214; Nanning a (1998) *Microbiol and Molec. Biol. Revs.* 62:110-129; and Costerton, et al. (1974) *Bacteriol. Revs.* 38:87-110. The environment of the periplasmic space serves as an intermediate barrier. The peptidoglycan is typically much thinner in a Gram-negative bacteria compared to a thicker peptidoglycan layer in Gram-positive bacteria.

Because the bacterial outer membrane is a contiguous bilayer, it serves as a barrier to larger molecules accessing the periplasmic space. The outer membrane is a selective semipermeable barrier that can protect the cell from harmful compounds in the environment, including antibiotics, and efficiently excludes larger proteins (e.g., a murlytic enzyme) from the periplasmic space.

A list of sources for transporting segments that can be used to effect transport of an attached muralytic domain across the membrane includes: mammalian Bacterial Permeability Increasing protein (BPI); P134 and other holins; proteins P11 & P7 from PRD1 phage; TAMEs of *Pseudomonas* phages; Type VI secretion system in *V. cholorae*; holin-like protein (Tmp1) from (goat) skin surface; Apidaecin peptides 1a & 1b; phage P22 tail spike protein; *E. coli* phage phiV10-putative tail fiber protein; hypothetical tail fiber Enterobacteria phage JK06; bacteriophage K1F (a T7-like phage); bacteriophage K1F (a T7-like phage with endo-N-acetylneuraminidase); T7 tail fiber protein-Enterobacteria phage T7; tail fiber protein *Pseudomonas* phage gh-1; and P2 gpH Enterobacteria phage P2. See also, PDBTM, the first comprehensive and up-to-date transmembrane protein selection of the Protein Data Bank (PDB). PDBTM database is maintained in the Institute of Enzymology by the Protein Structure Research Group at the website found at pdbtm.enzim.hu. Additional similar or analogous activities may be found which are similarly annotated, share characteristic motifs with, or are homologous to members of the list. Table B provides additional examples of membrane translocation segments.

TABLE B

| Membrane Translocation Domain (MTDs) sources | |
|---|---|
| Description | Details |
| Phage holin 1 | Phage proteins for bacterial lysis typically include a membrane-disrupting protein, or holin |
| ABC_membrane | ABC transporters are involved in the export or import of a wide variety of substrates ranging from small ions to macromolecules. They are found only in prokaryotes and their four constitutive domains are usually encoded by independent polypeptides (two ABC proteins and two transmembrane domain (TMD) proteins) |
| TonB | The sequences in this set all contain a conserved C-terminal domain which is characteristic of TonB and is homologs. A proline-rich repetitive region is found N-terminal to this domain; these low-complexity regions are highly divergent and cannot readily be aligned. The region is suggested to span the periplasm. |
| LolA | The LolA-lipoprotein complex crosses the periplasm and then interacts with outer membrane receptor LolB, which is essential for the anchoring of lipoproteins to the outer membrane. |
| Mem_trans | This entry represents a mostly uncharacterised family of membrane transport proteins found in eukaryotes, bacteria and archaea. These proteins are typically 600-700 amino acid residues long and exhibit 8-12 transmembrane segments. |
| YojJ | YojJ is the N-terminus of a family of bacterial proteins some of which are associated with DUF147 PF02457 towards the C-terminus. It is a putative membrane-spanning protein |
| Mistic | Mistic is an integral membrane protein that folds autonomously into the membrane. It is conserved in the Bacilli bacteria. The protein forms a helical bundle with a polar lipid-facing surface |

TABLE B-continued

| Membrane Translocation Domain (MTDs) sources | |
|---|---|
| Description | Details |
| Trans membrane domain (TMD) of Bacterial permeability increasing protein (BPI) | BPI is produced by neutrophils and is known to bind to OM of gram negative bacteria. A TMD was identified by bioinformatics analysis. |
| TMD from P134 holin | Holins are known to insert into the inner membrane(IM) of bacteria during phage lysis. The TMD is the region that is inserted into the IM. Purifying holins is a challenge since the cells lyse 45 minutes after expression and the holins get inserted into the membrane. Hence decided to use TMD of holins fused to GP36. |
| Proteins P11 & P7 from PRD1 phage | The protein P11 & P7 belongs to the DNA delivery apparatus of PRD1. After attachment by the spike complex to the IncP encoded DNA transfer complex, the receptor binding signals are transferred to the DNA delivery apparatus and leads to conformational change in the PRD1 vertex. This results in removal of spike complex and opening of the vertex which enables a tail to protrude containing proteins P11 & P7(Lytic transglycosylase). P11 has been located on the viral membrane and is strongly adhesive. It is believed that P11 interacts with OM followed by P7 which gains access to the peptidoglycan. |
| Virion associated muralytic enzymes(VAMEs) of bacteriophages | Analysis & identification of potential OM traversing molecules from VAMEs of bacteriophages |
| Antimicrobial peptides | Anionic peptides, Linear cationic alpha helical peptides, Cationic peptides enriched for specific amino acids, Anionic and cationic peptides that contain cysteines and form disulfide bonds and Anionic and cationic peptides fragments of larger proteins. |
| Bacteriocins | S type Pyocins: Protease sensitive. S1, S2, S3 & AP41 cause cell death by DNA breakdown. S4 is predicted to have tRNase activity & S5, cytoplasmic membrane pore forming activity. Have 3 domains, N terminal receptor binding domain, translocation domain & C terminal killing domain. R & F type pyocins from Pseudomonas. Colicins from *E.coli*; Channel-forming colicins (colicins A, B, E1, Ia, Ib, and N) are transmembrane domains that depolarize the cytoplas-mic membrane. Have 3 domains, N ter translocation domain, binding domain & C ter killing domain. Initial binding is to porins and outer membrane proteins. |
| Lipopolysacharide binding protein (LBP) | LBP binds to lipid A outer membrane on bacterial cells. LBP plays an important role in the clearance of bacteria from the circulation that is mediated by CD14. |
| Mannose binding protein (MBP) | Human MBP MBP selectively recognizes the carbohydrate patterns that decorate microorganisms such as bacteria, yeast, parasites, mycobacteria, and certain viruses. MBP does not recognize the sugars that decorate self-glycoproteins. |
| Toll like receptors (TLR) | Are single, membrane-spanning, non-catalytic receptors that recognize structurally conserved molecules derived from Microbes |
| Type VI secretion system in *V. cholerae* | |
| Holin like protein (Tmp1) from goat skin surface | |
| Apidaecin peptides 1a & 1b | |
| P22 Tail spike protein | Recognizes 0 antigen on surface of *Salmonella*; Has endo rhamnose activity (667 amino acids) |
| *E coli* phage phiV10- putative tail fiber protein | LPS degrading activity reported |
| Hypothetical tail fiber Enterobacteria phage JK06 | |
| Bacteriophage K1F, a T7-like phage | |
| Bacteriophage K1F, a T7-like phage with endo-N-acetylneuraminidase | |
| T7 tail fiber protein-Enterobacteria phage T7 | |
| Tail fiber protein *Pseudomonas* phage gh-1 | |
| P2 gpH Enterobacteria phage P2 | |
| Human Cathelecidins-hCAP18, LL37. | |
| Human defensins | |
| Mammalian lysozymes | |
| Mammalian lactoferrin | |
| Mammalian lactoperoxidase | |
| Surfactant proteins A and D (Collectins) produced by | |

TABLE B-continued

| Membrane Translocation Domain (MTDs) sources | |
|---|---|
| Description | Details |
| pulmonary cells<br>Chemokine ligand 20<br>(CCL20) produced by airway<br>epithelial cells | |

In some embodiments, the translocating function can be achieved by chemical structure instead of a protein domain. As described above, alternative muralytic segments can have different efficiencies of transfer across an outer membrane.

Rates of transfer across the outer membrane can be measured by a number of methods. One method is to indirectly evaluate the results of transfer, e.g., the effects of a muralytic segment reaching its periplasmic substrate. The criteria of measurement can be release of measureable cell contents, substrate release, or cell lysis. Cell killing can also be a surrogate measure of peptidoglycan digestion. See Examples section below describing binding of product to cell.

A more direct method is to track the number of molecules transferred into the periplasmic space, e.g., using a detectable label. The efficiency of transfer of a particular transfer segment will often be evaluated by measuring an amount of passenger segment transferred. A detectable label can be used to differentiate between the periplasmic space conditions (more oxidizing than outside the OM) and the extracellular environment. See Rajarao et al. (2002) *FEMS Microbiology Letters* 215:267-272.

An efficient membrane transfer segment will effect at least a 3 fold increase in the level of killing of target host by the muralytic domain, or at least a 3-fold increase in the level of transfer, as compared to absence of the membrane transfer segment. In some embodiments, the membrane transfer segment will increase the level of killing or transfer by at least 5, 7, 10, 15, 20, 30, 50, 80, 100, 150, 250 or more fold compared to the absence of the membrane transfer segment. The assay is typically carried out under conditions which approximate the concentrations which might be used according to the application. The assay will typically measure transfer over a time period ranging from minutes, e.g., 1, 2, 5, 10, 15, or 30 minutes, to an hour or two.

IV. Linkers Connecting Segments; Chemical Conjugation

The invention includes chimeric proteins which comprise two distinct domains from heterologous sources. In some embodiments, the two domains are part of a single polypeptide as a contiguous (chimeric) protein. The two segments can be connected in either order, with the muralytic domain N-proximal to the membrane transfer domain (MTD) or vice versa. The segments can be linked directly or with a linker (peptide or non-peptide). On occasion, the term transmembrane domain (TMD) will be used. The function may be more passive in the biophysical features of thermodynamic interaction of the peptide with the hydrophobic membrane bilayer, or may be interacting with an active process of serving as a segment which interacts with an active transport process, e.g., as the recognition component of an active transport mechanism which transfers the entity from outside to inside the bacterial outer membrane of a Gram-negative bacteria.

In some embodiments, the MTD can transfer the muralytic segment across the inner membrane of a prokaryotic production host. In some embodiments, the MTD does not transfer the MD across the inner membrane, while retaining MTD activity for the outer membrane of a Gram negative bacteria. In some embodiments, the constructs described herein can be produced instead in a eukaryotic cell system.

In some embodiments, the component segments are produced separately and linked chemically. In some cases, synthetic polymerization methods are used to add peptides to existing sequences.

Chemical linkages or bioconjugation technologies may be used. See, e.g., Niemeyer (ed. 2010) *Bioconjugation Protocols: Strategies and Methods* (*Methods in Molecular Biology*) Humana Press; Hcrmanson (2008) *Bioconjugate Techniques* (2d ed.) Academic Press; Lahann (ed. 2009) *Click Chemistry for Biotechnology and Materials Science* Wiley; Rabuka (2010) "Chemoenzymatic methods for site-specific protein modification" *Curr Opin Chem. Biol.* 14:790-96. Epub 2010 Oct. 26; Tiefenbrunn and Dawson (2010) "Chemoselective ligation techniques: modern applications of time-honored chemistry" *Biopolymers* 94:95-106; Nwe and Brechbiel (2009) "Growing applications of "click chemistry" for bioconjugation in contemporary biomedical research" *Cancer Biother Radiopharm.* 24:289-302; de Graaf, et al. (2009) "Normatural amino acids for site-specific protein conjugation" *Bioconjug Chem.* 20:1281-95; the journal *Bioconjugate Chemistry* (ACS); and Thordarson, et al. (2006) "Well-defined protein-polymer conjugates—synthesis and potential applications" *Applied Microbiology and Biotechnology* 73:243-254, DOI: 10.1007/s00253-006-0574-4. For example, specific amino acids can be incorporated or added at either end, perhaps to constructs which have removed non-critical like residues, e.g., for cysteine residues. Accessible cysteine residues can be used to connect the segments by disulfide linkages. Cysteine residues can also be linked with bifunctional maleimide linkers with thioether bonds. The linkers can also have a hydrocarbon spacer of appropriate length, e.g., 6, 9, 12, 15, 18, 21, 25, 29, 35, or more carbon chains.

Constructs were generated having accessible cysteines flanking the GP36 CD lysozyme region, at either or both the N-terminus and C-terminus. These can be used to attach a variety of other chemical moieties. Longer non-peptide hydrophobic molecules can be attached to a Cys residue, including palmityl or similar groups, e.g., using an alkyl or acyl halide, e.g., palmityl bromide, or acyl chloride. The alkyl form will provide a stable thioether linkage while the acyl form will provide a less stable thioester link. The alkyl or acyl hydrocarbon can integrate into the outer membrane outer leaflet, which will flip to the inner leaflet at a detectable rate e.g., increasing with temperature.

V. Definitions

A "cell wall degrading activity" is an enzymatic activity that degrades, breaks down, disintegrates, or diminishes or reduces the integrity of a bacterial cell wall (peptidoglycan layer). Unless indicated otherwise, e.g., by context, the term "muralytic" is used generically to mean "cell wall degrading." Most wall degrading catalytic activities are hydrolytic. Thus, much of the terminology used refers to "muralytic" even if the catalytic mechanism does not involve hydrolysis. Degradation of defined or artificial substrates can be used to measure muralytic or static activity on a populational basis for the target. "Cell wall muralytic activity" in a phage context is usually a characterization assigned to a structure based upon testing under artificial conditions, but such characterization can be specific for bacterial species, families, genera, or subclasses (which may be defined by sensitivity). Therefore, a "bacterium susceptible to a cell wall degrading activity" describes a bacterium whose cell wall is degraded, broken down, disintegrated, or that has its cell wall integrity diminished or reduced by a particular cell wall degrading activity or activities. As explained herein, other cell wall degrading activities originate from the host bacterial cells, or on the phage structure (e.g., to serve in penetration, but abortive to phage replication if destructive to the host cell before intact phage are ready to be released). The structures useful in the penetration steps are particularly relevant to the present invention in that these activities operate on normal hosts from the exterior.

In some circumstances, a prophage sequence can be detected in a bacterial genome. The prophage is often the remnants of an integrated phage genome which may have lost certain essential functions, and thus is embedded therein reflecting past biological function. See, e.g., Kropinski, et al. (2007) *Methods Mol. Biol.* 394:133-75; Canchaya, et al. (2004) *Mol. Microbiol.* 53:9-18; Canchaya, et al. (2003) *Microbiol Mol Biol Rev.* 67:238-76; and Casjens (2003) *Mol Microbiol.* 49:277-300. Although a prophage can encode a substantial portion of the functions of a lytic phage genome, the prophage normally does not pass through a lytic cycle. Many of the structural components of a lytic phage have equivalent or counterpart forms discoverable from a prophage sequence. Informatics analysis can typically determine the difference between a sequence which once encoded the lytic activity used for infection as compared to an endolysin activity used to lyse the target host cell after phage assembly.

A "binding segment" refers to a targeting motif, which can recognize specific structures on the bacterial outer surface. In Gram-positive bacteria, the outer surface of the bacteria is typically the murein layer (cell wall). Thus, a binding segment for Gram positive bacteria can target a cell surface entity, e.g., protein, lipid, sugar, or combination. Binding segments from lysozymes, endolysins, and such are known and can be used. Other proteins which bind to bacteria include the PGRPs described below, the TLRs, flagellum and pili binding entities, and phage tail proteins involved in target recognition. In Gram-negative bacteria, the outer membrane presents various structures which can be targets for specific binding. The outer leaflet of the lipid bilayer or lipopolysaccharide can be exposed to the external environment.

A "membrane transfer domain (MTD)," also referred to as a TMD (transmembrane domain), translocating domain, transfer segment, and like terms, refers to a molecular entity, e.g., a polypeptide domain or chemical entity, which can effect transfer of a linked muralytic segment across the outer membrane of a Gram negative bacteria. Such domain may itself have the ability to translocate the associated segment across the membrane, or be recognized by an endogenous translocation system which will effect transport of the linked catalytic segment. The chimeric polypeptide can be transferred intact across the membrane, or be modified during translocation. In some embodiments, the MTD does not significantly penetrate the inner membrane of an expression host. In some embodiments, the MTD does not significantly penetrate the cell membrane of a eukaryotic cell.

Although the outer membrane of Gram-negative bacteria protects cells from many external agents, it is possible to weaken it specifically by various agents, collectively called permeabilizers, which help to disintegrate the LPS layer and increase the permeability of the OM to hydrophopic agents. Permeabilizers are compounds that weaken the OM and can thus increase the activity of antimicrobials by facilitating entry of external substances capable of inhibiting or destroying cellular functions. This entry may be across the OM into the periplasmic space and perhaps ultimately into the cell cytoplasm. Permeabilizers themselves may not be bactericidal, but may potentiate the activity of other compounds, thus providing the possibility of synergistic action. The classical example of permeabilizers is the chelator EDTA, which sequesters divalent cations that contribute to the stability of the OM by providing electrostatic interactions with proteins and LPS. Treatment with EDTA releases a large proportion of LPS from the OM, exposing hydrophobic phospholipids and creating a hydrophobic pathway for certain substances. This is noticeable as an increased susceptibility to hydrophobic agents. Permeabilsers may not be applicable in therapeutic contexts since at high concentrations they are often toxic to cells. In other contexts, they may be useful, e.g., in surface or device sterilization applications. At lower concentrations they are able to act in permeabilising the outer membrane thus allowing access for molecules to reach the peptidoglycan.

TABLE C

Agents with outer membrane disrupting activity

| Designation | Agent | Mode of action |
|---|---|---|
| A | Chelators | |
| 1 | Ethylenediaminetetraacetic acid | Removes stabilizing cations from the OM, notably Ca2+ and Mg2+.<br>Releases LPS to the external medium and creates a hydrophobic pathway. |
| 2 | Na-hexametaphosphate | Removes stabilizing cations from the OM, notably Ca2+ and Mg2.<br>Increases sensitivity to hydrophobic antibiotics. |
| 3 | Na2-pyrophosphate, Na-orthophosphate | Destabilizes OM. Sensitizes cells to nisin |

TABLE C-continued

| Agents with outer membrane disrupting activity | | |
|---|---|---|
| Designation | Agent | Mode of action |
| 4 | Nitrilotriacetic acid | Disintegrates the OM. Increases sensitivity to hydrophobic antibiotics. |
| B | Polycationic agents | |
| 1 | Polymyxins<br>Tris (high concentrations) | Displaces cations from the OM, causes membrane damage.<br>Binds to OM and increases sensitivity to hydrophobic antibiotics |
| 2 | Polymyxin B nonapeptide | Permeabilizes the OM without significant release of LPS.<br>Increases the cell surface hydrophobicity. |
| 3 | Poly-L-ornithine, Poly-L-lysine | Permeabilises the OM to hydrophobic antibiotics and releases LPS. |
| 4 | L-Ascorbate, Acetylsalicylate | Destabilizes the OM |
| 5 | Lactoferrin, ransferring | Releases LPS, increases sensitivity to rifampin |
| 6 | Cationic detergents, e.g. benzalkonium chloride | Destabilizes hydrophobic interactions in OM |
| 7 | Polyethyleneimine | Intercalates in the OM and increases the membrane surface area without liberation of LPS-associated cell material. Sensitizes target cells to hydrophobic antibiotics and to detergents; causes the formation of vesicular structures on the surface of OM. |
| C | Membrane-perturbing proteins and peptides | |
| 1 | Synthetic cationic peptides<br>Cationic amphiphilic peptides | Disorganization of LPS by interaction of the peptide with the anionic and hydrophobic lipid A. |
| D | Terpenoid and phenolic compounds found in berries and herb plants | |
| 1 | Thymol, carvacrol | Destabilizes the OM and causes LPS release |
| 2 | Gallic acid | Displaces cations from the OM, causes membrane damage and LPS release. |
| 3 | Phenolic berry extracts (cloudberry and raspberry) | Displaces cations from the OM, causes membrane damage and LPS release. |
| E | Organic acids and their salts | |
| 1 | Citric acid | cations from the OM, notably Ca2+ and Mg2+, induces release of LPS. |
| 2 | Succinate, acetate, citrate | Weakly increases membrane permeability |
| F | Other compounds | |
| 1 | Chitosan (polymeric β-1,4-N-acetylglucosamine | Binds to OM resulting in the loss of barrier function |
| 2 | Quinolones Low amounts (0.25 × MIC) | Increases the sensitivity of Gram-negative bacteria to antimicrobial peptides by interacting with the OM by removal of stabilizing divalent cations from LPS-binding sites. |

An "environment" of a bacterium can include an in vitro or an in vivo environment. In vitro environments can include a reaction vessel, e.g., holding isolated or purified bacteria, a surface to be sterilized (e.g., in a public health facility), equipment, surfaces in animal quarters, or public health facilities such as water, septic, or sewer facilities. Other in vitro conditions can provide mixed species populations, e.g., including a number of symbiotically or interacting species in close proximity. An in vivo environment can be a host organism infected by a target bacterium. In vivo environments include organs, such as bladder, kidney, lung, skin, heart and blood vessels, stomach, fur, intestine, liver, brain or spinal chord, sensory organs, such as eyes, ears, nose, tongue, pancreas, spleen, thyroid, etc. In vivo environments include tissues, such as gums, nervous tissue, lymph tissue, glandular tissue, and biological fluids, e.g., blood, sputum, etc. Catheter, tubing, implant, and monitoring or treatment devices which are introduced into or attached to the body may be sources of infection under normal usage. Environments also include the surface of food, e.g., fish, meat, or plant materials. Meats include, e.g., beef, pork, chicken, turkey or other poultry. Plant materials include vegetable, fruits, or juices made from fruits and/or vegetables, or may include clothing or shelter. In some embodiments, surfaces that have come in contact with a bacterially-infected food product are treated with a protein of the invention, including a VAME construct or chimera, e.g., GP36 CD segment or P225. Sucrose and/or sorbitol may be useful to increases the osmotic pressure to make targets more susceptible to degradation of peptidoglycan layer.

"Introducing" a composition to an environment includes applying or administering a compound or composition, and such that a targeted bacteria is exposed to the compound or composition. Introducing said compound or composition can be effected by live or dead bacteria which may produce or release such.

A "cell wall degrading protein" is a protein that has detectable, e.g., substantial, degrading activity on an accessible cell wall or components thereof. "Muralytic" activity can be a result of the degrading activity. Exemplary degrading polypeptides include, e.g., GP36 CD segment or P225 products, and functional structurally related entities, mutant and variants thereof. Examples of cell wall degrading proteins are described in the sequence listing, or derived, e.g., from phage phiKMV (see NC_005045), or from the highly homologous ORF36 from phage phiKMV (see Gene ID 1482616; and NP_877475). Similar degrading domains can be identified by motif analysis, their gene locations in the phage genome (or analogous prophage sequence), their structural location on the phage (or prophage counterpart) structure, e.g., tails or contact points of natural phage, similar motifs from mutated phage remnants (e.g., pyocins), or encoded by prophage sequences. Cell wall degrading domains can be derived, e.g., from the tail plates of myoviridae phage or ends of tails from siphoviridae phage, and other phage virion muralytic polypeptides.

A "GP36 catalytic domain (CD) polypeptide" or grammatical variant thereof, refers to a polypeptide sequence exhibiting lytic (bacteriostatic) activity, typically encoded by the *Pseudomonas* phage P134 sequence highly homologous to ORF36 of phage phiKMV, or closely related mutant or variant phage. SEQ ID NO: 1 provides the sequence of a segment of *Pseudomonas* phage P134 that is highly homologous to a corresponding ORF36 of the phage phiKMV. Exemplary variant ORF36 polypeptides include polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over one or more regions, e.g., of at least about 8, 12, 17, 25, 33, 50, 65, 80, 100, 200, or more amino acids, to an amino acid sequence encoded by an ORF36 nucleic acid from *Pseudomonas* phage P134 which is homologou to phiKMV, see, e.g., Accession Number 1482616, (2) bind to antibodies, e.g., polyclonal antibodies, raised against a substantially purified immunogen comprising an amino acid sequence of an active fragment of ORF36, and conservatively modified variants thereof; or (3) specifically hybridize under stringent hybridization conditions to an anti-sense strand corresponding to a natural nucleic acid sequence encoding the ORF36 polypeptide, and conservatively modified variants thereof; or (4) have a nucleic acid sequence that has greater than about 65%, 70%, 75%, 80%, 85%, 90%, or 95%, preferably greater than about 96%, 97%, 98%, 99%, or higher nucleotide sequence identity, preferably over a region of at least about 25, 50, 100, 150, 200, 250, 300, 400, 500, 600, 700, etc., or more nucleotides, to the ORF36 encoding nucleic acid or a nucleic acid encoding fragment thereof. An example of a GP36 CD is the lysozyme domain running from amino acids 737-875 GP36. The nucleic acids and proteins of the invention include both natural or recombinant molecules. The full length ORF36 polypeptide and truncated fragments thereof can be tested for degradative activity on cell wall components to determine boundaries critical for desired properties. In preferred embodiments, GP36 catalytic domain polypeptide has bacteriostatic activity against various *Pseudomonas, Escherichia, Klebsiella, Acinetobacter, Salmonella, Proteus, Shigella*, and *Burkholderia* bacteria. Some embodiments may also exhibit activity on Gram-positive bacteria, which lack the outer membrane. The concentration, time of action, temperature, and conditions may be optimized to have such activity on gram-positive targets.

Nucleic acids encoding cell wall degrading polypeptides can be amplified using PCR primers based on the sequence of described cell wall degrading polypeptides. For example, nucleic acids encoding GP36 CD polypeptide variants and fragments thereof, as well as likely wall degrading activity candidates, can be amplified using primers. See, e.g., Vybiral et al. (2003) *FEMS Microbiol. Lett.* 219:275-283. Thus, cell wall degrading polypeptides and fragments thereof include polypeptides that are encoded by nucleic acids that are amplified by PCR based on the sequence of the identified cell wall degrading polypeptides. In a preferred embodiment, a bacteriostatic polypeptide or fragment thereof is encoded by a nucleic acid that is amplified by primers relevant to the GP36 CD sequences described.

A "phage particle component" refers to, e.g., a head or tail component of a phage, e.g., phage phiKMV. The invention provides that many different phage types can be sources of the muralytic activity ascribed to the phage components. See, e.g., Piuri and Hatfull (2006) *Molecular Microbiology* 62:1569-1585. Related sequences can be found in prophages or incomplete phage genomes, typically found integrated into the bacterial host chromosome. Tail components typically mediate the recognition and attachment of the phage to the target host, and can possess cell wall degrading activities which assist in penetration of phage components into the host.

"GMP conditions" refers to good manufacturing practices, e.g., as defined by the Food and Drug Administration of the United States Government. Analogous practices and regulations exist in Europe, Japan, and most developed countries.

The term "substantially" in the above definitions of "substantially pure" generally means at least about 60%, at least about 70%, at least about 80%, or more preferably at least about 90%, and still more preferably at least about 92%, 95%, 97%, or 99% pure, whether protein, nucleic acid, or other structural or other class of molecules.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analog refers to a compound that has the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain a basic chemical structure as a naturally occurring amino acid. Amino acid mimetic refers to a chemical compound that has a structure that is different from the general chemical structure of an amino acid, but that functions in a manner similar to a naturally occurring amino acid.

"Protein", "polypeptide", or "peptide" refers to a polymer in which most or all of the monomers are amino acids and are joined together through amide bonds, alternatively referred to as a polypeptide. When the amino acids are α-amino acids, either the L-optical isomer or the D-optical isomer can be used. Additionally, unnatural amino acids, e.g., β-alanine, phenylglycine, and homoarginine, are also included. Amino acids that are not gene-encoded may also be used in the present invention. Furthermore, amino acids that have been modified to include appropriate structure or reactive groups may also be used in the invention. The amino acids used in the present invention may be the D- or L-isomer, or mixtures thereof. The L-isomers are generally preferred. In addition, other peptidomimetics are also useful in the present invention. For a general review, see, Spatola, A. F., in Weinstein, et al. (eds. 1983) Chemistry and Biochemistry of Amino Acids, Peptides and Proteins, Marcel Dekker, New York, p. 267.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. In particular, fusions of sequence may be generated, e.g., incorporating an upstream secretion cassette upstream of desired sequence to generate secreted protein product.

A "fusion protein," "chimeric protein," "protein conjugate," and like terms refer to a protein comprising amino acid sequences that are in addition to, in place of, less than, and/or different from the amino acid sequences encoding the original or native full-length protein or subsequences thereof. More than one additional domain can be added to a cell wall muralytic protein as described herein, e.g., an epitope tag or purification tag, or multiple epitope tags or purification tags. Additional domains may be attached, e.g., which may add additional muralytic activities (on the target or associated organisms of a mixed colony or biofilm), targeting functions, or which affect physiological processes, e.g., vascular permeability or integrity of biofilm. Alternatively, domains may be associated to result in physical affinity between different polypeptides to generate multichain polymer complexes.

The term "nucleic acid" refers to a deoxyribonucleotide, ribonucleotide, or mixed polymer in single- or double-stranded form, and, unless otherwise limited, encompasses known analogues of natural nucleotides that hybridize to nucleic acids in a manner similar to naturally occurring nucleotides. Unless otherwise indicated or by context, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes typically include at least promoters and/or transcription termination signals. Typically, the recombinant expression cassette includes a nucleic acid to be transcribed (e.g., a nucleic acid encoding a desired polypeptide), and a promoter. Additional factors for effecting expression can be included. In certain embodiments, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In certain embodiments, a recombinant expression cassette encoding an amino acid sequence comprising a muralytic activity on a cell wall is expressed in a bacterial host cell.

A "heterologous sequence" or a "heterologous nucleic acid", as used herein, is one that originates from a source foreign to the particular host cell, or, if from the same source, is modified from its original form. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, or at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and, e.g., HPLC or mass spectroscopy or a similar means for purification may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the sequence comparison algorithms or by visual inspection. In certain alignments of identity, no gaps are permitted, while in other algorithms, gaps are allowed with appropriate penalty measures.

The phrase "substantially identical," in the context of two nucleic acids or proteins, refers to two or more sequences or subsequences that have, over the appropriate segment, at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over one or more region of the sequences that corresponds to at least about 13, 15, 17, 23, 27, 31, 35, 40, 50, or more amino acid residues in length, more preferably over a region of at least about 60, 70, 80, or 100 residues, and most preferably the sequences are substantially identical over at least about 150 residues, or over the entire length of the reference sequence. It will be noted that three of the constructs specifically described have high hydrophobic stretches of 23, 23, and 30 amino acids, and data is presented that at least 3 of 23 amino acid residues may be substituted with nonconservative residues while maintaining activity.

For sequence comparison, typically one sequence acts as a reference sequence, to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these and related algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc. (1995 and Supplements) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (ncbi.nlm.nih.gov) or similar sources.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at each position where an arginine is specified by a codon, the codon can be altered to another of the corresponding codons described without altering the encoded protein. Such nucleic acid variations are "silent variations," which are one species of "conservatively modified variations." Each polynucleotide sequence described herein which encodes a protein also describes possible silent variations, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is typically implicit in each described sequence.

Those of skill recognize that many amino acids can be substituted for one another in a protein without affecting the function of the protein, e.g., a conservative substitution can be the basis of a conservatively modified variant of a protein such as the disclosed cell wall muralytic proteins. An incomplete list of conservative amino acid substitutions follows. The following eight groups each contain amino acids that are normally conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton (1984) *Proteins*).

Furthermore, one of skill will recognize that individual substitutions, deletions, or additions which alter, add, or delete a single amino acid or a small percentage of amino acids (typically less than 5%, more typically less than 1%) in an encoded sequence are effectively "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., cell wall muralytic proteins, and nucleic acids which encode proteins yield essentially identical products. For example, due to the degeneracy of the genetic code, "silent substitutions" (e.g., substitutions of a nucleic acid sequence which do not result in an alteration in an encoded protein) are an implied feature of each nucleic acid sequence which encodes an amino acid. As described herein, sequences are preferably optimized for expression in a particular host cell used to produce the cell wall muralytic proteins (e.g., yeast, human, and the like). Similarly, "conservative amino acid substitutions," in one or a few amino acids in an amino acid sequence are substituted with different amino acids with highly similar properties, are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence generally are also "conservatively modified variations".

The practice of this invention can involve the construction of recombinant nucleic acids and the expression of genes in host cells, preferably bacterial host cells. Optimized codon usage for a specific host will often be applicable. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect (baculovirus), mammalian (CHO cells), fungal cells (e.g., yeast, *Pichia, Aspergillus niger*), and bacteriophage expression systems. Note that the N terminal MET is often removed in prokaryotic productions hosts. The presently described chimeric polypeptides include those with and without an N-terminal methionine on any or all of the peptide components.

Examples of protocols sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3:81-94; (Kwoh et al. (1989) *Proc. Natl. Acad. Sci. USA* 86: 1173; Guatelli et al. (1990) *Proc. Natl. Acad. Sci. USA* 87:1874; Lomell et al. (1989) *J. Clin. Chem.* 35:1826; Landegren et al. (1988) *Science* 241:1077-1080; Van Brunt (1990) *Biotechnology* 8:291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

VI. Commercial Applications

Various applications of the polypeptides described herein can be immediately recognized. Many medical conditions result from bacterial infections, described further in infectious disease and medical microbiology textbooks. See, e.g., Kasper and Fauci (2010) *Harrison's Infectious Diseases* McGraw-Hill Professional, ISBN-10: 0071702938, ISBN-13: 978-0071702935; Mandel (2008) *Mandell, Douglas, and Bennett's Principles and Practice of Infectious Diseases Expert Consult Premium Edition* (7th Ed.) Churchill Livingstone, ISBN-10: 0443068399, ISBN-13: 978-0443068393; Schlossberg (ed. 2008) *Clinical Infectious Disease* Cambridge University Press, ISBN-10: 0521871123. ISBN-13: 978-0521871129; Bauman (2011) *Microbiology with Diseases by Body System* (3d ed.) Benjamin Cummings, ISBN-10: 0321712714, ISBN-13: 978-0321712714; and Murray, et al. (2008) *Medical Microbiology* (with Student Consult Online Access, 6th ed.) Mosby, ISBN-10: 0323054706, ISBN-13: 978-0323054706. Therapeutic applications for these polypeptide constructs will be appreciated.

The presently described outer membrane transversing, muralytic chimeric proteins can be used for antibacterial treatment of articles which may be contaminated in normal use. Locations, surfaces, equipment, or environments where target bacteria are public health hazards can be treated using the muralytic polypeptides described herein. Locations of interest include public health facilities where target bacteria containing materials exist. These materials may include waste products, e.g., liquid, solid, or air. Aqueous waste treatment plants may incorporate the muralytic polypeptides to eliminate target bacteria from effluent, whether by treatment with the muralytic polypeptides or cells that express and release the muralytic polypeptides. Solid waste sites can introduce the muralytic polypeptides to minimize possibility of target host outbreaks.

Food preparation areas and equipment can be regularly treated using the muralytic polypeptide compositions, thereby providing means to effectively eliminate target bacteria. Medical and other public environments subject to contamination can use similar means to minimize growth and spread of target microorganisms. The present methods can be used in contexts where elimination of target bacteria is desired, including air filtration systems, e.g., for an intensive care unit.

The chimeric muralytic proteins can be used as a protein stabilizer or a preservative, i.e., where the target bacteria are destabilizing agents. Such compositions can be used as part of the formulation for drugs, or preservative for meat or other food products. In some embodiments, the muralytic polypeptides can be used in aquatic food products, e.g., as a stabilizer or as a component of preservative formulations. Such applications are particularly useful for materials that must be kept antiseptic but cannot contain classical antibiotics.

Alternative applications include use in a veterinary or medical context. Means to determine the presence of particular bacteria, or to identify specific targets may utilize the effect of selective agents on the population or culture. Inclusion of bacteriostatic activities to cleaning agents, including washing of animals and pets, may be desired.

The muralytic polypeptides described herein can be used to treat bacterial infections of, e.g., humans, animals, and plants. The muralytic polypeptides can be administered to a subject prophylacticly or where the subject has a bacterial infection. In addition, the present methods can be applied to display (e.g., zoo or performing), companion (e.g., dogs, cats, other pets), racing (e.g., horses), or farm (e.g., dairy and beef cattle, sheep, goats, pigs, chicken, fish, shrimp, lobster, and the like) animals where the composition is applied to reduce the presence of bacteria. The muralytic polypeptides can be used to treat infections caused by bacteria that replicate slowly, as the killing mechanism does not depend upon host cell replication. Many current antibacterial agents, e.g., antibiotics, are most useful against replicating bacteria. For example, the muralytic polypeptides can be used to target bacteria that replicate with doubling times of, e.g., 1-72 hours, 1-48 hours, 1-24 hours, 1-12 hours, 1-6 hours, 1-3 hours, or 1-2 hours.

Medically relevant Gram-negative cocci species include *Neisseria gonorrhoeae* and spirochaetes (causing a sexually transmitted disease); *Neisseria meningitides* (causing meningitis); and *Moraxella catarrhalis* (causing respiratory symptoms). Relevant Gram-negative bacilli species include *Hemophilus influenzae, Klebsiella pneumoniae, Legionella pneumophila, Burkholderia*, and *Pseudomonas aeruginosa* (respiratory problems); *Escherichia coli, Proteus mirabilis, Enterobacter cloacae*, and *Serratia marcescens* (urinary problems), and *Helicobacter pylori, Salmonella enteritidis, Salmonella typhi* (gastrointestinal problems), and spirochaetes (sexually transmitted disease). Gram-negative bacteria associated with nosocomial infections include *Acinetobacter baumannii*, which cause bacteremia, secondary meningitis, and ventilator-associated pneumonia, e.g., in intensive-care units of hospital establishments.

Other relevant that can be targeted using the present muralytic polypeptides include Gram-negative species include *Stenotrophomonas, Bdellovibrio*, acetic acid bacteria, and alpha-proteobacteria such as *Wolbachia*, the cyanobacteria, spirochaetes, green sulfur and green non-sulfur bacteria.

Gram-variable organisms, which may have an outer membrane under certain conditions (display a Gram-variable pattern with Gram staining), can also be targeted using the present muralytic polypeptides. Gram-variable bacteria include e.g., the genera *Actinomyces, Arthobacter, Corynebacterium, Mycobacterium*, and *Propionibacterium*, which have cell walls particularly sensitive to breakage during cell division, and display Gram-negative staining. In cultures of *Bacillus, Butyrivibrio*, and *Clostridium*, a decrease in peptidoglycan thickness during growth coincides with an increase in the number of cells that stain Gram-negative. In addition, the age of the bacterial culture can influence the results of the Gram stain.

VII. Administration

The route of administration and dosage of the muralytic polypeptides described herein vary with the infecting bacteria strain(s), the site and extent of infection (e.g., local or systemic), and the subject being treated. The routes of administration include but are not limited to: oral, aerosol or other device for delivery to the lungs, nasal spray, intravenous (IV), intramuscular, intraperitoncal, intrathecal, intraocular, vaginal, rectal, topical, lumbar puncture, intrathecal, and direct application to the brain and/or meninges. Excipients which can be used as a vehicle for the delivery of the therapeutic will be apparent to those skilled in the art. For example, the muralytic polypeptide can be in lyophilized form and dissolved (resuspended) prior to administration (e.g., by IV injection). The dosage is contemplated to be in the range of 0.03, 0.1, 0.3, 1, 3, 10, 30, 100, 300, 1000, 3000, 10000 or more muralytic polypeptide molecules per bacterium in the host infection. Depending upon the size of the protein, which may itself be tandemly associated, or in multiple subunit form (dimer, trimer, tetramer, pentamer, etc.) or in combination with one or more other entities, e.g., enzymes or fragments of different specificity, the dose may be about 1 million to about 10 trillion/per kg/per day, and preferably about 1 trillion/per kg/per day, and may be from about $10^6$ killing units/kg/day to about $10^{13}$ killing units/kg/day.

Methods to evaluate killing capacity may be similar to methods used by those of skill to evaluate intact replicating phage, e.g., plaque forming units or pfu, though killing units may be better evaluated by determining the number of surviving bacteria after titration of the killing units. Quantification of killing is distinct, since non-replicating phage will not form plaques on bacterial host lawns. Thus, serial dilution methods can be used to evaluate the quantity of "killing" units in place of standard pfu. Serial dilutions of bacterial cultures exposed to the killing compositions can be used to quantify killing units. Total bacterial counts can be compared with viable colony units can establish the viable fraction of bacteria and what fraction was susceptible to the killing constructs. Other means for evaluating stasis activity may include release of intracellular contents, whether natural or loaded, or enzymatic activity on defined or prepared substrates which correspond to natural cell wall structures.

The therapeutic(s) are typically administered until successful elimination of the pathogenic bacteria is achieved. The invention contemplates single dosage forms, as well as multiple dosage forms of the compositions of the invention, as well as methods for accomplishing sustained release means for delivery of such single and multi-dosages forms. Broad spectrum formulations can be used while specific diagnosis of the infecting strain is determined.

With respect to the aerosol administration to the lungs or other mucosal surfaces, the therapeutic composition is incorporated into an aerosol formulation specifically designed for administration. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. The number of enzyme killing units to be administered per aerosol treatment will typically be in the range of about $10^6$ to $10^{13}$ killing units, e.g., about $10^{12}$ killing units.

Typically, the killing will decrease the host replication capacity by at least 3 fold, e.g., 10, 30, 100, 300, etc., to many orders of magnitude. Slowing the rate of host replication without killing can also have significant therapeutic or commercial value. Genetic inactivation efficiencies may be 4, 5, 6, 7, 8, or more log units.

VIII. Formulations

The invention further contemplates pharmaceutical compositions comprising at least one cell wall degrading enzyme, e.g., muramidase, of the invention provided in a pharmaceutically acceptable excipient. The formulations and pharmaceutical compositions of the invention thus contemplate formulations comprising an isolated enzyme segment specific for a bacterial host; a mixture of two, three, five, ten, or twenty or more enzymes that affect the same or typical bacterial host; and a mixture of two, three, five, ten, or twenty or more enzymes that affect different bacterial hosts or different strains of the same bacterial host, e.g., a cocktail mixture of enzymes that collectively inhibit the growth of multiple Gram-negative bacterial species. In this manner, the compositions of the invention can be tailored to the needs of the patient. The compounds or compositions can be sterile or near sterile.

A "therapeutically effective dose" is a dose that produces the effects, bacteriostatic (reducing bacterial growth) or bactericidal (killing bacteria), for which it is administered. The exact dose will depend on the purpose of the treatment, and will be ascertainable by one skilled in the art using known techniques. See, e.g., Ansel, et al. (2010), *Pharmaceutical Dosage Forms and Drug Delivery*; Lieberman (1992) *Pharmaceutical Dosage Forms* (vols. 1-3), Dekker; Lloyd (1999) *The Art, Science and Technology of Pharmaceutical Compounding*; and Pickar (1999) *Dosage Calculations*. As is known in the art, adjustments for protein degradation, systemic versus localized delivery, as well as the age, body weight, general health, sex, diet, time of administration, drug interaction, and the severity of the condition may be necessary, and will be ascertainable by those skilled in the art.

Various pharmaceutically acceptable excipients are well known in the art. As used herein, "pharmaceutically acceptable excipient" includes a material which, when combined with an active ingredient of a composition, allows the ingredient to retain biological activity and without causing disruptive reactions with the subject's immune system. Such excipients include stabilizers, preservatives, salt or sugar complexes or crystals, and the like.

Exemplary pharmaceutically carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms.

Further included are formulations for liposomal delivery, and formulations comprising microencapsulated enzymes, including sugar crystals. Compositions comprising such excipients are formulated by well known conventional methods (see, e.g., *Remington's Pharmaceutical Sciences*, Chapter 43, 14th Ed., Mack Publishing Col). The proteins may be subjected to PEGylation to achieve advantages often deriving therefrom. See, e.g., Jevsevar, et al. (2010) *Biotechnol. J.* 5:113-128; Brocchini, et al. (2008) *Adv. Drug Delivery Revs.* 60:3-12; Jain and Jain (2008) *Crit. Rev. Ther. Drug Carrier Syst.* 25:403-47, PMID: 190626331; and Shaunak, et al. (2006) *Nature Chemical Biology* 2:312-313. Alternatives exist for achieving similar stabilizing results. See, e.g., Schellenberger, et al. (2009) *Nature Biotechnology* 27:1186-1192.

In general, pharmaceutical compositions can be prepared in various forms, such as granules, tablets, pills, capsules (e.g., adapted for oral delivery), suppositories, microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

The pharmaceutical composition can comprise other components in addition to the muralytic polypeptide, e.g., more than one active ingredient, e.g., two or more, three or more, five or more, or ten or more different enzymes, where the different enzymes may be specific for the same, different, or accompanying bacteria. For example, the pharmaceutical composition can contain multiple (e.g., at least two or more) defined wall degrading enzymes, wherein at least two of the enzymes in the composition have different bacterial host specificity or different peptidoglycan linkage specificity, such as a combination of a transglycolase and an endopeptidase. In this manner, the therapeutic composition can be adapted for treating a mixed infection of different bacteria, or may be a composition selected to be effective against various types of infections found commonly in a particular institutional environment. A select combination may result, e.g., by selecting different groups of cell wall degrading entities derived from various bacteriophage of differing specificity so as to target multiple strains present, or potentially present in the infection. As noted above, the wall degrading enzyme can be administered in conjunction with other agents, such as a conventional antimicrobial agent or a reagent which provides for efficacy against biofilm or capsule forming cultures. Various materials are described, e.g., in Davies and Marques (2009) J. Bacteriology 191: 393-403; Kimura and Itoh (2002) Appl. and Env. Microbiology 69:2491-2497; Kim and Geider (2000) Phytopahtology 90:1263-1268; Hughes, et al. (1998) J. Appl. Microbiology 85:583-590; and Bartell and On (1969) J. Virology 4:580-584. In some embodiments, an additive (e.g., fatty acid) or biofilm depolymerase may be added as an additional domain to the chimeric construct, as an additional component in a formulation, or administered in combination, simultaneously or sequentially, with the cell wall degrading activity. Active constructs based upon the described phage derived polysaccharide depolymerases can be combined with the provided muralytic activities.

IX. Modification of Protein Sequence for Improved Production

MTDs are typically hydrophobic in nature, and a chimeric protein including such an MTD may be insoluble when expressed in a production host such as *E. coli*. Constructs can be generated which exhibit an unexpected combination of properties. As shown in the Examples, a construct can be designed to be sufficiently hydrophilic to remain soluble within the producing cell host, and fail to traverse the producing host cell. The modified construct surprisingly retains the MTD function to traverse the bacterial outer cell wall to effect target bacteria killing. This may be achieved because the bacterial cell membrane properties (and structure) are sufficiently different from the bacterial outer membrane.

Such improved production constructs combine three properties: (1) produced in substantially soluble form in a host cell, typically Gram-negative *E. coli*; (2) retains function of traversing the bacterial outer cell wall to access the periplasmic space where the substrate peptidoglycan is accessible to the catalytic domain; and (3) no substantial disruption of the inner membrane of the producing cell. Appropriate controls (such as the non-modified construct) will be incorporated to ensure that cell survival, expression, and catalytic activity are be quantitated or relatively assessed.

Hydrophilicity positively affects protein solubility, and a protein with regions of concentrated hydrophobicity can be made more soluble by disrupting such regions. As the MTD segments will typically be among the most hydrophobic segments of a chimeric construct, the MTD is most amenable to amino acid substitution.

With certain insoluble (or minimally soluble) constructs from these chimeras, the MTD segment is a short transmembrane segment. Known hydrophobicity measurements can be used to locate transmembrane segments, which typically span about 20 amino acid residues. Decreasing the overall hydrophobicity of these regions will often change the overall protein solubility.

Regions of high hydrophobicity can be identified using DAS TMD analysis (see, e.g., Cserzo, et al. (1997) Protein Engineering 10(6):673-676), transmembrane using hidden Markov models (TMHMM) analysis (see, e.g., Krogh, et al. (2001) J. Mol. Biol. 305(3):567-580), general hydrophobicity (see, e.g., Kyte and Doolittle (1982) J. Mol. Biol. 157(1):105-132), or the Grand Average of Hydropathy Score (GRAVY; see Gasteiger, et al (2005) “Protein Identification and Analysis Tools on the ExPASy Server” in Walker (ed. 2005) *The Proteomics Protocols Handbook*, Humana Press, pp. 571-607).

The Dense Alignment Surface (DAS) prediction server is meant for predicting transmembrane helices in membrane proteins. The program uses the condition that membrane proteins are composed of stretches of 15-30 predominantly hydrophobic residues separated by polar connecting loops. This means that the transmembrane region will detect a fragment that is predominatly composed of hydrophobic amino acids, flanked by residues that are hydrophilic or polar residues. DAS is based on low-stringency dot-plots of the query sequence against a collection of non-homologous membrane proteins using a previously derived, special scoring matrix. Since integral membrane proteins are composed of more hydrophobic residues than water soluble globular proteins, they can be discriminated according to their composition. The principal difference between the DAS method and the hyrdophobicity profile based programs is that DAS describes the hydrophobic segments at three levels. This complex approach of hydrophobicity is the key behind the sensitivity of the DAS method.

DAS plots indicate a “strict” cutoff at 2.2 DAS score, and a “loose” cutoff at 1.7. The hit at 2.2 is informative in terms of the number of matching segments, while a hit at 1.7 gives the actual location of the transmembrane segment. Typically, a DAS score of less than 3 (e.g., less than 2.8, 2.5, or 2.2) over the span of the protein indicates that a protein will be soluble upon overexpression in a host cell.

Amino acids with electrically charged side chains include Arg, His, Lys (positively charged), with hydropathy scores of −4.5, −3.2, and −3.9 respectively; and Glu and Asp (negatively charged), both with hydropathy scores of −3.5. Amino acids with polar but uncharged side chains include Ser, Thr, Asn, and Gln, with hydropathy scores of −0.8, −0.7, −3.5, and −3.2, respectively. Amino acids with non-polar (hydrophobic side chains): Ala, Ile, Leu, Met, Phe, Trp, Tyr, and Val, with hydropathy score being 1.8, 4.5, 3.8, 1.9, 2.8, −0.9, −1.3, and 4.2. Examples of amino acids to substitute for valine include tyrosine, tryptophan, arginine, histidine, or lysine. Examples of amino acids to substitute for isoleucine include tyrosine or tryptophan, arginine, histidine, or lysine. Examples of amino acids to substitute for leucine include tyrosine, tryptophan, arginine, histidine, or lysine.

For example, in FIG. 1A, the peak measure is above about 3.5 for the C-terminal MTD region. The segment was modified to decrease the local DAS profile score, which is reflected in FIG. 1B. Typically, substantial peaks are targeted (e.g., those higher than about 3.1, 3.0, 2.9, 2.7, 2.5) to lower local peak values to less than about 2.2, 2.1, 2.0, 1.8 or 1.5. The decrease in DAS profile score will typically be at least about 0.2, 0.3, 0.4, or 0.5 DAS units. The DAS profile of a MTD segment, however, must remain high enough to effectively transport a chimeric protein comprising the MTD across the outer membrane of a gram negative bacteria.

TMHMM is a software analysis based on a hidden Markov model. It predicts transmembrane helices and discriminates between soluble and membrane proteins with a high degree of accuracy. Methods for prediction of transmembrane helices using hydrophobicity analysis alone are not reliable always. This method implicitly combines the hydrophobic signal to detect transmembrane (TM) segments and the charge bias, an abundance of positively charged residues in the part of the sequence on the cytoplasmic side of the membrane protein into one integrated algorithm. Helical membrane proteins have alternating cytoplamic and non-cytoplasmic loops. TMHMM can incorporate hydrophobicity, charge bias, helix lengths, and grammatical constraints into one model for prediction. This program allows one to predict the location of transmembrane alpha helices and the location of intervening loop regions together with prediction of which loops between the helices will be on the inside or outside of the cell or organelle. This program does not detect beta sheet transmembrane domains. It takes about 20 amino acids to span a lipid bilayer in an alpha helix. Programs can detect these transmembrane domains by looking for the presence of an alpha helix at least about 20 amino acids long which contains hydrophobic amino acids. It correctly predicts 97-98% of the transmembrane helices while Dense Alignment Surface method (DAS) to predict transmembrane segments in any integral membrane protein. DAS has two levels of stringency which is more comprehensive than TMHMM.

To improve solubility of a protein comprising a TMHMM predicted transmembrane domain, hydrophobic amino acids can be substituted or modified, e.g., to decrease the probability of a TMD by about 0.5, 0.6, 0.7, 0.8, or even about 0.9 down to lower values, e.g., in the range of about 0.6 or lower ranges, with a reduction of about 0.2, 0.3, 0.4, or 0.5.

A Kyte-Doolittle hydropathy plot is another predictive measure of protein structure, indicating transmembrane or surface regions. This does not predict secondary structure, so it will detect both alpha helix and beta sheet transmembrane domains. Numbers greater than 0 indicate increased hydrophobicity, numbers less than 0 indicate an increase in hydrophilic amino acids.

First, each amino acid is given a hydrophobicity score between 4.6 and −4.6. A score of 4.6 is the most hydrophobic and a score of −4.6 is the most hydrophilic. After a window size is set, it is the number of amino acids whose hydrophobicity scores will be averaged and assigned to the first amino acid in the window. The default window size is 9 amino acids. The computer program starts with the first window of amino acids and calculates the average of all the hydrophobicity scores in that window. Then the computer program moves down one amino acid and calculates the average of all the hydrophobicity scores in the second window. This pattern continues to the end of the protein, computing the average score for each window and assigning it to the first amino acid in the window. The averages are then plotted on a graph. The y axis represents the hydrophobicity scores and the x axis represents the window number.

The Kyte-Doolittle scale is widely used for detecting hydrophobic regions in proteins. Regions with a positive value are hydrophobic, negative values are more hydrophilic. This scale can be used for identifying both surface-exposed regions as well as transmembrane regions, depending on the used window size. Short window sizes of 5-7 generally work well for predicting putative surface-exposed regions. Large window sizes of 19-21 are well suited for finding transmembrane domains if the values calculated are above about 1.6.

Typically, a Kyte-Doolittle score of less than 3 (e.g., less than 2.8, 2.5, 2.2, or 2.0) over the span of the protein indicates that a protein will be soluble upon overexpression in a host cell. These values should be used as a rule of thumb and deviations from the rule may occur.

Kyte and Doolittle also described an overall GRAVY score, which is the average hydropathy score for all the amino acids in the protein. Integral membrane proteins typically have higher GRAVY scores than do globular proteins. This index is the general average hydropathicity (GRAVY) score for the hypothetical translated gene product. It is calculated as the arithmetic mean of the sum of the hydropathic indices of each amino acid.

Software to calculate GRAVY score is available free online on expasy Protparam. The input is the amino acid primary sequence in single letter format. Since the score is an average value the parameter to be selected is the window size to adjust the number of amino acids that are averaged to obtain an individual hydropathy score.

Typically, proteins with a negative GRAVY score are soluble (though such proteins may associate structurally and functionally with membrane-anchored proteins). Also, several hydrophilic proteins are retained in the lipophilic membrane fraction due to interaction with hydrophobic proteins (Althage, et al. (2004) *Biochim Biophys Acta* 1659:73-82.; Guenebaut, et al. (1997) J. Mol. Biol. 265:409-418; and Guenebaut, et al. (1998) J. Mol. Biol. 276:105-112). GRAVY simply calculates overall hydrophobicity of the linear polypeptide sequence with increasing positive score indicating greater hydrophobicity, but does not account for order of residues, the way the protein folds in three dimensions, or the percentage of residues buried in the hydrophobic core of the protein.

While not the most indicative measure, e.g., compared to DAS, a GRAVY score of less than 1.5 (e.g., less than 1.2, 1.0, or 0.8) typically indicates that a protein will be soluble when expressed in a host cell. In the context of the presently described MTDs, the GRAVY score for the MTD should not dip below −1, to ensure the MTD retains outer membrane transversing activity.

For longer transmembrane or hydrophobic segments, one can localize highly hydrophobic segments or amino acids to target for substitution using alternative methods. For example, one can determine surface exposed amino acid residues and their hydrophobicity index. If the hydrophobicity index or the GRAVY score is on the negative side, then hydrophilic residues can be used to substitute the less hydrophilic moieties. For example, the accessible surface area (ASA) or solvent-accessible surface can be determined. ASA is the surface area of a biomolecule that is accessible to a solvent (Lee and Richards (1971) J. Mol. Biol. 55:379-400). Solvent exposure of amino acids measures how deep residues are buried in tertiary structure of proteins, and can be useful for analyzing and predicting protein structure and function (Li, et al. (2011) Proteomics 11:3793-801; Ahmad, et al. (2003) Proteins 50:629-35).

One can also use neural networks for prediction of surface exposed residues. Data from protein crystal structures are used to teach computer-simulated neural networks rules for predicting surface exposure from sequence. These trained networks are able to correctly predict surface exposure. See, e.g., Holbrook, et al. (1990) Protein Eng. 3:659-665; Rost and Sander (1994) Proteins 20:216-226; Lebeda, et al. (1998) J. Protein Chem. 17:311-318; Pollastri, et al. (2002) Proteins 47:142-153; and Ahmad and Gromiha (2002) Bioinformatics 18:819-824. Other approaches include logistic function (Mucchielli-Giorgi, et al. (1999 Bioinformatics 15:176-177); Bayersian analysis (Mucchielli-Giorgi, et al. (1999) Bioinformatics 15:176-177); Information theory (Naderi-Manesh, et al. (2001) Proteins 42:452-459; Richardson and Barlow (1999) Protein Eng. 12:1051-1054; and Carugo (2000) Protein Eng. 13:607-609); and substitution matrices (Pascarella, et al. (1998) Proteins 32:190-199). A less quantitative approach to predict solvent accessibility is simply based on hydrophobicity plots (see Lesk (2002) *Introduction to Bioinformatics* Oxford University Press).

These methods indicate accessibility of each residue (exposed, buried, and, possibly, intermediate). Residues which are exposed to the solvent are more likely to affect solubility and interact with aqueous solution. The exposed residues can be substituted with a more polar or hydrophilic residue to improve solubility of the protein or domain upon expression.

The following references provide further guidance for improving protein solubility: Trevino, et al. (2007) *J. Mol. Biol.* 366:449-460; Magnan, et al. (2009) Bioinformatics 25:2200-2207; Ahuja, et al. (2006) Malaria Journal 5:52; Smialowski, et al. (2007) Bioinformatics 23:2536-2542; Trevino, et al. (2008) J. Pharm Sci 97: 4155-66; Makrides (1996) Microbiological Reviews 60:512-538; Karlsson, et al. (2005) J. Biol. Chem. 280:25558-564; Maxwell, et al. (1999) Protein Sci. 8:1908-1911; and Wilkinson and Harrison (1991) BioTechnology 9:443448.

X. Modification of Protein for Improved Half-Life, Stability, Storage

Addition of a polyalkylene glycol (PAG) moiety to a polypeptide or other molecule is referred to as PAGylation. PAGylation (typically PEGylation) can improve the pharmacokinetic and pharmacodynamic properties of a polypeptide, e.g., increase in vitro and in vivo activity and stability, increase half-life, reduce proteolytic degradation, reduce immunogenicity, and improve bioavailability and biodistribution. Amino acids that are commonly targeted for PAGylation are arginine, aspartic acid, glutamic acid, tyrosine, serine, threonine, histidine, cysteine, and lysine. The ϵ-amino group on the side chain of lysine is commonly targeted for PAGylation.

Polyethylene glycol (PEG) is commercially available over a wide range of molecular weights from 300 g/mol to 10,000,000 g/mol. Different forms of PEG can be made using different initiators for the polymerization process, the most common of which is a monofunctional methyl ether PEG (methoxypoly(ethylene glycol)), referred to as mPEG. Lower-molecular-weight PEGs are also available as purer oligomers, referred to as monodisperse, uniform or discrete.

PEG molecules can have different geometries. Branched PEGs have three to ten PEG chains emanating from a central core group. Star PEGs have 10-100 PEG chains emanating from a central core group. Comb PEGs have multiple PEG chains normally grafted to a polymer backbone.

Melting points vary depending on the MW of the polymer. PEG has the structure:

$$HO—CH_2—(CH_2—O—CH_2—)_n—CH_2—OH$$

where n=9 would have an average molecular weight of approximately 400 daltons (PEG 400). Ideally, for therapeutic consistency and regulatory reasons, the PEG polymers added to the polypeptide are highly uniform (low dispersity). For a MW of about 5 KDa then n is about 100; and for the MW of about 20 KDa n is about 400.

In addition to amino acid attachment site, considerations for the PEGylation reaction include the initiator PEGylating reagents, the PEG-to-protein ratio, pH, reaction time, and temperature (see, e.g., Seely et al. (2005) "Making Site-specific PEGylation Work: Purification and analysis of PEGylated protein pharmaceuticals presents many challenges" BioPharm International).

Cys specific reagents include iodoacetamide or chloroacetamide chemistries, and maleimide chemistry has also been applied (Kalia and Raines (2010) *Curr Org. Chem.* 14:138-147). PEG maleimide, PEG iodoacetate, PEG thiols, and PEG vinylsulfone are thus useful reagents which allow cysteine specific PEGylation under mild conditions.

Agents that add PEG to the N-terminal amino acid of a given polypeptide include PEG NHS ester, PEG tresylate, PEG aldehyde, PEG isothiocyanate, and several others (Nucci et al. (1991) *Adv. Drug Del. Rev.* 6:133-151; Harris, et al. (1984) *J. Poly. Sci: Polymer Chem. Ed.* 22:341-352; Bailon and Berthold (1998) *Pharm. Sci. Technol. Today* 1:352-356). All react under mild conditions and are quite specific for amino groups. Generally the pK of the alpha-amino group is 1-2 pH units lower than the epsilon-amino group of lysine residues. By PEGylating the molecule at pH 7 or below, high selectivity for the N-terminus is attained.

PEG molecules and conditions for PEGylation are known in the art. See, e.g., Abuchowski, et al. (1984) *Cancer Biochem. Biophys.* 7:175-186; Abuchowski, et al. (1977) *J. Biol. Chem.* 252:3582-3586; Jackson, et al. (1987) *Anal. Biochem.* 165:114-127; Koide, et al. (1983) *Biochem. Biophys. Res. Commun.* 111:659-667; tresylate (Nilsson, et al. (1984) *Methods Enzymol.* 104:56-69; Delgado, et al. (1990) *Biotechnol. Appl. Biochem.* 12:119-128); N-hydroxysuccinimide derived active esters (Buckmann, et al. (1981) *Makromol. Chem.* 182:1379-1384; Joppich, et al. (1979) *Makromol. Chem.* 180:1381-1384; Abuchowski, et al. (1984) *Cancer Biochem. Biophys.* 7:175-186; Katre, et al. (1987) *Proc. Natl. Acad. Sci. U.S.A.* 84:1487-1491; Kitamura, et al. (1991) *Cancer Res.* 51:4310-4315; Boccu, et al. (1983) *Z. Naturforsch.* 38C:94-99); carbonates (Zalipsky, et al. pp. 347-370 in Harris (ed. 1992) *Poly(ethylene glycol) Chemistry: Biotechnical and Biomedical Applications* Plenum Press, New York; Zalipsky, et al. (1992) *Biotechnol. Appl. Biochem.* 15:100-114; Veronese, et al. (1985) *Appl. Biochem. Biotech.* 11:141-152); imidazolyl formates (Beauchamp, et al. (1983) *Anal. Biochem.* 131:25-33; Berger, et al. (1988) *Blood* 71:1641-1647); 4-dithiopyridines (Woghiren, et al. (1993) *Bioconjugate Chem.* 4:314-318); isocyanates (Byun, et al. (1992) *ASAIO Journal* M649-M653); and epoxides (U.S. Pat. No. 4,806,595, issued to Noishiki, et al. (1989)). Other linking groups include the urethane linkage between amino groups and activated PEG (Veronese et al. (1985) *Appl. Biochem. Biotechnol.* 11:141-152.

A bifunctional PEG can be used to as a linker for the muralytic domain and MTD of the chimeric proteins described herein. For example, homobifunctional PEG can be used to conjugate the N-terminus of the MTD to the N-terminus of the catalytic domain (or vice versa). In some embodiments, a Y structure PEG derivative with one branch of the Y having an N-terminus specific group (e.g., aldehyde reactive group) and the other with a C-terminus specific group (e.g., hydrazine) is used. In some embodiments, a linear PEG with the reactive groups at either end is used.

In some embodiments, a cysteine residue is introduced on to the N or C terminus of the domains, and a heterobifunctional PEG (e.g., Thiol-PEG-Amine, a product with one end as thiol and the other end as amine) is used. Boc or Fmoc can be used to block amine groups.

Conjugation reactions can be performed in succession, and may involve purification steps to remove undesired reactants and products. The purification methods will generally be typical peptide purification methods, many of which are known in protein chemistry. These may include size exclusion chromatography, ion exchange chromatography, etc.

The PEG reacting group for a C terminus can be a hydrazine or similar specific reacting group. The reaction will typically be for 0.5-18 hr; at an appropriate reaction temperature, e.g., between 20-40° C.; with appropriate peptide concentrations, e.g., 0.5-3 mg/ml; with appropriate PEG reagent concentrations, e.g., about 1-10 fold excess of PEG to protein target; and appropriate pH, e.g., pH 4-7. The reaction can be terminated, the reactants removed, and the desired PEGylated polypeptide isolated.

The reaction linking the domain-PEG reacting group to the N terminus of the other domain can be an aldehyde or similar specific reacting group. Again, the reaction can run for an appropriate time, at an appropriate reaction temperature, with appropriate peptide concentrations, and with appropriate reagent concentrations, and appropriate pH.

Methoxypolyethylene glycol tresylate (mPEG-tresylate MW 5 kDA) can be used for lysine specific PEGylation of the target protein. Typically, mPEG-tresylate is incubated with the protein at 30° C. for 3 hr.

Methoxypolyethylene glycol maleimide (mPEG-maleimide, MW 5 kDA), a cysteine specific PEG targeting reagent, can be used to PEGylate the desired protein. Typically, mPEG-maleimide is reacted with the target protein at 30° C. for 3 hr.

Methoxypolyethylene glycol propionaldehyde is an N terminal specific PEG targeting reagent (mPEG-aldehyde, MW 20 kDA). Typically, mPEG-aldehyde is incubated with the desired protein at 30° C. for 3-4 hr.

Standard SDS-PAGE electrophoresis is routinely employed to monitor the PEGylation reaction and the products of the derivitization. Anomalous SDS-PAGE migration as compared to molecular weight markers typically results from the non-linear nature of the PEGylated products. In particular, because the PEG provides different SDS binding compared to protein, migration of standard proteinaceous molecular weight markers does not correlate with the migration of protein derivatized with different integral numbers of PEG moieties. The stoichiometry of binding of SDS to the PEG is different from linear protein, and the charge ratio is non-linear.

The extent of PEGylation can be determined using a microfluidic based electrophoresis system, the Agilent 2100 Bioanalyzer (P230 assay). For the Bioanalyzer, protein loading and on-chip sample analysis were performed as described in the manufacturer's protocol. See Protein 230 Kit Guide, Agilent Technologies Publication Number G2938-90054. PEGylation reactions typically result in differently PEGylated protein species (un-, mono-, di-, tri-, etc.), having different numbers of PEG moieties attached.

XI. Methodology

Production and use of the presently described chimeric polypeptides involve well-known methods general clinical microbiology, general methods for handling bacteriophage, and general fundamentals of biotechnology, principles and methods. References for such methods are listed below.

A. General Clinical Microbiology

General microbiology is the study of the microorganisms. See, e.g., Sonenshein, et al. (ed. 2002) *Bacillus Subtilis and Its Closest Relatives: From Genes to Cells* Amer. Soc. Microbiol.; Alexander and Strete (2001) *Microbiology: A Photographic Atlas for the Laboratory* Benjamin/Cummings; Cann (2001) *Principles of Molecular Virology* (3d ed.); Garrity (ed. 2005) *Bergey's Manual of Systematic Bacteriology* (2 vol. 2d ed.) Plenum; Salyers and Whitt (2001) *Bacterial Pathogenesis: A Molecular Approach* (2d ed.) Amer. Soc. Microbiol.; Tierno (2001) *The Secret Life of Germs: Observations and Lessons from a Microbe Hunter* Pocket Star; Block (ed. 2000) *Disinfection, Sterilization, and Preservation* (5th ed.) Lippincott Williams & Wilkins Publ.; Cullimore (2000) *Practical Atlas for Bacterial Identification* Lewis Pub.; Madigan, et al. (2000) *Brock Biology of Microorganisms* (9th ed.) Prentice Hall; Maier, et al. (eds. 2000) *Environmental Microbiology* Academic Pr.; Tortora, et al. (2000) *Microbiology: An Introduction* including Microbiology Place™ Website, Student Tutorial CD-ROM, and Bacteria ID CD-ROM (7th ed.), Benjamin/Cummings; Demain, et al. (eds. 1999) *Manual of Industrial Microbiology and Biotechnology* (2d ed.) Amer. Soc. Microbiol.; Flint, et al. (eds. 1999) *Principles of Virology: Molecular Biology, Pathogenesis, and Control* Amer. Soc. Microbiol.; Murray, et al. (ed. 1999) *Manual of Clinical Microbiology* (7th ed.) Amer. Soc. Microbiol.; Burlage, et al. (eds. 1998) *Techniques in Microbial Ecology* Oxford Univ. Press; Forbes, et al. (1998) *Bailey & Scott's Diagnostic Microbiology* (10th ed.) Mosby; Schaechter, et al. (ed. 1998) *Mechanisms of Microbial Disease* (3d ed.) Lippincott, Williams & Wilkins; Tomes (1998) *The Gospel of Germs: Men, Women, and the Microbe in American Life* Harvard Univ. Pr.; Snyder and Champness (1997) *Molecular Genetics of Bacteria* Amer. Soc. Microbiol., ISBN: 1555811027; Karlen (1996) *MAN AND MICROBES: Disease and Plagues in History and Modern Times* Touchstone Books; and Bergey (ed. 1994) *Bergey's Manual of Determinative Bacteriology* (9th ed.) Lippincott, Williams & Wilkins.

B. General Methods for Handling Bacteriophage

General methods for handling bacteriophage are well known, see, e.g., Snustad and Dean (2002) *Genetics Experiments with Bacterial Viruses* Freeman; O'Brien and Aitken (eds. 2002) *Antibody Phage Display: Methods and Protocols* Humana; Ring and Blair (eds. 2000) *Genetically Engineered Viruses* BIOS Sci. Pub.; Adolf (ed. 1995) *Methods in Molecular Genetics: Viral Gene Techniques* vol. 6, Elsevier; Adolf (ed. 1995) *Methods in Molecular Genetics: Viral Gene Techniques* vol. 7, Elsevier; and Hoban and Rott (eds. 1988) *Molec. Biol. of Bacterial Virus Systems* (Current Topics in Microbiology and Immunology No. 136) Springer-Verlag.

C. General Fundamentals of Biotechnology, Principles and Methods

General fundamentals of biotechnology, principles and methods are described, e.g., in Alberts, et al. (2002) *Molecular Biology of the Cell* (4th ed.) Garland; Lodish, et al. (1999) *Molecular Cell Biology* (4th ed.) Freeman; Janeway, et al. (eds. 2001) *Immunobiology* (5th ed.) Garland; Flint, et al. (eds. 1999) *Principles of Virology: Molecular Biology, Pathogenesis, and Control*, Am. Soc. Microbiol.; Nelson, et al. (2000) *Lehninger Principles of Biochemistry* (3d ed.) Worth; Freshney (2000) *Culture of Animal Cells: A Manual of Basic Technique* (4th ed.) Wiley-Liss; Arias and Stewart (2002) *Molecular Principles of Animal Development*, Oxford University Press; Griffiths, et al. (2000) *An Introduction to Genetic Analysis* (7th ed.) Freeman; Kierszenbaum (2001) *Histology and Cell Biology*, Mosby; Weaver (2001) *Molecular Biology* (2d ed.) McGraw-Hill; Barker (1998) *At the Bench: A Laboratory Navigator* CSH Laboratory; Branden and Tooze (1999) *Introduction to Protein Structure* (2d ed.), Garland Publishing; Sambrook and Russell (2001) *Molecular Cloning: A Laboratory Manual* (3 vol., 3d ed.), CSH Lab. Press; Scopes (1994) *Protein Purification: Principles and Practice* (3d ed.) Springer Verlag; Simpson, et al. (eds. 2009) Basic Methods in Protein Purification and Analysis: A Laboratory Manual, CSHL Press, NY, ISBN 978-087969868-3; Friedmann and Rossi (eds. 2007) Gene Transfer: Delivery and Expression of DNA and RNA, A Laboratory Manual, CSHL Press, NY, ISBN 978-087969764-8; Link and LaBaer (2009) *Proteomics: A Cold Spring Harbor Laboratory Course Manual, CSHL Press, NY, ISBN* 978-087969793-8; and Simpson (2003) Proteins and Proteomics: A Laboratory Manual, CSHL Press, NY, ISBN 978-087969554-5, Other references directed to bioinformatics include, e.g., Mount (2004) Bioinformatics: Sequence and Genome Analysis (2d ed.), CSHL Press, NY, ISBN 978-087969687-0; Pevsner (2009) Bioinformatics and Functional Genomics (2d ed.) Wiley-Blackwell, ISBN-10: 0470085851, ISBN-13: 978-0470085851; Lesk (2008) Introduction to Bioinformatics (3d ed.) Oxford Univ. Press, ISBN-10: 9780199208043, ISBN-13: 978-0199208043; Zvelebil and Baum (2007) Understanding Bioinformatics, Garland Science, ISBN-10: 0815340249, ISBN-13: 978-0815340249; Baxevanis and Ouellette (eds. 2004) Bioinformatics: A Practical Guide to the Analysis of Genes and Proteins (3d ed.) Wiley-Interscience; ISBN-10: 0471478784, ISBN-13: 978-0471478782; Gu and Bourne (eds. 2009) Structural Bioinformatics (2d ed.), Wiley-Blackwell, ISBN-10: 0470181052, ISBN-13: 978-0470181058; Selzer, et al. (2008) Applied Bioinformatics: An Introduction, Springer, ISBN-10: 9783540727996, ISBN-13: 978-3540727996; Campbell and Heyer (2006) Discovering Genomics, Proteomics and Bioinformatics (2d ed.), Benjamin Cummings, ISBN-10: 9780805382198, ISBN-13: 978-0805382198; Jin Xiong (2006) Essential Bioinformatics, Cambridge Univ Press, ISBN-10: 0521600820, ISBN-13: 978-0521600828; Krane and Raymer (2002) Fundamental Concepts of Bioinformatics, Benjamin Cummings, ISBN-10: 9780805346336, ISBN-13: 978-0805346336; He and Petoukhov (2011) Mathematics of Bioinformatics: Theory, Methods and Applications (Wiley Series in Bioinformatics), Wiley-Interscience, ISBN-10: 9780470404430, ISBN-13: 978-0470404430; Alterovitz and Ramoni (2011) Knowledge-Based Bioinformatics: From analysis to interpretation, Wiley, ISBN-10: 9780470748312, ISBN-13: 978-0470748312; Gopakumar (2011) Bioinformatics: Sequence and Structural Analysis, Alpha Science Intl Ltd., ISBN-10: 184265490X, ISBN-13: 978-1842654903; Barnes (ed. 2007) Bioinformatics for Geneticists: A Bioinformatics Primer for the Analysis of Genetic Data (2d ed.) Wiley, ISBN-10: 9780470026199, ISBN-13: 978-0470026199; Neapolitan (2007) Probabilistic Methods for Bioinformatics, Kaufmann Publishers, ISBN-10: 0123704766, ISBN-13: 978-0123704764; Rangwala and Karypis (2010) Introduction to Protein Structure Prediction: Methods and Algorithms (Wiley Series in Bioinformatics), Wiley, ISBN-10: 0470470593, ISBN-13: 978-0470470596; Ussery, et al. (2010) Computing for Comparative Microbial Genomics: Bioinformatics for Microbiologists (Computational Biology), Springer, ISBN-10: 9781849967631, ISBN-13: 978-1849967631; and Keith (ed. 2008) Bioinformatics: Volume I: Data, Sequence Analysis and Evolution (Methods in Molecular Biology), Humana Press, ISBN-10: 9781588297075, ISBN-13: 978-1588297075.

The following references provide additional guidance for fusion and chimeric proteins: Hammarstrom, et al. (2001) Protein Science 11:313-321; Harrison (1999) InNovations 11:4-7; Banerjee and Padmanabhan WO/2010/125588.

D. Mutagenesis; Site Specific, Random, Shuffling

Based upon the structural and functional descriptions provide herein, homologs and functional variants can be generated. Segments with penetration functions can be found by structural homology. Phage tail genes are typically found in particular gene arrangements, and other entities found in the corresponding arrangements can be tested for cell wall degrading function. These may also serve as the starting points to screen for variants of the structures, e.g., mutagenizing such structures and screening for those which have desired characteristics, e.g., broader substrate specificity. Standard methods of mutagenesis may be used, see, e.g., Johnson-Boaz, et al. (1994) Mol. Microbiol. 13:495-504; U.S. Pat. Nos. 6,506,602, 6,518,065, 6,521,453, 6,579,678.

Membrane transfer segments can be similarly identified, and prevalent or specific target motifs can be screened for receptor domains which specifically interact. Targets can be surface expressed proteins, carbohydrate, or lipid containing structures found on the various target strains. Mutagenesis can be used to broaden binding selectivity or increase stability of segments or the entire construct, deletion strategies may eliminate extraneous segments.

The components of the Gram-positive bacteria cell wall can be shared with components of the Gram-negative cell wall, or with other mycobacteria or spores. Other phage derived activities can be combined to penetrate more complex Gram-negative cell wall structures if necessary. In particular, multiple catalytic segments can be used to provide multiple activities, which can function synergistically within a single construct or when combined with another therapeutic, e.g., antibiotic or antimicrobial.

A targeting moiety can increase a local concentration of an active moiety, but a linker of appropriate length may also increase the number of wall degrading events locally. Thus, linkers compatible with the target and cell wall degrading segment, or of appropriate length, can be used to increase the cell wall penetration activity leading to stasis or killing of target bacteria.

Phage have been selected to survive outside of cells, often under biologically inhospitable conditions. Thus, the structures are likely to be particularly hardy and robust, and resistant to the environmental conditions which might otherwise inactivate enzymatic or catalytic entities. Bacteria which live in inhospitable environments, e.g., extreme environments of temperature, salt, oxidizing or reactive extremes, high pressure, etc., are targeted by phage which are particularly adapted to survive those conditions. Polypeptides derived from these phage are likely to be more stable in various purification processes, storage, and pharmacological conditions of use.

E. Screening

Screening methods can be devised for evaluating mutants or new candidate muralytic segments. A purified preparation of phage particles can be screened for presence of such gene products on the phage structure.

Muralytic activity screens can use crude bacteria cultures, isolated bacterial cell wall components, peptidoglycan preparations, synthetic substrates, or purified reagents to determine the affinity and number of substrate sites on target cells. Penetration or wall degrading assays can be incorporated to evaluate integrity of the outer membranes of target strains, lawn inhibition assays, viability tests of cultures, activity on cell wall preparations or other substrates, or release of components (e.g., sugars, amino acids, polymers) of the cell wall upon muralytic action. Amidase activity may be measured by release of soluble N-acetyl hexose amines (e.g., modified Morgan-Elson reaction) or endopeptidase activity by assay for free amino groups (L-alanine for ala-gly endopeptidases, L-glycine for gly-gly endopeptidases) using a DNFB assay), all three of these assays based on Petit et al. (1966) Biochemistry 5:2764-76. Gly-gly endopeptidase activity can also be measured as the release of free amino groups from N-acetylated hexaglycine (acetyl-Gly6), see Kline, et al. (1994) Anal. Biochem. 217:329-331.

Linkers can be tested to compare the effects on membrane transfer or degradation, or to compare the activities of various orientations of the active fragments. Panels of targets (e.g., Gram-negative, Gram-positive, mycobacteria and spores) can be screened using cell wall degrading fragments to determine which fragments on a broader or narrower spectrum of targets.

One method to test for a cell wall degrading activity is to treat phage with mild detergents or denaturants to release proteins associated with the virion. These proteins are further tested for wall degrading or muralytic activity on bacterial cells. Another method is to determine cell wall degradation activity or lysis from without (LO) on a phage resistant host. A third method to assess wall degrading or muralytic activity associated with phage structural component is to perform Zymogram assays, e.g., where a pure phage preparation is electrophoresed on SDS-polyacrylamide gel incorporating autoclaved host cells. Proteins on the gels are allowed to renature in situ and then act upon the cell wall components giving rise to clear "muralytic" zones when the rest of the gel stains blue with methylene blue dye. See, e.g., Lepeuple, et al, (1998) *Appl. Environ. Microbiol.* 64:4142-428. The clear zones are visualized and the protein band from each zone is eluted. The protein can be identified, e.g., by N-terminal sequencing or by Mass spectrometry. The coding sequence for the degrading protein can then be isolated.

XII. Isolation of Nucleic Acids Encoding MTDs and/or Muralytic Domains

Further provided are nucleic acids that encode the cell wall degrading or membrane transfer domains. Such polynucleotides encode muralytic proteins described herein, including proteins with CHAP domains (particularly C terminal CHAP domains) and others with cell wall degrading activity.

Nucleic acids that encode cell wall degrading polypeptides are relevant to the nucleic acid embodiments of the invention. These nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). Besides synthetic methodologies, a wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc.; Sambrook et al. (1989) *Molecular Cloning—A Laboratory Manual* (2nd ed.) Vol. 1-3, Cold Spring Harbor Laboratory, Cold Spring Harbor Press; *Current Protocols in Molecular*

*Biology*, Ausubel et al., eds., Current Protocols (Greene Publishing Associates, Inc. and John Wiley & Sons, Inc., 1994 Supplement); Cashion et al., US5017478; and Carr, European Patent No. 0246864.

A DNA that encodes a cell wall degrading polypeptide can be prepared by a suitable method described above, including, e.g., cloning and restriction of appropriate sequences with restriction enzymes. Nucleic acids encoding cell wall degrading polypeptides can be isolated by routine cloning methods. An exemplary nucleotide sequence of a cell wall degrading polypeptide, e.g., in Accession Number YP_024486, can be used to design probes that specifically hybridize to a gene; or to an mRNA, encoding a cell wall degrading protein, in a total nucleic acid sample (e.g., in a Southern or Northern blot). Once the target nucleic acid encoding the cell wall degrading protein is identified, it can be isolated according to standard methods known to those of skill in the art. Further, the isolated nucleic acids can be cleaved with restriction enzymes to create nucleic acids encoding the full-length cell wall degrading polypeptide, or subsequences thereof, e.g., containing subsequences encoding at least a subsequence of a catalytic domain of a cell wall degrading polypeptide. These restriction enzyme fragments, encoding a cell wall degrading polypeptide or subsequences thereof, can then be ligated, for example, to produce a nucleic acid encoding a cell wall degrading polypeptide.

Similar methods can be used to generate appropriate cell wall binding fragments or linkers between fragments.

A nucleic acid encoding an appropriate polypeptide, or a subsequence thereof, can be characterized by assaying for the expressed product. Assays based on the detection of the physical, chemical, or immunological properties of the expressed polypeptide can be used. For example, one can identify a cell wall degrading polypeptide by the ability of a polypeptide encoded by the nucleic acid to degrade or digest bacterial cells, e.g., as described herein Also, a nucleic acid encoding a desired polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding a desired polypeptide, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired polypeptide or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the cell wall degrading polypeptide or a polypeptide subsequence thereof by site-directed mutagenesis. The plasmid containing a cell wall degrading polypeptide-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al. (1987) U.S. Pat. No. 4,683,202*; PCR Protocols A Guide to Methods and Applications* (Innis et al., eds) Academic Press Inc. (1990); Arnheim & Levinson (Oct. 1, 1990) *C&EN* 36-47*; The Journal Of NIH Research* (1991) 3: 81-94; Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding cell wall degrading polypeptides can be amplified using PCR primers based on the sequence of the identified polypeptides.

Other physical properties, e.g., of a recombinant cell wall degrading polypeptide expressed from a particular nucleic acid, can be compared to properties of known desired polypeptides to provide another method of identifying suitable sequences or domains, e.g., of the cell wall degrading proteins that are determinants of bacterial specificity, binding specificity, and/or catalytic activity. Alternatively, a cell wall degrading polypeptide encoding nucleic acid or recombinant cell wall degrading polypeptide gene can be mutated, and its role as a cell wall degrading polypeptide, or the role of particular sequences or domains established by detecting a variation in bacterial "lysis" normally enhanced by the unmutated, naturally-occurring, or control cell wall degrading polypeptide. Those of skill will recognize that mutation or modification of cell wall degrading polypeptides of the invention can be facilitated by molecular biology techniques to manipulate the nucleic acids encoding the polypeptides, e.g., PCR. Other mutagenesis or gene shuffling techniques may be applied to the functional fragments described herein, including wall degrading activities, wall binding properties, or linker features compatible with chimeric constructs.

Functional domains of newly identified cell wall degrading polypeptides can be identified by using standard methods for mutating or modifying the polypeptides and testing them for activities such as acceptor substrate activity and/or catalytic activity, as described herein. The sequences of functional domains of the various cell wall degrading proteins can be used to construct nucleic acids encoding or combining functional domains of one or more cell wall degrading polypeptides. These multiple activity polypeptide fusions can then be tested for a desired bacteriostatic or bacteriolytic activity. Particular examples of sources for cell wall degrading polypeptides include prophage sequences, including incomplete remnants of functional phage genomes, or pyocin-like structures, including particles derived from phage-like genetic segments, e.g., deletion or mutated genetic remnants of phage remaining in the DNA of a bacterium.

Nucleic acids encoding cell wall degrading polypeptides can be identified by alignment and comparison with known nucleic acid or amino acid sequences of cell wall degrading polypeptides, e.g., to determine the amount of sequence identity between them. This information can be used to identify and select polypeptide domains that confer or modulate cell wall degrading polypeptide activities, e.g., target bacterial or binding specificity and/or degrading activity based on the amount of sequence identity between the polypeptides of interest. For example, domains having sequence identity between the cell wall degrading polypeptides of interest, and that are associated with a known activity, can be used to construct polypeptides containing that domain and other domains, and having the activity associated with that domain (e.g., bacterial or binding specificity and/or wall degrading activity). Similar strategies may be applied to isolate bacterial SH3 domains which bind to cell wall structures, peptidoglycan recognizing proteins (PGRPs), phage tail "muralytic" polypeptides, or to linkers for spacing between domains.

XIII. Expression of Desired Polypeptides in Host Cells

The proteins described herein can be expressed in a variety of host cells, including *E. coli*, other bacterial hosts, and yeast. The host cells can be microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus, Staphylococcus*, and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*. Eukaryotic cells, e.g., CHO cells, can also be used for production.

Once expressed in a host cell, the cell wall degrading polypeptides can be used to prevent growth or kill target bacteria. In some embodiments, the P225 polypeptide (SEQ ID NO:9) is used to decrease growth of a Gram-negative bacterium. In some embodiments, the protein is used to decrease growth of a *Pseudomonas*, e.g., *Pseudomonas aeruginosa*, bacterium. Fusion constructs combining such fragments can be generated, including fusion proteins comprising a plurality of wall degrading activities, including both peptidase and amidase catalytic activities (which cleave both gly-gly and gly-ala linkages).

Typically, a polynucleotide that encodes the cell wall degrading polypeptides is placed under the control of a promoter that is functional in the desired host cell. An extremely wide variety of promoters is well known, and can be used in expression vectors of the invention, depending on the particular application. Ordinarily, the promoter selected depends upon the cell in which the promoter is to be active. Other expression control sequences such as ribosome binding sites, transcription termination sites, etc., can be included. Constructs that include one or more of these control sequences are termed "expression cassettes." Accordingly, the invention provides expression cassettes into which the nucleic acids that encode fusion proteins, e.g., combining a cell wall degrading fragment with an outer membrane binding fragment, are incorporated for expression in a desired host cell.

Expression control sequences that are suitable for use in a particular host cell can be obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al. (1981) *Nature* 292: 128). A bacteriophage T7 promoter is used in various examples, though one of skill will recognize that the particular promoter system is not critical to the invention.

For expression of cell wall degrading polypeptides in prokaryotic cells other than *E. coli*, a promoter that functions in the particular prokaryotic production species is used. Such promoters can be obtained from genes that have been cloned from the species, or heterologous promoters can be used. For example, the hybrid trp-lac promoter functions in *Bacillus* in addition to *E. coli.*

Hyper-expression of proteins can result in inclusion body formation. The stronger the promoter, the higher is the protein yield per cell, and in some cases, a medium strength promoter results in higher yield of soluble protein compared to a strong promoter. Some examples include T7 promoter, arabinose promoters, T5 and hybrid promoters, etc. Moreover, some toxic protein has been found to be difficult to express due to leaky expression in bacterial cells. Such leaky expression can be avoided by use of promoters that are strongly regulated like arabinose promoters. See, e.g., Correa and Oppezzo (2011) Biotechnol. J. 6:715-730 and Alakomi (2007) "Weakening of the Gram-negative bacterial outer membrane: A tool for increasing microbiological safety" thesis, Univ Helsinki, June 2007.

A ribosome binding site (RBS) is conveniently included in the expression cassettes of the invention. An exemplary RBS in *E. coli* consists of a nucleotide sequence 3-9 nucleotides in length located 3-11 nucleotides upstream of the initiation codon (Shine and Dalgarno (1975) *Nature* 254:34; Steitz (1979) *In Biological regulation and development: Gene expression* (ed. R. F. Goldberger), vol. 1, p. 349, Plenum Publishing, NY).

For expression of proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al. (1987) *Gene* 61:265-275. For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous polypeptides slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the desired polypeptide. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

The construction of polynucleotide constructs generally requires the use of vectors able to replicate in bacteria. A plethora of kits are commercially available for the purification of plasmids from bacteria (see, e.g., EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a polypeptide, necessary for the survival or growth of transformed host cells grown in a selective culture medium. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill.

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., Ylp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

Expression vectors can be introduced into a chosen host cell using standard methods known to those of skill in the art. For example, the expression vectors can be introduced into prokaryotic cells, including *E. coli*, by calcium chloride transformation, and into eukaryotic cells by calcium phosphate treatment or electroporation.

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The various polypeptides of the invention can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al. (1984) *Bio/Technology* 2:800; Schoner et al. (1985) *Bio/Technology* 3:151). In embodiments in which the polypeptide is secreted, either into the periplasm or into the extracellular medium, the DNA sequence is often linked to a cleavable signal peptide sequence. The signal sequence directs translocation of the fusion polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al. (1985) *Proc. Natl. Acad. Sci. USA* 82:7212; Talmadge et al. (1980) *Proc. Natl. Acad. Sci. USA* 77:3988; Takahara et al. (1985) *J. Biol. Chem.* 260: 2670). In another embodiment, the fusion polypeptides are fused to a subsequence of protein A or bovine serum albumin (BSA), for example, to facilitate purification, secretion, or stability. Affinity methods, e.g., using substrate for the catalytic fragment may be appropriate.

The cell wall degrading polypeptides of the invention can also be further linked to other polypeptide segments, e.g., biofilm depolymerase segments. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series. For certain applications, it may be desirable to cleave extraneous sequence from the fusion polypeptide after purification. This can be accomplished by any of several methods known in the art, including cleavage by cyanogen bromide, a protease, or by Factor $X_a$ (see, e.g., Sambrook et al., supra.; Itakura et al. (1977) *Science* 198: 1056; Goeddel et al. (1979) *Proc. Natl. Acad. Sci. USA* 76:106; Nagai et al. (1984) *Nature* 309:810; Sung et al. (1986) *Proc. Natl. Acad. Sci. USA* 83:561). Cleavage sites can be engineered into the gene for the fusion polypeptide at the desired point of cleavage.

More than one recombinant polypeptide may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al (1989) *Biotechnology* 7:698-704. In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

XIV. Purification of Desired Polypeptides

A crude cellular extract containing the expressed intracellular or secreted polypeptides described herein can be used in the methods of the present invention.

The polypeptides can also be purified according to standard procedures of the art, including ammonium sulfate precipitation, affinity columns, column chromatography, gel electrophoresis and the like (see, generally, R. Scopes (1982) *Protein Purification*, Springer-Verlag, N.Y., Deutscher (1990) *Methods in Enzymology Vol.* 182*: Guide to Protein Purification*., Academic Press, Inc. N.Y.). Because the degrading segments, at least, derive from phage proteins selected for stability, purification can involve denaturation of contaminating materials. Substantially pure compositions are typically about 70, 75, 80, 85, 90, 92, 95, 98 to 99% or higher homogeneous. The purified polypeptides can also be used, e.g., as immunogens for antibody production, which antibodies may be used in immunoselection purification methods.

To facilitate purification of the polypeptides of the invention, the nucleic acids that encode them can also include a coding sequence for an epitope or "tag" for which an affinity binding reagent is available, e.g., a purification tag. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the polypeptides of the invention, and corresponding detection systems are known to those of skill in the art, and several are commercially available (e.g., FLAG, Kodak, Rochester N.Y.). Another example of a suitable tag is a polyhistidine sequence, which is capable of binding to metal chelate affinity ligands. Typically, six adjacent histidines (SEQ ID NO:24) are used, although one can use more or fewer than six. Suitable metal chelate affinity ligands that can serve as the binding moiety for a polyhistidine tag include nitrilo-tri-acetic acid (NTA) (Hochuli (1990) Genetic Engineering: Principles and Methods, J. K. Setlow, Ed., Plenum Press, NY; commercially available from Qiagen (Santa Clarita, Calif.)). Purification tags also include maltose binding domains and starch binding domains. Purification of maltose binding domain proteins is known to those of skill in the art.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill will recognize that certain modifications can be made to the catalytic or functional domains of the polypeptide without diminishing their biological activity. Some modifications can be made to facilitate the cloning, expression, or incorporation of the catalytic domain into a fusion polypeptide. Such modifications are well known to those of skill in the art and include, for example, the addition of codons at either terminus of the polynucleotide that encodes the catalytic domain, e.g., a methionine added at the amino terminus to provide an initiation site, or additional amino acids (e.g., poly His) placed on either terminus to create conveniently located restriction enzyme sites or termination codons or purification sequences.

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes.

XV. Examples

Example 1

GP36 Enzymatic Test Construct

A. Muralytic Domain Construct

We isolated the ORF36 sequence from *Pseudomonas* phage P134 (SEQ ID NO: 1). The translation product is shown as SEQ ID NO:2. Based on analysis of the sequence, a murein degrading catalytic domain fragment was identified spanning amino acids 737-875 of SEQ ID NO:2. An expression vector was constructed with a promoter and adjacent initiation codon linked to amino acid 683, so that the nucleic acid construct encodes amino acids 683-898. See SEQ ID NO: 5, which is translated as SEQ ID NO: 6. This segment was designated the GP36 CD fragment.

A sequence was added (thereby removing the termination codon from the end of GP36) to provide an extension of 13 amino acids comprising a 6 His (SEQ ID NO:24) purification tag (for purification on a Nickel column). The construct results in a polypeptide having SEQ ID NO: 7.

The expression construct was introduced into *E. coli*, production of protein was induced, and cells harvested. The cell pellets were processed to isolate the protein, and purified using affinity chromatography over Ni-NTA resin using standard techniques. The protein was analyzed to be greater than 95% pure by SDS-PAGE.

B. Bacterial Killing Assay

As indicated above, the bacterial outer membrane in a Gram-negative bacteria prevents access to the peptidoglycan from the external environment of a cell, but the outer membrane is susceptible to agents that compromise membrane integrity. *Pseudomonas aeruginosa* cells treated with chloroform (which compromises the outer membrane), then with purified GP36 CD fragment. The GP36 CD fragment resulted in a rapid, concentration-dependent reduction in OD (lysis of the bacteria). Further tests and controls were performed to confirm activity, using time course of killing and titration of amount of GP36 CD. Bacterial lysis depended upon the chloroform treatment, and confirmed that the muralytic domain can kill the Gram-negative target once it reaches the peptidoglycan layer.

C. Bacterial Targets

As indicated above, the peptidoglycan layer in most Gram-negative bacteria is relatively thin. The GP36 CD construct was tested on the peptidoglycan of different clinically relevant species of Gram-negative target bacteria. Similar experiments were performed on *Acinetobacter baumanii, Klebsiella pneumoniae, E. coli, Salmonella typhimu-*

*rium, Salmonella gallinarum, Salmonella enteritidis*, and *Salmonella dublin*. The GP36 CD similarly resulted in a rapid, concentration-dependent lysis of chloroform treated bacteria of all tested species.

Example 2

Membrane Transfer Domains

A. Chimera Comprising Muralytic Domain and Membrane Transfer Domain

To access the peptidoglycan layer in a normal Gram-negative bacterial target, a physiologically compatible means for penetrating the bacterial outer membrane barrier was considered. In particular, the penetrating activity must be specific for the bacterial outer membrane while not having significant negative effect on eukaryotic cells.

The GP36 CD enzymatic segment was linked to the membrane transfer domain derived from the human bacterial permeability increasing (BPI) protein. The human BPI nucleic acid sequence is NM_001725.2 (see SEQ ID NO: 3), which encodes the protein sequence BAG37729 (see SEQ ID NO: 4). The construct was designed with a 22 amino acid N-terminus extension including the poly-His (for purification), followed by residues 683-898 of GP36, linked via three arginine residues to amino acids 16-39 of the BPI TMD segment (SEQ ID NO: 4), followed by an additional 3 C-terminal arginine residues. TMD is the designation for the segment with membrane permeating activity, e.g., the transmembrane domain. The polynucleotide construct is designated SEQ ID NO: 8, which encodes the polypeptide designated P225 (SEQ ID NO: 9).

As described above, the expression construct was introduced into *E. coli*, production of protein was induced, and the cells harvested. The cell pellets were processed to isolate the protein, which was mostly located in inclusion bodies. The protein was solubilized, and the product was purified using Ni-NTA column chromatography. The protein was greater than 95% pure by SDS-PAGE.

B. Bacterial Killing Assay

*Pseudomonas aeruginosa* cells were exposed to the purified P225, which resulted in rapid, concentration dependent OD reduction (i.e., bacterial lysis) in the absence of additional permeating agents (e.g., chloroform). Further tests and controls were performed to confirm activity, titrating amount of protein at a time point of one hour. Bacterial killing was observed using a different CFU reduction assay. The killing of live Gram-negative bacteria demonstrates that the BPI TMD can successfully provide the GP36 enzymatic domain access to the peptidoglycan layer inside the bacterial outer membrane.

C. Other Bacterial Targets

The P225 construct was tested for activity on the peptidoglycan of different clinically relevant species of Gram-negative target bacteria. Similar experiments were performed on additional strains of *Pseudomonas aeruginosa, E. coli, Klebsiella* (which is highly resistant to many antibiotics), and *Acinetobacter baumanii*, all of which were effectively killed.

Example 3

P266 Construct and Biological Activity

SEQ ID NO:10 represents a variant of P225, designated P266 (encoded by SEQ ID NO: 11). The N terminal Met can be removed so that the polypeptide begins with Gly. Relative to P225, P226 has a shorter, 6 N-proximal His (SEQ ID NO:24) tag, and lacks the segment following histidines. This provided a construct having segments: 6×His tag-GP36 CD-RRR-BPI TMD-RRR. The GP36 CD would run from about Gly(9) to Glu(224), the first RRR corresponds to R(225) to R(227), the BPI TMD corresponds to Ala(228) to R(251), and the final RRR corresponds to residues 252-254. The projected molecular weight is about 27.6 kDa, with a pI of about 9.48. This includes the N terminal Met, which can be removed.

Like the P225 construct, P266 was insoluble upon expression in *E. coli* BL21 (DE3) cells after induction with IPTG. The induced cell pellet was resuspended in lysis buffer (50 mM Tris base, 0.1M NaCl, 0.1% TritonX100), and sonicated using a 13 mm probe for 10 minutes. The sonicated cell pellet was centrifuged at 16,000 rpm for 10 minutes and the inclusion bodies pellet collected. The inclusion body pellet was solublized by resuspending the pellet in Buffer A (6M GuHCl, 100 mM $NaH_2PO_4$, 10 mM TrisCl, pH 8.0) and kept rocking for 30 min at room temperature. The ratio of IB: buffer volume was 1 gram wet weight of IB with 40 ml of buffer A. The solubilized proteins were centrifuged at 16,000 rpm for 10 mM and the clear supernatant was collected. Ni-NTA matrix was equilibrated with Buffer B (8M urea, 100 mM $NaH_2PO_4$, 10 mM TrisCl, pH 8.0) with 5 column volumes used for equilibration. The solubilized clear supernatant was loaded on to the equilibrated Ni-NTA column and allowed to pass through in gravity mode and the flow through collected. The column was washed with 10 column volumes of Buffer B to remove impurities and unbound proteins. It was then washed with 10-15 column volumes of Buffer C (8M urea, 100 mM $NaH_2PO_4$, 10 mM TrisCl, pH 6.5). The protein elutions were carried out in Buffer E (8M urea, 100 mM $NaH_2PO_4$, 10 mM TrisCl, pH 4.5). Fractions were collected and analyzed by SDS PAGE. Fractions containing protein of interest in high amounts as seen on SDS PAGE gels were pooled and dialyzed in a stepwise manner.

Dialysis was carried out against a buffer volume ~100 times of the pooled eluate volume (e.g., 10 ml eluate dialized against 1 liter buffer), in three steps, first against 4M Urea in 20 mM sodium phosphate buffer, pH 6.0, for 5 hrs at 4 deg C.; second against 2M urea in 20 mM sodium phosphate buffer, pH 6.0, for 5 hrs at 4 deg C.; and third against 20 mM sodium phosphate buffer, pH 6.0, with 5% sucrose, 5% sorbitol, and 0.2% Tween 80, for 5 hrs at 4 deg C. The sucrose, sorbitol, and Tween80 components help stabilize the protein from aggregation and precipitation. Eluates taken out post dialysis were centrifuged to separate any precipitation. The cleared supernatant was collected and protein content estimated for activity assay. The final product was about 85-95% homogeneous by SDS PAGE with coomassie blue staining and silver staining.

The purified protein was assayed for bacterial killing using a CFU drop assay and typically simultaneously monitored for residual OD600 at the end of 16 hours of treatment with the protein product. Log phase PA01 *Pseudomonas aeruginosa* target cells were resuspended in a suitable buffer at an absorbance of 1.0, which corresponds to about 1E7 cells. The protein was tested at 50 μg in either acetate or glycine buffers. The assays were performed in 20 mM sodium phosphate buffer (pH 6.0), 5% sucrose, 5% sorbitol, and 0.2% Tween80 with either 20 mM sodium acetate (pH 6.0) or 50 mM glycine-NaOH (pH 7.0) at 37° C. for 2 hrs at 200 rpm agitation.

The CFU drop assay in sodium acetate buffer provided about 5 log drop, and in the glycine buffer provided at least 7 logs drop after treatment with the protein. From the residual OD600, the acetate buffer provided about 80% less in comparison to control, while the glycine buffer provided about 95% residual decrease in comparison to control.

The CFU drop assay in glycine buffer (pH 7.0) was evaluated without the sucrose, sorbitol, and tween80 stabilizers in the incubation. The CFU drop without stabilizers was the same with stabilizers in the assay, at least 7 logs drop. In many cases, other stabilizers or additives may be useful or important. These may include materials such as polyols, e.g., sorbitol and related compounds; glycerols, e.g., in the range of 0-10%; sugars, such as sucrose, e.g., in the range of 0-5%; detergents or surfactants such as Triton X100, Brij 35, NP-40, Tween 20, Octylbetaglucoside, Sarkosyl, Tween80, etc., preferably tween80, e.g., in the range of 0.1% to 0.5%; and metal chelators such as EGTA, EDTA, preferably EDTA, e.g., in the range if 50 μM-100 μM.

The biological activity of the P266 was titrated across protein concentration on the PA01 target strain. Both the CFU drop and the residual OD600 progressed with 2 hr incubations as the protein was increased from 5, 10, 25, and 50 μg protein. Under the conditions tested, both by CFU drop and residual OD600, with 50 μg P266 at 37° C. and 2 hr incubation, treatment could kill virtually all cells at 1E6 and 1E7 cells in the assay, but showed much decreased killing with 1E8 or more cells in the assay. Incubation time over the 1-4 hour range did not seem to have dramatic effects on PA01 killing assays.

Testing stability of the P266 at various temperatures, the protein appeared to maintain killing activity after 1 hr exposure to 37°, 42°, and 65° C. The product appears to be relatively heat stable up to 65° C. for an hour.

Testing target killing efficiency, the P266 had substantial killing activity, by both the CFU drop and OD600 drop assays, on *Pseudomonas aeruginosa*, NDM1 plasmid carrying *Klebsiella pneumoniae*, NDM1 plasmid carrying *E. coli, Klebsiella pneumoniae, Acinetobacter baumanii, Salmonella typhimurium, Salmonella infantis*, and *E. coli* isolates. P266 had less killing activity on *Shigella, Proteus mirabilis*, and *Burkholderia thailandensis* isolates using the same conditions and concentrations. Similarly, P266 killing activity on Gram-positive bacterial strains was lower than with *P. aeruginosa*, but could likely be increased with longer incubation or higher concentration. The results show, however, that P266 has a broad range of target bacteria, i.e., broader than the target range for any known phage.

The effect of P266 incubation with human red blood cells was minimal at the highest tested 25 and 50 μg amounts. With 1 hr incubations, red blood cells maintained integrity, e.g., containing hemoglobin, and the cells could be sedimented into pellets. P266 therefore does not disrupt eukaryotic cell membranes, suggesting compatibility with in vivo uses of this protein product.

Example 4

Soluble P266 Variant; P275

P266 is insoluble when expressed in *E. coli*, making production difficult. This insolubility requires protein purification and denaturation to solublize, and refolding can lead to significant losses of active protein. In addition, protein oxidation can further reduce activity.

A variant of P266 was designed to decrease the hydrophobicity in the BPI segment (the 23 amino acid MTD). The aim was to subtly disrupt the folded structure of the protein to expose more of the hydrophobic interior to aqueous solution, e.g., removing the shells of water molecules that form over the hydrophobic patches on the surface of some folded proteins. In particular, a nucleic acid construct was designed to generate a variant protein from the P266, designated P275, with conversions of V232 to E; V234 to D; and 1236 to K. See SEQ ID NO: 12 and 13.

Figure 2:
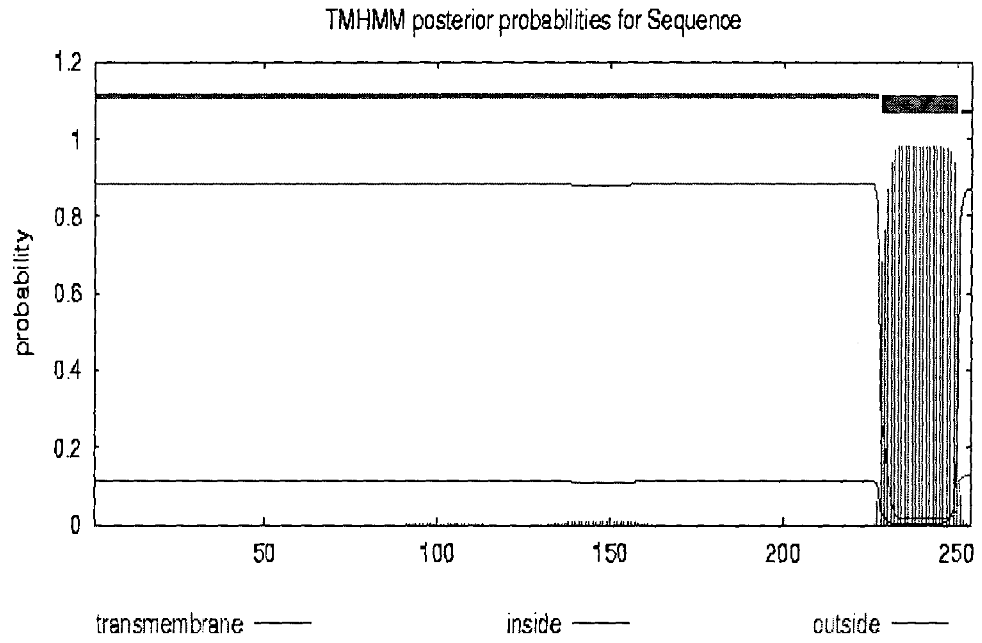
FIG. 2 shows the TMHMM (TransMembrane using Hidden Markov Models) predictions for (A) P266 and (B) P275. While the program does not predict a transmembrane domain for P275, the chimeric protein still effectively crosses the bacterial outer membrane, and kills bacteria at the same level as P266.
Figure 2:
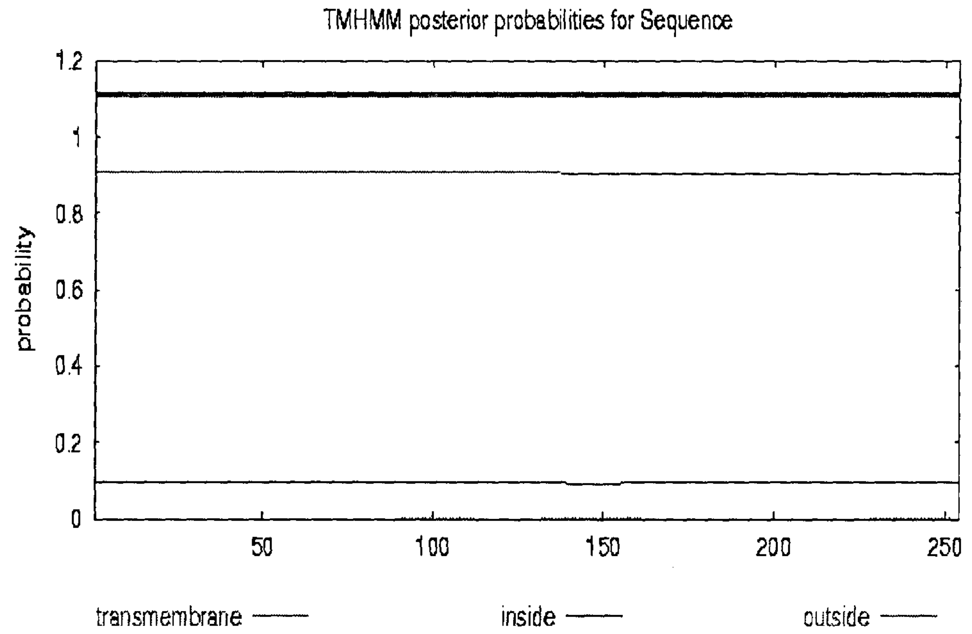
Figure 3:
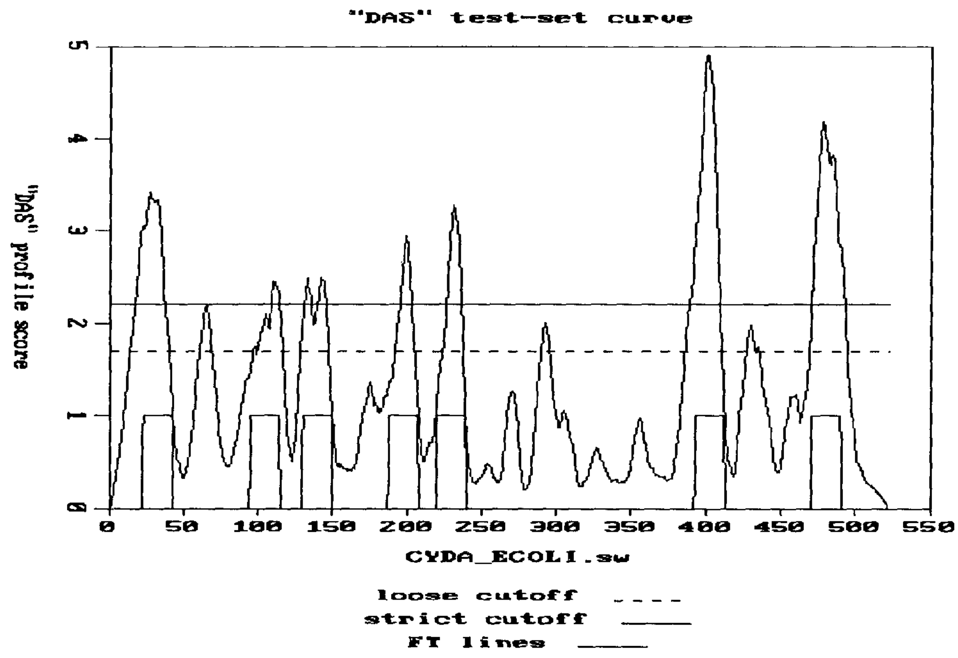
FIG. 3 shows hydrophobicity measurements and transmembrane predictions for the *E. coli* transmembrane protein CydA using (A) DAS plot, (B) TMHMM, and (C) Kyte Doolittle predictions. The DAS plot show that the $6^{th}$ and $7^{th}$ predicted TMDs have relatively high hydrophobicity, indicating that these domains can be targeted for amino acid substitution.
Figure 3:
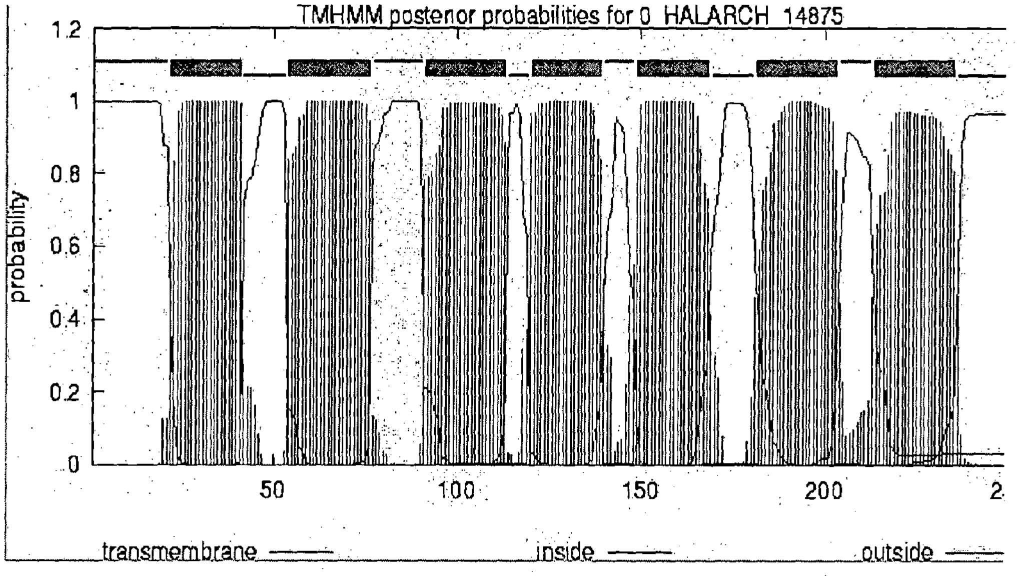
Figure 3:
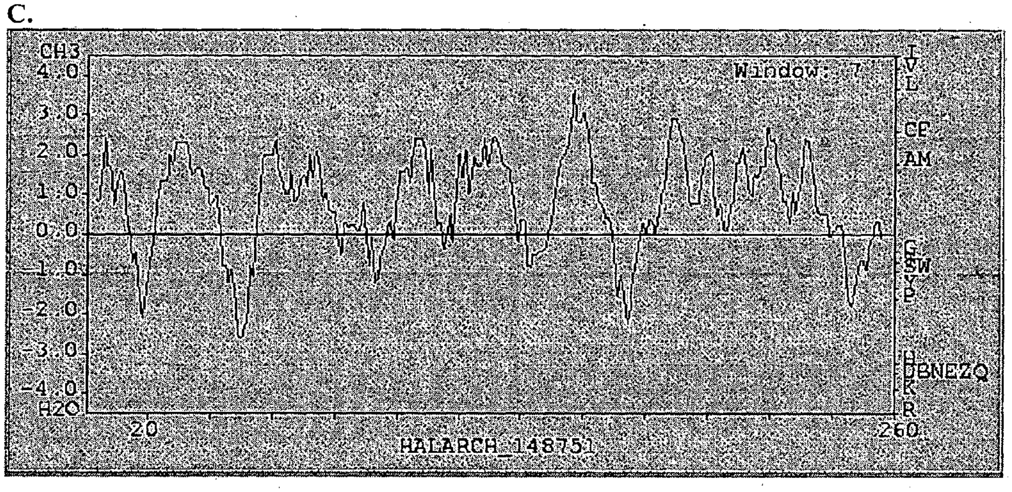

FIG. 1 shows a comparison of DAS plots of P266 and P275. FIG. 2 shows a comparison of the TMHMM plots of P266 of P275. The relative GRAVY scores for the BPI domain and variants thereof are shown below.

| BPI TMD | GRAVY SCORE |
|---|---|
| Wild Type Sequence (SEQ ID NO:): | |
| ASLMVLVAIGTAVTAAVNPGVVVR (25) | 1.658 |
| Variants (SEQ ID NO:): | |
| ASLMELDAKGTAVTAAVNPGVVVR (26) | 0.667 |
| ASLMKLKARGTAKTAAKNPGKKRR (27) | -1.104 |
| ASLMKLKARGTAKTAAKNPGKVRR (28) | -0.767 |
| ASRMVLVARGTAKTAAVNPGVVRR (29) | 0.237 |

P275 exhibits a number of surprising and unexpected properties. The expression construct was expressed in *E. coli* BL21(DE3) with induction at 37° C., 1 mM IPTG, as was the P266 expression. P275 did not, however, form inclusion bodies, and the majority of the protein product was restricted to the soluble fraction. Moreover, and unexpectedly, the soluble protein did not traverse the bacterial cell membrane to access the peptidoglycan layer (located in the periplasmic space) and kill the Gram-negative *E. coli* production cell host. The results show that MTDs can be manipulated to be soluble when expressed in the cell but not capable of traversing the bacterial cell membrane. The manipulated MTD, however, retains the function of allowing the construct to traverse the outer membrane of a Gram negative bacteria. Thus, the manipulated MTD-muralytic domain chimera can access the sensitive peptidoglyan layer of Gram-negative bacteria.

The soluble P275 product was much simpler to handle in purification and recovery, and provided much higher yields of active protein. The soluble P275 protein was purified on the Ni-NTA column at pH 8.0; eluted with imidazole at pH 4.5, dialyzed to remove imidazole, and reformulated into assay buffer. The P275 induced cell pellet was resuspended in Lysis buffer (50 mM Tris Base, 0.1 M NaCl, 0.1% TritonX100) and sonicated. The sonicated cell pellet was centrifuged 16,000 rpm for 10 min, and the supernatant collected and pH adjusted to 8.0. A Ni-NTA matrix was equilibrated with (50 mM Tris.Cl, pH 8.0) using 5 column volumes. The solubilized protein was loaded on to the equilibrated Ni-NTA column and allowed to pass through. The flow through was collected and passed through the column once again. The column was washed with 10-15 column volumes of 20 mM sodium phosphate buffer, pH 6.5, then washed with 5 column volumes of 20 mM sodium phosphate buffer, pH 4.5. Protein elution was carried with 1M imidazole in 20 mM sodium phosphate buffer, pH 4.5. Eluted fractions were collected and analyzed by SDS PAGE. Fractions containing the protein of interest in high amounts as seen on SDS PAGE gels were pooled and dialyzed. Dialysis was carried out against a buffer volume ~100 times of the pooled eluate volume, three changes against 20 mM sodium phosphate buffer, pH 6.0 each for 5 hrs at 4 deg C.

Eluates taken out post dialysis were centrifuged to separate any precipitation, and the supernatant collected and additives sucrose, sorbitol, and Tween80 were added to a final concentration of 5%, 5%, and 0.2% respectively. Protein content was estimated for activity assays.

The P275 product is soluble and easy to purify, which allows a more cost effective downstream operation avoiding the requirement for denaturing agents, and achieving about 85% purity in a simple process leading to a biologically active product. Moreover, and surprisingly, P275 had a comparable or better activity in a CFU drop assay under standard 50 ug protein amounts at 37° C. with 2 hr incubation times.

Example 5

Effect of Oxidation on Chimeric Proteins (e.g., P275)

P275 was tested to see whether protein oxidation might be affecting biological activity. Two amino acids most prone to oxidation are Cys and Met. P275 has no Cys residues, but the Met may be subject to oxidation. Assay in the presence of methionine or sodium thiosulfate could minimize protein oxidation. When the CFU drop assays were performed on the P275 protein in the presence of 0.05% methionine, or 0.1% sodium thiosulfate, the CFU drop was substantially greater than in the absence of either agent. Thus, a formulation of a chimeric protein as described herein with an agent which reduces oxidation, e.g., methionine, sodium thiosulfate, or ascorbic acid, from the range of 0.001-0.2%, 0.001-0.3% and 1-100 mM respectively, e.g., 0.05%, 0.1% and 5 mM of these agents, can be added to retain biological activity, e.g., in storage or assay conditions where oxidation can occur.

To minimize the oxidation which may occur in the protein, the met residues may be removed/replaced, e.g., by site specific mutagenesis. This is relatively simple and straightforward, as described for alanine scanning mutagenesis. See, e.g., Kristensen, et al. (1997) *J. Biol. Chem.* 272:12978-12983. Substituting one or more Met with another less susceptible amino acids e.g., threonine, minimizes the oxidation effects on the protein construct. The construct can be tested initially for susceptibility to loss of activity due to oxidation before embarking on site-specific mutagenisis.

The following references provide additional guidance for addressing stability issues related to oxidation: Yokota, et al. (2000) J. Pharmaceutical and Biomedical Analysis 24:317-324; Grune, et al. (1997); FASEB J. 11:526-534; Lam, et al. (2003) J. Pharmaceutical Sci. 86:1250-1255; Kenley and Warne (1994) Pharmaceutical Research 11:72-76.

Example 6

Substitution of BPI with Alternative MTDs

Table B lists MTD segments which can be combined with catalytic muralytic segments listed in Table A. In P225, P266, and P275, the catalytic domain is N-proximal to the MTD. The relative positions of the two domains can be reversed with the MTD N-proximal to the catalytic domain. If included, the positively charged segment, e.g., RRR, KKK, NNN, QQQ, or mixtures of these positively charged amino acids, are typically adjacent to the MTD, e.g., to attract the MTD to the negatively charged outer membrane.

Sequences of the appropriate domains are available from GenBank and the literature, and appropriate constructs can be created to produce chimeric expression vectors. Chimeric expression constructs can be generated with various combinations of the domains (e.g., a selected subset of the domains in Tables A and B). Once the combinations are constructed, the expression vectors can be introduced into appropriate expression hosts. Upon expression, the products can be tested with the CFU drop or OD600 drop assays for biological activity on target bacteria. Products with activity can be modified or optimized for activity parameters, protein stability, target specificity, critical residues or boundaries of domains, and other features as shown.

For example, as a substitute for BPI, the membrane translocating domain (MTD) from a *Pseudomonas* phage P134 holin can be used for MTD function with a selected catalytic domain, e.g., the GP36 segment. Described are constructs for an additional 5 alternative MTD segments besides the BPI described above.

Five substituted MTD constructs as described below:

A. 10×His-GP36 CD-RRR-P134 holin MTD-RRR

B. 10×His-GP36 CD-RRR-LPS BP peptide-RRR

C. GP36 CD-T4 phage gp5 beta helix-LE-6×His

D. GP36 CD-S type pyocin OM binding domain-LE-6×His

E. GP36 CD-P22 tail spike-LE-6×His

A. P134 Holin TMD: (SEQ ID NO: 14 and 15)

Phage P134 holin transmembrane domain was derived from the holin gene of phage P134. The MTD from P134 holin was identified based on trans membrane helix prediction programs, DAS, and TMHMM. The 23 aa TMD is cloned C terminal to GP36CD with linker and terminal arginines. The GP36CD-RRR-P134TMD-RRR is cloned as an N terminal 10×His (SEQ ID NO:30) tag. An construct of 804 nucleotides, GP36CD-RRR-P134 holinTMD-RRR with 10×His (SEQ ID NO:30) tag and additional vector sequence derived from vector, is described in SEQ ID NO: 14.

NT 1-66 encode the vector-10×His; residues 1-22 (Met is removed in prokaryotes)

NT 67-714 encode the GP36 muralytic domain; residues 23-238

NT 715-723 encode RRR linker; residues 239-241

NT 724-792 encode the P134 holin MTD; residues 242-264

NT 793-801 encode the C terminal RRR; residues 265-267

NT 802-804 encode termination codon

Highly hydrophobic residues in the P134 MTD to target for modification are shown as underlined residues substituting wild type amino acids in the "variants" below. Wild type residues that can be substituted to increase solubility include Ile243; Leu246, Ala248, Ala249, Val250 Val256, Ile261, and Leu264 (see SEQ ID NO:15). The residues are numbered according to SEQ ID NO: 15, which includes the N-terminal Met which is removed in production. Replacement amino acids will typically be amino acids with side chains having similar size. Examples of substitutions include but are not limited to: Ile to Arg, Asp, Asn, or Lys; Leu to Pro, Arg, or Lys; Val to Asp, Lys, or Arg; and Ala to Lys.

| P134 TMD | GRAVY SCORE |
|---|---|
| Wild Type Sequence (SEQ ID NO:): | |
| EIASLCAAVLTALYVGAQLITLL (31) | 1.774 |
| Variants (SEQ ID NO:): | |
| EIASLCAARPTALYVGAQLITLL (32) | 1.161 |
| ERASLCAARLTALYRGAQLRTLL (33) | 0.235 |

-continued

| P134 TMD | GRAVY SCORE |
|---|---|
| EKASLCKKRRTALYKGAQLDTLL (34) | -0.526 |
| EIASRCAAVLTALYVGAQLNTLK (35) | 0.730 |

B. Lipopolysachharide Binding Protein Peptide (SEQ ID NO: 16 and 17):

A stretch of 30 amino acids involved in binding to LPS of gram negative bacteria was identified and selected as an alternative MTD. See Horwitz, Williams, and Nowakowski (1995) Infection and Immunity 63:522-527. Derived from this report; Protein ID: CAA67226 (AA 106 to 135). This sequence is fused to GP36 catalytic domain (CD) to generate the 825 nucleotide construct which encodes molecule GP36CD-RRR-LBP peptide-RRR. This is cloned with an N terminal histidine tag. The construct is 825 nucleotides, predicted 274 residues (including N terminal Met, which should be removed in prokaryote hosts) Mw: 30.38 kDa, and pI: 9.72.

NT 1-3 is initiation Met, removed in most prokaryote hosts
NT 4-66 encodes the vector segment-10×His; residues 2-22
NT 67-714 encodes the GP36 muralytic domain; residues 23-238
NT 715-723 encodes the RRR linker; residues 239-241
NT 724-813 encodes the LPS BP MTD; residues 242-271
NT 814-822 encodes the RRR linker; residues 272-274
NT 823-825 encodes termination codon The LPS Binding Protein derived MTD is described in SEQ ID NO: 17. The residues which are indicated for replacement to generate a more soluble variant include Val248; Val267; Val269; Phe258; and Phe259.

C. T4 Phage gp5 Beta Helix (SEQ ID NO: 18 and 19):

The C terminal beta helix domain from protein gp5 of phage T4 is reported to be responsible for penetrating the outer membrane of a bacterial cell during infection. See Leiman, et al. (2010) Virology J. 7:355. The gp5 beta helix sequence (187 aa; from NP 049757.1 residues 389-575) is cloned C terminal to GP36CD with a C terminal 6× histidine (SEQ ID NO:24) tag. The construct is 1245 nucleotides; predicted 414 residues with predicted pI/Mw: 5.43/45353.99 with N terminal Met uncleaved.

NT 1-651 encodes the initiation MET and GP36 muralytic domain; residues 1-217
NT 652-657 encodes a KL (generated by restriction enzyme site Hind III); residues 218-219
NT 658-1218 encodes the T4 phage gp5 beta-helix; residues 220-406
NT 1219-1224 encodes a LE (generated by restriction enzyme site XhoI); residues 407-408
NT 1225-1242 encodes 6×His (SEQ ID NO:24); residues 409-414
NT 1243-1245 encodes termination codon D. S Type Pyocin Outer Membrane Translocation (OMT) Domain (SEQ ID NO: 20 and 21):

The outer membrane translocation domain from S type pyocins translocate across the outer membrane of *P. aeruginosa*. See Ling, Saeidi, Rasouliha, and Chang (2010) "A predicted S-type pyocin shows a bactericidal activity against clinical *Pseudomonas aeruginosa* isolates through membrane damage" FEBS Letters 584:3354-3358. The OMT domain (181 residues; see Protein Acc. No. EHS39709, residues 217-397; *P. aeruginosa* MPAO/P1) was cloned C terminal to GP36CD with histidine tag at the C terminus. The construct of 1227 nucleotides encodes 408 amino acids (including the N terminal Met, which is typically removed by prokaryote hosts), which has a predicted pI/Mw: 8.44/44543.37

NT 1-651 encodes the initiation MET and GP36 muralytic domain; residues 1-217
NT 652-657 encodes a KL (generated by Hind III site); residues 218-219
NT 658-1200 encodes the OM translocation domain; residues 220-400
NT 1201-1206 encodes a LE (generated by restriction enzyme site XhoI); residues 401-402
NT 1207-1224 encodes 6×His (SEQ ID NO:24); residues 403-408
NT 1225-1227 encodes termination codon E. P22 Tail Spike Protein (SEQ ID NO: 22 and 23):

The tail spike protein of phage P22 has endorhamnosidase activity capable of modifying O-antigen, hence, compromising the structure of lipopolysaccharide of *Salmonella*. See, e.g., Steinbacher, et al. (1997) "Phage P22 tailspike protein: crystal structure of the head-binding domain at 2.3 A, fully refined structure of the endorhamnosidase at 1.56 A resolution, and the molecular basis of O-antigen recognition and cleavage" J Mol Biol. 267:865-80; and Waseh, et al. (2010) "Orally Administered P22 Phage Tailspike Protein Reduces *Salmonella* Colonization in Chickens: Prospects of a Novel Therapy against Bacterial Infections" PLoS One 5(11): e13904. The *Salmonella* tail spike protein (see Protein ID: NP_059644, amino acids 2-667) was cloned C terminal to GP36CD with histidine tag at the C terminus. The theoretical size is 893 amino acids; pI/Mw: 5.76/96694.40.

NT 1-651 the initiation MET and GP36 muralytic domain; residues 1-217
NT 652-657 encodes a KL (generated by restriction enzyme site Hind III), residues 218-219
NT 658-2655 encodes the P22 tail spike protein domain, residues 220-885
NT 2656-2661 encodes a LE (generated by restriction enzyme site XhoI), residues 886-887
NT 2662-2679 encodes 6×His (SEQ ID NO:24); residues 888-893
NT 2680-2682 encodes termination codon

Example 7

Expression, Purification, and Validation of Chimeric Proteins

The following descriptions are examples of how to prepare and validate the additional chimeric constructs. Buffers, media, times, and other conditions can be modified as will be understood by one of skill in the art of protein expression and design.

Codon optimization for expression in *E. coli* (codon bias), changing the GC content, incorporating alternate fusion tags (e.g., glutathione S-transferase GST), nusA transcription elongation factor, maltose binding protein (MBP), intein, among many possibilities), varying inducer concentrations, temperature, expression with chaperones for improved folding, and different expression hosts can be used to improve expression of the desired constructs.

For example, competent cells of a production host, e.g., *E. coli*, are transformed with the respective plasmid, plated on LB+ampicillin (100 μg/ml) or kanamycin (20 μg/ml), and incubated overnight at 37 deg C. The cultures from plates are scraped into LB+antibiotic, typically liquid, and grown to $OD_{600}$ ~0.8 to 1.0. The cells are then induced with IPTG at 1 mM and incubated at 37 deg C. for 4 hours. The cells are harvested by centrifugation at 8000 rpm for 10 minutes and the pellet stored at −80 deg C.

Where constructs accumulate in inclusion bodies, the induced cell pellet is resuspended in lysis buffer (50 mM Tris base, 0.1 M NaCl, 0.1% TritonX100), and sonicated using a 13 mm probe for 10 minutes. The sonicated cell pellet is centrifuged at 16,000 rpm for 10 minutes and a pellet containing inclusion bodies (IB) is collected. The inclusion body pellet is solubilized by resuspending the pellet in Buffer A (6M GuHCl, 100 mM $NaH_2PO_4$, 10 mM TrisCl, pH 8.0) and kept rocking for 30 mins at room temperature. The ratio of IB: buffer volume is typically 1 gram wet weight of IB with 40 ml of buffer A. The lysate is centrifuged at 16,000 rpm for 10 min and the clear supernatant is collected. A Ni-NTA matrix is equilibrated with Buffer B (8M urea, 100 mM $NaH_2PO_4$, 10 mM TrisCl, pH 8.0) with 5 column volumes used for equilibration. The supernatant from the IB is loaded on to the equilibrated Ni-NTA column and allowed to pass through in gravity mode and the flow through is collected. The column is washed with 10 column volumes of Buffer B to remove impurities and unbound proteins. The column is then washed with 10-15 column volumes of Buffer C (8M urea, 100 mM $NaH_2PO_4$, 10 mM TrisCl, pH 6.5). The attached protein elutions are carried out in Buffer E (8M urea, 100 mM $NaH_2PO_4$, 10 mM TrisCl, pH 4.5). Fractions are collected and analyzed by SDS PAGE. Fractions containing protein of interest in high amounts as seen on SDS PAGE gels are pooled and dialyzed in a stepwise manner. The pooled fractions are subject to dialysis carried out against a buffer volume ~100 times of the pooled eluate volume (e.g., 10 ml eluate dialized against 1 liter buffer). The dialysis is performed first against 4M urea in 20 mM sodium phosphate buffer, pH 6.0, for 5 hrs at 4 deg C.; then secondly against 2M urea in 20 mM sodium phosphate buffer, pH 6.0, 5 hrs at 4 deg C.; and thirdly against 20 mM sodium phosphate buffer, pH 6.0 with 5% sucrose, 5% sorbitol, and 0.2% tween80 for 5 hrs at 4 deg C. Eluates taken out post dialysis are centrifuged to separate any precipitated material. The cleared supernatant is collected and protein content estimated for activity assay.

To verify activity (bacterial cell killing activity) a CFU drop assay can be performed as follows. Bacterial cells are grown in LB broth to absorbance at 600 nm reaches a range of 0.8 to 1.0. Then 1 ml of culture is spun at 13000 rpm for 1 minute and supernatant discarded. The cell pellet is resuspended in one ml of 50 mM Glycine-NaOH buffer (pH 7.0) and cell numbers adjusted to about $1\times10^8$/ml. Test protein is added to 100 μl cells to achieve final concentration of about 50 μg and volume made-up to 200 μl with 20 mM sodium phosphate buffer (pH 6.0) with additives. The protein is incubated with cells at 37 deg C. for 2 hours with 200 rpm agitation, then the samples are log diluted in LB broth and plated on LB agar to quantitate residual CFU. The plates are incubated at 37 deg C. overnight for colonies to grow.

The Metabolic Dye Reduction assay can also be used to determine live cell numbers. The assay is based on the principle that viable cells reduce Iodo-Nitro Tetrazolium (INT), a metabolic indicator dye. Briefly, $1\times10^7$ target cells, e.g., *P. aeruginosa*, in 100 μl volume are mixed with test protein in 100 μl to achieve final concentration of about 50 μg and volume made-up to 200 μl with 20 mM sodium phosphate buffer (pH 6.0) with additives in microtiter plate wells. A cell control is also maintained. Samples are incubated at 37 deg C. with 200 rpm for 2 hour and INT dye (1×) is added to all samples. The microplate is incubated in dark at room temperature for 20 minutes and the absorbance at 492 nm is recorded. 10×INT stock solutions are prepared by dissolving 30 mg Tetrazolium Violet (Loba Chemie, India) in 10 ml of 50 mM Sodium Phosphate buffer, pH 7.5.

Example 8

Detection of Bacterial Cell Binding

In Gram-negative bacteria, the outer membrane (OM) and the peptidoglycan are linked by lipoproteins. The OM includes porins, which allow the passage of small hydrophilic molecules. See, e.g., Cabeen and Jacobs-Wagner (2005) "Bacterial Cell Shape" Nature Revs Microbiology 3:601-610; Nikaido (2003) Microbiol. Mol. Biol. Rev. 67:593-656. The structure and composition of the outermost layer of the cells is reported to be different between different bacteria. On the outer envelope cells may have polysaccharide capsules (see, e.g., Sutherland (1999) Biotechnol. Genet. Eng. Rev. 16:217-29; and Snyder, et al. (2006) Carbohydr. Res. 341:2388-97.) or protein S-layers (Antikainen, et al. (2002) Mol. Microbiol. 46:381-94; Schäffer and Messner (2005) Microbiology. 151:643-51; and Avall-Jääskeläinen and Palva (2005) FEMS Microbiol Rev. 29:511-29), which protect bacteria in unfavourable conditions and affect their adhesion. The basic structure of lipopolysaccharide (LPS), a covalently linked lipid and heteropolysaccharide, is common to all LPS molecules studied, but there are variations depending on bacterial genera, species, and strains. See, e.g., Trent, et al. (2006) J. Endotoxin Res. 12:205-23; Raetz and Whitfield (2002) Ann. Rev. Biochem. 71:635-700; Yethon and Whitfield (2001) Curr. Drug Targets Infect. Disord. 1:91-106; and Yethon and Whitfield (2001) J. Biol. Chem. 276:5498-504.

The chimeric constructs described herein can thus be tested for binding to a target bacteria. Described here are various assays for whether the construct (with MTD) reaches the peptidoglycan layer. SDS-PAGE can be used to detect binding of the protein to cells. For example, $10^7$ cells are treated with a suitable amount of protein for approximately 2 hours. Then the cells are pelleted by centrifugation and the amount of protein in the supernatant is examined on SDS-PAGE and stained. The protein is labeled as adsorbed to cells, if the intensity of the protein before the adsorption to cells is higher than the one after adsorption, the difference is likely to be due to cell binding. Binding can also be detected using, e.g., confocal imaging to detect changes to the bacterial OM upon exposure to a chimeric construct. Fluorescent tags or luciferase can also be used, as will be recognized by one of skill.

INFORMAL SEQUENCE LISTING

SEQ ID NO: 1 (P134 GP36 full length DNA sequence: highly homologous to Gene ID 1482616)

SEQ ID NO: 2 (AA translation of SEQ 1 (GP36); highly homologous to NP877475)

-continued

INFORMAL SEQUENCE LISTING

SEQ ID NO: 3 (*Homo sapiens* cDNA, FLJ96367, highly similar to *Homo sapiens* bactericidal/permeability-increasing protein (BPI), mRNA; GenBank: AK315328.1)

SEQ ID NO: 4 (BPI; unnamed protein product [*Homo sapiens*] GenBank: BAG37729.1)

SEQ ID NO: 5 ( P134 GP36 CD nucleic acid; first CHCl3 test construct)

SEQ ID NO: 6 (24 Kda construct; translation product of SEQ ID NO: 5, 217 amino acids)

SEQ ID NO: 7 [13 aa C terminal extension attached for purification purposes onto 24 Kda]

SEQ ID NO: 8 {encoding chimeric GP36 segment linked to BPI segment; P225}

SEQ ID NO: 9 [linker-GP36 muralytic domain-RRR-BPI TMD-RRR; P225 polypeptide]

SEQ ID NO: 1 (P134 GP36 full length DNA coding sequence: [close homolog to Gene ID 1482616]) Nucleotide sequence of P134 GP36:

```
   1 ATGGCGGAATCGCAACGTGCTTCCCAAGAGCTTGGGATCAACGTCGGACAGGCGCAACTC     60
  61 CAGCCGGGCCAGAGTGCCCGGCGCGGAGTGCGCGACTCCGAGGTCAACTACAGCGGTCCG    120
 121 AGTGTAGGCTCGCAGATTCTCGACGGCATCCTGGGTGCCGGTCAGCAGATCGCTGGCAAA    180
 181 TGGTTCGAGCACAACGTGCAGCAGGAAGTTCTGCGCGGTGAGCGTGCCCGTATGGCCGGC    240
 241 GAGGCTGAGGAGGCAGTAGACAGCAACGTACTGGCCAAACCATTCGTGAAGGGTGGTTGG    300
 301 CGTAAGCAGGACTACCGTATCGCCCAGGCGGACTTCAGCCTGAAGATGCAGCGATTCATC    360
 361 GCCAACAAGGGCCGGGAGATGACTCCCGAGGAGTTCCGCAAGTACCTGTCCCAGGAGGCT    420
 421 ACGCACGTCCTGGACTCGACCGAGGGCATGAACCCCAACGATGCCCTACAGGCGATGGCA    480
 481 CAGCAGCAGAAGGCCGAGGAACAGCTCTTTGGCATGCAGGCTAAGGCGTACATGGATTGG    540
 541 TCCATCGACCAGGCCGCACGGGGCTTCCGCACCCAGGGTAACAGCATCCTGGCCAAGGCC    600
 601 GTACATGCCCAGGCCACCGGCGACGAGCTATCCCGGCAACTCAGCCTGGAAGAGGCCGGC    660
 661 CTGTTCTATACCAACATCATGACCTCCGAGGATATCCCGCTGGAGGTACGTGACAAGGTG    720
 721 GGTATGCAGTTCCTGGCGGCCAGCCTGGACATGAACCAGCGGGGCATCTATGAGGGCCTG    780
 781 CGCGATGCCGGGTTCCTGGACAGTATGTCCTTTGACGACCGGCGTGCGCTCAACGGCCTC    840
 841 TATGAAAAATCGAAGGCACAGACCCGTGCCAAGGAATCGATGGCTACCCTGCGGGCCGAC    900
 901 GCGGACTTCCAGCAGCGGGTGGCCAACGGCGCCATCACAGACCTTGCCGAGGTTGAGGCG    960
 961 TACTCACGAGGCATGGTCGAGGAGGGCCGCTGGAGCGACGCTCAGGCCATCTCGTTCATG   1020
1021 ACCAAGGCCATGACCGGCCTGGGCAACGCTCAGCGCATGCAGGGCATCATGGCGGCCTTG   1080
1081 GAAGCCGGAGACATCAACGCCCTCCACACGCTGGGTACCAACGTCACCGAGGCGCTGGAG   1140
1141 CAGTGGGACAAGATGCAGGCCGCCAACGGCTCAAGCCTGACTGACCGTCTCGTGCAGGGC   1200
1201 ACACAGCTCGGCCTGCGCCTGGGGACCTTCCCCAAGACCTACGGCGAGTCCGTGGGCAGC   1260
1261 GCGGTGCGCATGATCCAGGCCGCCAAGGAAGGCGAGGCAAACCCGGAGCTGGTCAACACG   1320
1321 CTGAACAGCATCTTCGAACAGGTGGCCTCGGCCCAGGAGATCAACCCATCCGCCGGCAAC   1380
1381 GTGATGCTATCCGGCATCCCGGAAGCCGAGCAGGGCGCCGTGGCCTGGGCACTCAAGCAG   1440
1441 ATGAAGATGGGCATCGCACCAGCTCAAGCTCTGCGCGAGTTTAGCGCCAACGCCGAAGTC   1500
1501 GTGAAGCAGATGGACGAGTTCGAGAAAGGCCAGAACACCAAGGCATTCAAGGACAACCTC   1560
1561 GGTAAGCAGGTCAACGACAAGTTCGTGAACAACATCTTCGGTCGAGCCTGGAACATGCTG   1620
1621 ACCGGCGAGAGCGACCTGAGCAACAACGAGGCCGTCCTGAGCATGTATCGCCGGGCGACC   1680
1681 ATCGACGAGGCGAACTGGCTGGCCAGCGACCGCAAGCATGCGGGTCTGCTCACCAGCGAC   1740
1741 ACGGGCCGCGAGGCCCTGCTGGAGATCGCCGCCGCCAACGTGCGTAACCGCACCATCCAG   1800
1801 GTAGGCGAAGGTCGGAACCTGAAGGAAGGGGACCTATTCAGCCGCCGCGATAGCGCGCCG   1860
1861 CTGATCCTGCCTCGCGGCACCACCGCCGAGCAGCTATTCGGGACCAACGACACCGAGACC   1920
1921 ATCGGAACCGTCCTGGCCGAGCAGCACAAGCCGCATGTCGAAGGACTCCTCGGCTACAAG   1980
1981 TCGGTAGTCGCCTTCGAGTACGACCGCACCAGTGGCAGCCTCCTCGCCGTCGAGTACGAC   2040
2041 GAGAACGGTGTGGCCCTGGACCGCACGCGGGTTGATCCCCAGGCAGTCGGCAACGAGGTG   2100
2101 CTCAAGCGCAACGCGGATAAGCTGAATGCGATGCGGGGCGCCGAGTACGGTGCCAACGTC   2160
2161 AAGGTCAGCGGCACGGACATTCGCATGAACGGGGGTAACAGTGCCGGCATGCTGAAGCAG   2220
2221 GACGTGTTCAACTGGCGGAAGGAACTGGCTCAGTTCGAGGCTTACCGAGGGGAGGCGTAT   2280
2281 AAGGATGCCGATGGTTATAGTGTGGGCCTGGGGCATTACCTGGGCAGTGGCAATGCTGGG   2340
2341 GCAGGTACTACAGTCACGCCTGAGCAAGCCGCGCAGTGGTTCGCCGAGGACACCGACCGC   2400
2401 GCACTCGACCAGGGTGTGAGGTTGGCCGACGAGCTGGGCGTTACGAACAATGCCTCTATC   2460
2461 CTGGGATTGGCCGGTATGGCCTTCCAGATGGGCGAAGGACGTGCCCGGCAGTTCCGTAAC   2520
2521 ACCTTCCAGGCGATCAAGGATCGCAACAAGGAAGCCTTCGAGGCTGGTGTGCGAAACAGC   2580
2581 AAGTGGTACACGCAGACGCCCACCGGGGCCGAGGCATTCATCAAGCGCATGGCGCCCCAC   2640
2641 TTCGATACACCGAGTCAAATCGGTGTCGATTGGTACAGCGCCGCAACAGCGGAGTAA      2697
```

SEQ ID NO: 2 (AA translation of SEQ ID NO: 1 (P134 GP36); highly homologous to NP877475)

Amino acid sequence of P134 GP36:

```
  1  MAESQRASQELGINVGQAQLQPGQSARRGVRDSEVNYSGPSVGSQILDGILGAGQQIAGK     60
 61  WFEHNVQQEVLRGERARMAGEAEEAVDSNVLAKPFVKGGWRKQDYRIAQADFSLKMQRFI    120
121  ANKGREMTPEEFRKYLSQEATHVLDSTEGMNPNDALQAMAQQQKAEEQLFGMQAKAYMDW    180
181  SIDQAARGFRTQGNSILAKAVHAQATGDELSRQLSLEEAGLFYTNIMTSEDIPLEVRDKV    240
241  GMQFLAASLDMNQRGIYEGLRDAGFLDSMSFDDRRALNGLYEKSKAQTRAKESMATLRAD    300
301  ADFQQRVANGAITDLAEVEAYSRGMVEEGRWSDAQAISFMTKAMTGLGNAQRMQGIMAAL    360
```

-continued

| INFORMAL SEQUENCE LISTING |
| --- |

```
361  EAGDINALHTLGTNVTEALEQWDKMQAANGSSLTDRLVQGTQLGLRLGTFPKTYGESVGS          420
421  AVRMIQAAKEGEANPELVNTLNSIFEQVASAQEINPSAGNVMLSGIPEAEQGAVAWALKQ          480
481  MKMGIAPAQALREFSANAEVVKQMDEFEKGQNTKAFKDNLGKQVNDKFVNNIFGRAWNML          540
541  TGESDLSNNEAVLSMYRRATIDEANWLASDRKHAGLLTSDTGREALLEIAAANVRNRTIQ          600
601  VGEGRNLKEGDLFSRRDSAPLILPRGTTAEQLFGTNDTETIGTVLAEQHKPHVEGLLGYK          660
661  SVVAFEYDRTSGSLLAVEYDENGVALDRTRVDPQAVGNEVLKRNADKLNAMRGAEYGANV          720
721  KVSGTDIRMNGGNSAGMLKQDVFNWRKELAQFEAYRGEAYKDADGYSVGLGHYLGSGNAG          780
781  AGTTVTPEQAAQWFAEDTDRALDQGVRLADELGVTNNASILGLAGMAFQMGEGRARQFRN          840
841  TFQAIKDRNKEAFEAGVRNSKWYTQTPTGAEAFIKRMAPHFDTPSQIGVDWYSAATAE            898
```

SEQ ID NO: 3 (*Homo sapiens* cDNA, FLJ96367, highly similar to *Homo sapiens* bactericidal/permeability-increasing protein (BPI), mRNA; GenBank: AK315328.1)

```
ORIGIN
   1 aggccttgag gttttggcag ctctggagga tgagagagaa catggccagg ggcccttgca
  61 acgcgccgag atgggcgtcc ctgatggtgc tggtcgccat aggcaccgcc gtgacagcgg
 121 ccgtcaaccc tggcgtcgtg gtcaggatct cccagaaggg cctggactac gccagccagc
 181 aggggacggc cgctctgcag aaggagctga agaggatcaa gattcctgac tactcagaca
 241 gctttaagat caagcatctt gggaagggge attatagctt ctacagcatg gacatccgtg
 301 aattccagct tcccagttcc cagataagca tggtgcccaa tgtgggcctt aagttctcca
 361 tcagcaacgc caatatcaag atcagcggga aatggaaggc acaaaagaga ttcttaaaaa
 421 tgagcggcaa ttttgacctg agcatagaag gcatgtccat ttcggctgat ctgaagctgg
 481 gcagtaaccc cacgtcaggc aagcccacca tcacctgctc cagctgcagc agccacatca
 541 acagtgtcca cgtgcacatc tcaaagagca aagtggggtg gctgatccaa ctcttccaca
 601 aaaaaattga gtctgcgctt cgaaacaaga tgaacagcca ggtctgcgag aaagtgacca
 661 attctgtatc ctccgagctg caaccttatt tccagactct gccagtaatg accaaaatag
 721 attctgtggc tggaatcaac tatggtctgg tggcacctcc agcaaccacg gctgagaccc
 781 tggatgtaca gatgaagggg gagttttaca gtgagaacca ccacaatcca cctccctttg
 841 ctccaccagt gatggagttt cccgctgccc atgaccgcat ggtataccta ggcctctcag
 901 actacttctt caacacagcc gggcttgtat accaagaggc tggggtcttg aagatgaccc
 961 ttagagatga catgattcca aaggagtcca aatttcgact gacaaccaag ttctttggaa
1021 ccttcctacc tgaggtggcc aagaagtttc ccaacatgaa gatacagatc catgtctcag
1081 cctccacccc gccacacctg tctgtgcagc ccaccggcct taccttctac cctgccgtgg
1141 atgtccaggc ctttgccgtc ctccccaact cctccctggc ttccctcttc ctgattggca
1201 tgcacacaac tggttccatg gaggtcagcg ccgagtccga caggcttgtt ggagagctca
1261 agctggatag gctgctcctg gaactgaagc actcaaatat tggccccttc ccggttgaat
1321 tgctgctgga tatcatgaac tacattgtac ccattcttgt gctgcccagg gttaacgaga
1381 aactacagaa aggcttccct ctcccgacgc cggccagagt ccagctctac aacgtagtgc
1441 ttcagcctca ccagaacttc ctgctgttcg gtgcagacgt tgtctataaa tga
```

SEQ ID NO: 4 (BPI; unnamed protein product [*Homo sapiens*] GenBank: BAG37729.1)

```
ORIGIN
  1  mrenmargpc naprwaslmv lvaigtavta avnpgvvvri sqkgldyasq qgtaalqkel
 61  krikipdysd sfkikhlgkg hysfysmdir efqlpssqis mvpnvglkfs isnanikisg
121  kwkaqkrflk msgnfdlsie gmsisadlkl gsnptsgkpt itcsscsshi nsvhvhisks
181  kvgwliqlfh kkiesalrnk mnsqvcekvt nsysselqpy fqtlpvmtki dsvaginygl
241  vappattaet ldvqmkgefy senhhnpppf appvmefpaa hdrmvylgls dyffntaglv
301  ygeagvlkmt lrddmipkes kfrlttkffg tflpevakkf pnmkiqihvs astpphlsvq
361  ptgltfypav dvgafavlpn sslaslflig mhttgsmevs aesdrlvgel kldrlllelk
421  hsnigpfpve lldimnyiv pilvlprvne klqkgfplpt parvqlynvv lqphqnfllf
481  gadvvyk
```

SEQ ID NO: 5 (P134 GP36 nucleic acid; first CHC13 test construct)

```
  1  ATGGGTGTGGCCCTGGACCGCACGCGGGTTGATCCCCAGGCAGTCGGCAACGAGGTGCTC           60
 61  AAGCGCAACGCGGATAAGCTGAATGCGATGCGGGGCGCCGAGTACGGTGCCAACGTCAAG          120
121  GTCAGCGGCACGGACATTCGCATGAACGGGGGTAACAGTGCCGGCATGCTGAAGCAGGAC          180
181  GTGTTCAACTGGCGGAAGGAACTGGCTCAGTTCGAGGCTTACCGAGGGGAGGCGTATAAG          240
241  GATGCCGATGGTTATAGTGTGGGCCTGGGGCATTACCTGGGCAGTGGCAATGCTGGGGCA          300
301  GGTACTACAGTCACGCCTGAGCAAGCCGCGCAGTGGTTCGCCGAGGACACCGACCGCGCA          360
361  CTCGACCAGGGTGTGAGGTTGGCCGACGAGCTGGGCGTTACGAACAATGCCTCTATCCTG          420
421  GGATTGGCCGGTATGGCCTTCCAGATGGGCGAAGGACGTGCCCGGCAGTTCCGTAACACC          480
481  TTCCAGGCGATCAAGGATCGCAACAAGGAAGCCTTCGAGGCTGGTGTGCGAAACAGCAAG          540
541  TGGTACACGCAGACGCCCACCGGGGCCGAGGCATTCATCAAGCGCATGGCGCCCCACTTC          600
601  GATACACCGAGTCAAATCGGTGTCGATTGGTACAGCGCCGCAACAGCGGAGTAA                654
```

SEQ ID NO: 6 (24 Kda construct; translation product of SEQ ID NO: 5, 217 amino acids. N-terminal Net may be removed in a prokaryotic production host, so N-terminus of protein may begin with G.)

```
  1  MGVALDRTRVDPQAVGNEVLKRNADKLNAMRGAEYGANVKVSGTDIRMNGGNSAGMLKQD           60
 61  VFNWRKELAQFEAYRGEAYKDADGYSVGLGHYLGSGNAGAGTTVTPEQAAQWFAEDTDRA          120
121  LDQGVRLADELGVTNNASILGLAGMAFQMGEGRARQFRNTFQAIKDRNKEAFEAGVRNSK          180
181  WYTQTPTGAEAFIKRMAPHFDTPSQIGVDWYSAATAE                                  217
```

SEQ ID NO: 7 [13 aa C terminal extension attached for purification purposes onto 24 Kda]

```
  1  MGVALDRTRVDPQAVGNEVLKRNADKLNAMRGAEYGANVKVSGTDIRMNGGNSAGMLKQD           60
 61  VFNWRKELAQFEAYRGEAYKDADGYSVGLGHYLGSGNAGAGTTVTPEQAAQWFAEDTDRA          120
```

-continued

INFORMAL SEQUENCE LISTING

```
121  LDQGVRLADELGVTNNASILGLAGMAFQMGEGRARQFRNTFQAIKDRNKEAFEAGVRNSK      180
181  WYTQTPTGAEAFIKRMAPHFDTPSQIGVDWYSAATAEKLAAALEHHHHHH               230
```

SEQ ID NO: 8 [encoding chimeric GP36 segment linked to BPI segment; P225]
a. Construct nucleotide sequence: P225

```
  1  ATGGGCCATCATCATCATCATCATCATCATCATCATCACAGCAGCGGCCATATCGAAGGTCGT   60
 61  CATATGGGTGTGGCCCTGGACCGCACGCGGGTTGATCCCCAGGCAGTCGGCAACGAGGTG     120
121  CTCAAGCGCAACGCGGATAAGCTGAATGCGATGCGGGGCGCCGAGTACGGTGCCAACGTC     180
181  AAGGTCAGCGGCACGGACATTCGCATGAACGGGGGTAACAGTGCCGGCATGCTGAAGCAG     240
241  GACGTGTTCAACTGGCGGAAGGAACTGGCTCAGTTCGAGGCTTACCGAGGGGAGGCGTAT     300
301  AAGGATGCCGATGGTTATAGTGTGGGCCTGGGGCATTACCTGGGCAGTGGCAATGCTGGG     360
361  GCAGGTACTACAGTCACGCCTGAGCAAGCCGCGCAGTGGTTCGCCGAGGACACCGACCGC     420
421  GCACTCGACCAGGGTGTGAGGTTGGCCGACGAGCTGGGCGTTACGAACAATGCCTCTATC     480
481  CTGGGATTGGCCGGTATGGCCTTCCAGATGGGCGAAGGACGTGCCCGGCAGTTCCGTAAC     540
541  ACCTTCCAGGCGATCAAGGATCGCAACAAGGAAGCCTTCGAGGCTGGTGTGCGAAACAGC     600
601  AAGTGGTACACGCAGACGCCCACCGGGGCCGAGGCATTCATCAAGCGCATGGCGCCCCAC     660
661  TTCGATACACCGAGTCAAATCGGTGTCGATTGGTACAGCGCCGCAACAGCGGAGCGCCGT     720
721  CGCGCGTCCCTGATGGTGCTGGTCGCCATAGGCACCGCCGTGACAGCGGCCGTCAACCCT     780
781  GGCGTCGTGGTCAGGCGCCGTCGCTAA                                      807
```

Part 1 (1-66) is N terminal extension including poly His for purification (22 aa)
Part 2 (67-714) is GP36 muralytic fragment domain segment (aa 683 to 898; 217 aa)
Part 3 (715-804) is linker (RRR) with BPI TMD domain segment (aa 16-39) with RRR C terminus (33 aa)

SEQ ID NO: 9 [vector seq-GP36 muralytic domain-RRR-BPI TMD-RRR; P225 polypeptide; N terminus may have Met removed in a prokaryotic production host]

```
  1  MGHHHHHHHHHHSSGHIEGRHMGVALDRTRVDPQAVGNEVLKRNADKLNAMRGAEYGANV      60
 61  KVSGTDIRMNGGNSAGMLKQDVFNWRKELAQFEAYRGEAYKDADGYSVGLGHYLGSGNAG     120
121  AGTTVTPEQAAQWFAEDTDRALDQGVRLADELGVTNNASILGLAGMAFQMGEGRARQFRN     180
181  TFQAIKDRNKEAFEAGVRNSKWYTQTPTGAEAFIKRMAPHFDTPSQIGVDWYSAATAERR     240
241  RASLMVLVAIGTAVTAAVNPGVVVRRRR                                     268
```

SEQ ID NO: 10 P266 construct Nucleic acid:
1-6 = ATG (start codon) GGC: Bases generated due to cloning enzyme (NheI) site
7-24 = Sequence encoding 6Xhis (SEQ ID NO: 24) tag
25-672 = Sequence encoding GP36CD sequence
673-681 = Sequence encoding linker arginines
682-753 = Sequence encoding BPI MTD
754-762 = Sequence encoding terminal arginines
763-765 = TGA: Sequence encoding stop codon

```
  1  ATGGGCCATCATCATCATCATCATGGTGTAGCTCTTGATCGCACGCGGGTTGATCCCCAG      60
 61  GCAGTCGGCAACGAGGTGCTCAAGCGCAACGCGGATAAGCTGAATGCGATGCGGGGCGCC     120
121  GAGTACGGTGCCAACGTCAAGGTCAGCGGCACGGACATTCGCATGAACGGGGGTAACAGT     180
181  GCCGGCATGCTGAAGCAGGACGTGTTCAACTGGCGGAAGGAACTGGCTCAGTTCGAGGCT     240
241  TACCGAGGGGAGGCGTATAAGGATGCCGATGGTTATAGTGTGGGCCTGGGGCATTACCTG     300
301  GGCAGTGGCAATGCTGGGGCAGGTACTACAGTCACGCCTGAGCAAGCCGCGCAGTGGTTC     360
361  GCCGAGGACACCGACCGCGCACTCGACCAGGGTGTGAGGTTGGCCGACGAGCTGGGCGTT     420
421  ACGAACAATGCCTCTATCCTGGGATTGGCCGGTATGGCCTTCCAGATGGGCGAAGGACGT     480
481  GCCCGGCAGTTCCGTAACACCTTCCAGGCGATCAAGGATCGCAACAAGGAAGCCTTCGAG     540
541  GCTGGTGTGCGAAACAGCAAGTGGTACACGCAGACGCCCAACCGGGCCGAGGCATTCATC     600
601  AAGCGCATGGCGCCCCACTTCGATACACCGAGTCAAATCGGTGTCGATTGGTACAGCGCC     660
661  GCAACAGCGGAGCGCCGTCGCGCGTCCCTGATGGTGCTGGTCGCCATAGGCACCGCCGTG     720
721  ACAGCGGCCGTCAACCCTGGCGTCGTGGTCAGGCGCCGTCGCTGA                    765
```

SEQ ID NO: 11 P266 amino acid sequence (254 aa):
1 = M (start codon; removed by producing coli host)
2 = G: Amino acid generated due to cloning enzyme site
3-8 = 6XHis (SEQ ID NO: 24) tag
9-244 = GP36 Catalytic (muralytic) Domain sequence
225-227 = Linker arginines
228-251 = BPI TMD
252-254 = N-Terminal arginines
[vector seq-his6-GP36 muralytic domain-RRR-BPI TMD-RRR; P266 polypeptide]

```
  1  MGHHHHHHGV ALDRTRVDPQ AVGNEVLKRN ADKLNAMRGA EYGANVKVSG TDIRMNGGNS      60
 61  AGMLKQDVFN WRKELAQFEA YRGEAYKDAD GYSVGLGHYL GSGNAGAGTT VTPEQAAQWF     120
121  AEDTDRALDQ GVRLADELGV TNNASILGLA GMAFQMGEGR ARQFRNTFQA IKDRNKEAFE     180
181  AGVRNSKWYT QTPTGAEAFI KRMAPHFDTP SQIGVDWYSA ATAERRRASL MVLVAIGTAV     240
241  TAAVNPGVVV RRRR                                                      254
```

SEQ ID NO: 12 Nucleotide sequence of P275 construct

```
  1  ATGGGCCATCATCATCATCATCATGGTGTAGCTCTTGATCGCACGCGGGTTGATCCCCAG      60
 61  GCAGTCGGCAACGAGGTGCTCAAGCGCAACGCGGATAAGCTGAATGCGATGCGGGGCGCC     120
121  GAGTACGGTGCCAACGTCAAGGTCAGCGGCACGGACATTCGCATGAACGGGGGTAACAGT     180
181  GCCGGCATGCTGAAGCAGGACGTGTTCAACTGGCGGAAGGAACTGGCTCAGTTCGAGGCT     240
241  TACCGAGGGGAGGCGTATAAGGATGCCGATGGTTATAGTGTGGGCCTGGGGCATTACCTG     300
```

-continued

| INFORMAL SEQUENCE LISTING |
|---|

301 GGCAGTGGCAATGCTGGGGCAGGTACTACAGTCACGCCTGAGCAAGCCGCGCAGTGGTTC 360
361 GCCGAGGACACCGACCGCGCACTCGACCAGGGTGTGAGGTTGGCCGACGAGCTGGGCGTT 420
421 ACGAACAATGCCTCTATCCTGGGATTGGCCGGTATGGCCTTCCAGATGGGCGAAGGACGT 480
481 GCCCGGCAGTTCCGTAACACCTTCCAGGCGATCAAGGATCGCAACAAGGAAGCCTTCGAG 540
541 GCTGGTGTGCGAAACAGCAAGTGGTACACGCAGACGCCCAACCGGGCCGAGGCATTCATC 600
601 AAGCGCATGGCGCCCCACTTCGATACACCGAGTCAAATCGGTGTCGATTGGTACAGCGCC 660
661 GCAACAGCGGAGCGCCGTCGCGCGTCCCTGATGGAGCTGGACGCCAAAGGCACCGCCGTG 720
721 ACAGCGGCCGTCAACCCTGGCGTCGTGGTCAGGCGCCGTCGCTGA 765

SEQ ID NO: 13 P275 polypeptide construct; in BPI domain V232 to E; V234 to D; I236 to K
1 MGHHHHHHGV ALDRTRVDPQ AVGNEVLKRN ADKLNAMRGA EYGANVKVSG TDIRMNGGNS 60
61 AGMLKQDVFN WRKELAQFEA YRGEAYKDAD GYSVGLGHYL GSGNAGAGTT VTPEQAAQWF 120
121 AEDTDRALDQ GVRLADELGV TNNASILGLA GMAFQMGEGR ARQFRNTFQA IKDRNKEAFE 180
181 AGVRNSKWYT QTPTGAEAFI KRMAPHFDTP SQIGVDWYSA ATAERRRASL MELDAKGTAV 240
241 TAAVNPGVVV RRRR 254

SEQ ID NO: 14 GP36 MD-P134 Holin MTD chimera construct
1 ATGGGCCATCATCATCATCATCATCATCATCATCATCACAGCAGCGGCCATATCGAAGGTCGT 60
61 CATATGGGTGTGGCCCTGGACCGCACGCGGGTTGATCCCCAGGCAGTCGGCAACGAGGTG 120
121 CTCAAGCGCAACGCGGATAAGCTGAATGCGATGCGGGGCGCCGAGTACGGTGCCAACGTC 180
181 AAGGTCAGCGGCACGGACATTCGCATGAACGGGGGTAACAGTGCCGGCATGCTGAAGCAG 240
241 GACGTGTTCAACTGGCGGAAGGAACTGGCTCAGTTCGAGGCTTACCGAGGGGAGGCGTAT 300
301 AAGGATGCCGATGGTTATAGTGTGGGCCTGGGGCATTACCTGGGCAGTGGCAATGCTGGG 360
361 GCAGGTACTACAGTCACGCCTGAGCAAGCCGCGCAGTGGTTCGCCGAGGACACCGACCGC 420
421 GCACTCGACCAGGGTGTGAGGTTGGCCGACGAGCTGGGCGTTACGAACAATGCCTCTATC 480
481 CTGGGATTGGCCGGTATGGCCTTCCAGATGGGCGAAGGACGTGCCCGGCAGTTCCGTAAC 540
541 ACCTTCCAGGCGATCAAGGATCGCAACAAGGAAGCCTTCGAGGCTGGTGTGCGAAACAGC 600
601 AAGTGGTACACGCAGACGCCCACCGGGGCCGAGGCATTCATCAAGCGCATGGCGCCCCAC 660
661 TTCGATACACCGAGTCAAATCGGTGTCGATTGGTACAGCGCCGCAACAGCGGAGCGCCGT 720
721 CGCGAGATCGCCAGCCTCTGTGCTGCGGTACTCACCGCGCTCTACGTGGGCGCCCAGCTC 780
781 ATCACCCTGCTCCGCCGTCGCTGA 804

SEQ ID NO: 15 GP36 MD-P134 holin MTD polypeptide sequence
1 MGHHHHHHHH HHSSGHIEGR HMGVALDRTR VDPQAVGNEV LKRNADKLNA MRGAEYGANV 60
61 KVSGTDIRMN GGNSAGMLKQ DVFNWRKELA QFEAYRGEAY KDADGYSVGL GHYLGSGNAG 120
121 AGTTVTPEQA AQWFAEDTDR ALDQGVRLAD ELGVTNNASI LGLAGMAFQM GEGRARQFRN 180
181 TFQAIKDRNK EAFEAGVRNS KWYTQTPTGA EAFIKRMAPH FDTPSQIGVD WYSAATAERR 240
241 REIASLCAAV LTALYVGAQL ITLLRRR 267

SEQ ID NO: 16 GP36 MD-Lipopolysaccharide binding protein MTD construct
1 ATGGGCCATCATCATCATCATCATCATCATCATCATCACAGCAGCGGCCATATCGAAGGTCGT 60
61 CATATGGGTGTGGCCCTGGACCGCACGCGGGTTGATCCCCAGGCAGTCGGCAACGAGGTG 120
121 CTCAAGCGCAACGCGGATAAGCTGAATGCGATGCGGGGCGCCGAGTACGGTGCCAACGTC 180
181 AAGGTCAGCGGCACGGACATTCGCATGAACGGGGGTAACAGTGCCGGCATGCTGAAGCAG 240
241 GACGTGTTCAACTGGCGGAAGGAACTGGCTCAGTTCGAGGCTTACCGAGGGGAGGCGTAT 300
301 AAGGATGCCGATGGTTATAGTGTGGGCCTGGGGCATTACCTGGGCAGTGGCAATGCTGGG 360
361 GCAGGTACTACAGTCACGCCTGAGCAAGCCGCGCAGTGGTTCGCCGAGGACACCGACCGC 420
421 GCACTCGACCAGGGTGTGAGGTTGGCCGACGAGCTGGGCGTTACGAACAATGCCTCTATC 480
481 CTGGGATTGGCCGGTATGGCCTTCCAGATGGGCGAAGGACGTGCCCGGCAGTTCCGTAAC 540
541 ACCTTCCAGGCGATCAAGGATCGCAACAAGGAAGCCTTCGAGGCTGGTGTGCGAAACAGC 600
601 AAGTGGTACACGCAGACGCCCACCGGGGCCGAGGCATTCATCAAGCGCATGGCGCCCCAC 660
661 TTCGATACACCGAGTCAAATCGGTGTCGATTGGTACAGCGCCGCAACAGCGGAGCGCCGT 720
721 CGCTCCGACTCCTCCATCCGGGTCCAGGGCCGTTGGAAGGTGCGCGCGTCATTCTTCAAA 780
781 CTGCAGGGCTCCTTCGATGTCAGTGTCAAGGGCCGCCGTCGCTGA 825

SEQ ID NO: 17 GP36 MD-LPS binding protein MTD construct polypeptide sequence
1 MGHHHHHHHH HHSSGHIEGR HMGVALDRTR VDPQAVGNEV LKRNADKLNA MRGAEYGANV 60
61 KVSGTDIRMN GGNSAGMLKQ DVFNWRKELA QFEAYRGEAY KDADGYSVGL GHYLGSGNAG 120
121 AGTTVTPEQA AQWFAEDTDR ALDQGVRLAD ELGVTNNASI LGLAGMAFQM GEGRARQFRN 180
181 TFQAIKDRNK EAFEAGVRNS KWYTQTPTGA EAFIKRMAPH FDTPSQIGVD WYSAATAERR 240
241 RSDSSIRVQG RWKVRASFFK LQGSFDVSVK GRRR 274

SEQ ID NO: 18 GP36 MD-T4 phage, gp5 beta helix MTD chimera construct
1 ATGGGTGTGGCCCTGGACCGCACGCGGGTTGATCCCCAGGCAGTCGGCAACGAGGTGCTC 60
61 AAGCGCAACGCGGATAAGCTGAATGCGATGCGGGGCGCCGAGTACGGTGCCAACGTCAAG 120
121 GTCAGCGGCACGGACATTCGCATGAACGGGGGTAACAGTGCCGGCATGCTGAAGCAGGAC 180
181 GTGTTCAACTGGCGGAAGGAACTGGCTCAGTTCGAGGCTTACCGAGGGGAGGCGTATAAG 240
241 GATGCCGATGGTTATAGTGTGGGCCTGGGGCATTACCTGGGCAGTGGCAATGCTGGGGCA 300
301 GGTACTACAGTCACGCCTGAGCAAGCCGCGCAGTGGTTCGCCGAGGACACCGACCGCGCA 360
361 CTCGACCAGGGTGTGAGGTTGGCCGACGAGCTGGGCGTTACGAACAATGCCTCTATCCTG 420
421 GGATTGGCCGGTATGGCCTTCCAGATGGGCGAAGGACGTGCCCGGCAGTTCCGTAACACC 480
481 TTCCAGGCGATCAAGGATCGCAACAAGGAAGCCTTCGAGGCTGGTGTGCGAAACAGCAAG 540
541 TGGTACACGCAGACGCCCAACCGGGCCGAGGCATTCATCAAGCGCATGGCGCCCCACTTC 600
601 GATACACCGAGTCAAATCGGTGTCGATTGGTACAGCGCCGCAACAGCGGAGAAGCTTTAT 660
661 GTGCATACAATGGAAACTGAAAGCGGACATATTCAGGAATTTGATGATACCCCTGGCAA 720
721 GAACGATATAGATTAGTTCATCCAACTGGAACTTATGAAGAAGTATCACCATCAGGAAGA 780

-continued

INFORMAL SEQUENCE LISTING

```
 781 AGAACAAGAAAAACTGTTGATAATTTGTATGATATAACCAATGCTGATGGTAATTTTTTG      840
 841 GTAGCCGGTGATAAAAAGACTAACGTCGGTGGTTCAGAAATTTATTATAACATGGATAAT      900
 901 CGTTTACATCAAATCGATGGAAGCAATACAATATTTGTACGTGGAGACGAAACGAAAACT      960
 961 GTTGAAGGTAATGGAACTATCCTAGTTAAAGGTAATGTTACTATTATAGTTGAAGGTAAT     1020
1021 GCTGACATTACAGTTAAAGGAGATGCTACCACTTTAGTTGAAGGAAATCAAACTAACACA     1080
1081 GTAAATGGAAATCTTTCTTGGAAAGTTGCCGGGACAGTTGATTGGGATGTCGGTGGTGAT     1140
1141 TGGACAGAAAAAATGGCATCTATGAGTTCTATTTCATCTGGTCAATACACAATTGATGGA     1200
1201 TCGAGGATTGACATTGGCCTCGAGCACCACCACCACCACCACTAA                   1245

SEQ ID NO: 19 GP36 MD-T4 phage, gp5 beta helix MTD chimera polypeptide
  1  MGVALDRTRV DPQAVGNEVL KRNADKLNAM RGAEYGANVK VSGTDIRMNG GNSAGMLKQD   60
 61  VFNWRKELAQ FEAYRGEAYK DADGYSVGLG HYLGSGNAGA GTTVTPEQAA QWFAEDTDRA  120
121  LDQGVRLADE LGVTNNASIL GLAGMAFQMG EGRARQFRNT FQAIKDRNKE AFEAGVRNSK  180
181  WYTQTPNRAE AFIKRMAPHF DTPSQIGVDW YSAATAEKLY VHTMETESGH IQEFDDTPGQ  240
241  ERYRLVHPTG TYEEVSPSGR RTRKTVDNLY DITNADGNFL VAGDKKTNVG GSEIYYNMDN  300
301  RLHQIDGSNT IFVRGDETKT VEGNGTILVK GNVTIIVEGN ADITVKGDAT TLVEGNQTNT  360
361  VNGNLSWKVA GTVDWDVGGD WTEKMASMSS ISSGQYTIDG SRIDIGLEHH HHHH        414

SEQ ID NO: 20 GP36 MD-S type pyocin outer membrane translocation (OMT)
domain chimera construct
   1 ATGGGTGTGGCCCTGGACCGCACGCGGGTTGATCCCCAGGCAGTCGGCAACGAGGTGCTC       60
  61 AAGCGCAACGCGGATAAGCTGAATGCGATGCGGGGCGCCGAGTACGGTGCCAACGTCAAG      120
 121 GTCAGCGGCACGGACATTCGCATGAACGGGGGTAACAGTGCCGGCATGCTGAAGCAGGAC      180
 181 GTGTTCAACTGGCGGAAGGAACTGGCTCAGTTCGAGGCTTACCGAGGGGAGGCGTATAAG      240
 241 GATGCCGATGGTTATAGTGTGGGCCTGGGGCATTACCTGGGCAGTGGCAATGCTGGGGCA      300
 301 GGTACTACAGTCACGCCTGAGCAAGCCGCGCAGTGGTTCGCCGAGGACACCGACCGCGCA      360
 361 CTCGACCAGGGTGTGAGGTTGGCCGACGAGCTGGGCGTTACGAACAATGCCTCTATCCTG      420
 421 GGATTGGCCGGTATGGCCTTCCAGATGGGCGAAGGACGTGCCCGGCAGTTCCGTAACACC      480
 481 TTCCAGGCGATCAAGGATCGCAACAAGGAAGCCTTCGAGGCTGGTGTGCGAAACAGCAAG      540
 541 TGGTACACGCAGACGCCCAACCGGGCCGAGGCATTCATCAAGCGCATGGCGCCCCACTTC      600
 601 GATACACCGAGTCAAATCGGTGTCGATTGGTACAGCGCCGCAACAGCGGAGAAGCTTCAA      660
 661 GCGTTGCAAGATGCTATTAAATTTACTGCCGACTTTTATAAGGAAGTAACTGAGAAATTT      720
 721 GGCGCACGAACATCGGAGATGGCGCGCCAACTGGCCGAAGGCGCCAGGGGGAAAAATATC      780
 781 AGGAGTTCGGCGGAAGCAATCAAGTCGTTTGAAAAGCACAAGGATGCGTTAAATAAAAAA      840
 841 CTTAGCCTTAAAGATAGGCAAGCCATTGCCAAAGCCTTTGATTCTCTAGACAAGCAGATG      900
 901 ATGGCGAAGAGCCTTGAGAAATTTAGCAAAGGCTTTGGAGTTGTAGGCAAAGCTATTGAC      960
 961 GCCGCCAGCCTGTACCAAGAGTTCAAGATATCTACGGAAACCGGGGACTGGAAACCATTC     1020
1021 TTTGTAAAAATTGAAACACTAGCTGCTGGTGCGGCCGCCAGTTGGCTTGTGGGTATTGCA     1080
1081 TTTGCCACGGCAACAGCCACTCCTATAGGCATTCTGGGGTTCGCACTGGTAATGGCAGTT     1140
1141 ACCGGGGCGATGATTGACGAAGACCTTCTAGAAAAAGCAAACAATCTTGTAATATCCATT     1200
1201 CTCGAGCACCACCACCACCACCACTAA                                     1227

SEQ ID NO: 21 GP36 MD-S type pyocin (OMT) domain chimera polypeptide
408 aa. Theoretical pI/Mw: 8.44/44543.37
  1  MGVALDRTRV DPQAVGNEVL KRNADKLNAM RGAEYGANVK VSGTDIRMNG GNSAGMLKQD   60
 61  VFNWRKELAQ FEAYRGEAYK DADGYSVGLG HYLGSGNAGA GTTVTPEQAA QWFAEDTDRA  120
121  LDQGVRLADE LGVTNNASIL GLAGMAFQMG EGRARQFRNT FQAIKDRNKE AFEAGVRNSK  180
181  WYTQTPNRAE AFIKRMAPHF DTPSQIGVDW YSAATAEKLQ ALQDAIKFTA DFYKEVTEKF  240
241  GARTSEMARQ LAEGARGKNI RSSAEAIKSF EKHKDALNKK LSLKDRQAIA KAFDSLDKQM  300
301  MAKSLEKFSK GFGVVGKAID AASLYQEFKI STETGDWKPF FVKIETLAAG AAASWLVGIA  360
361  FATATATPIG ILGFALVMAV TGAMIDEDLL EKANNLVISI LEHHHHHH               408

SEQ ID NO: 22 GP36 MD-P22 Tail Spike protein MTD chimera construct
   1 ATGGGTGTGGCCCTGGACCGCACGCGGGTTGATCCCCAGGCAGTCGGCAACGAGGTGCTC       60
  61 AAGCGCAACGCGGATAAGCTGAATGCGATGCGGGGCGCCGAGTACGGTGCCAACGTCAAG      120
 121 GTCAGCGGCACGGACATTCGCATGAACGGGGGTAACAGTGCCGGCATGCTGAAGCAGGAC      180
 181 GTGTTCAACTGGCGGAAGGAACTGGCTCAGTTCGAGGCTTACCGAGGGGAGGCGTATAAG      240
 241 GATGCCGATGGTTATAGTGTGGGCCTGGGGCATTACCTGGGCAGTGGCAATGCTGGGGCA      300
 301 GGTACTACAGTCACGCCTGAGCAAGCCGCGCAGTGGTTCGCCGAGGACACCGACCGCGCA      360
 361 CTCGACCAGGGTGTGAGGTTGGCCGACGAGCTGGGCGTTACGAACAATGCCTCTATCCTG      420
 421 GGATTGGCCGGTATGGCCTTCCAGATGGGCGAAGGACGTGCCCGGCAGTTCCGTAACACC      480
 481 TTCCAGGCGATCAAGGATCGCAACAAGGAAGCCTTCGAGGCTGGTGTGCGAAACAGCAAG      540
 541 TGGTACACGCAGACGCCCAACCGGGCCGAGGCATTCATCAAGCGCATGGCGCCCCACTTC      600
 601 GATACACCGAGTCAAATCGGTGTCGATTGGTACAGCGCCGCAACAGCGGAGAAGCTTACA      660
 661 GACATCACTGCAAACGTAGTTGTTTCTAACCCTCGTCCAATCTTCACTGAATCCCGTTCG      720
 721 TTTAAAGCTGTTGCTAATGGGAAAATTTACATTGGTCAGATTGATACCGATCCGGTTAAT      780
 781 CCTGCCAATCAGATACCCGTATACATTGAAAATGAGGATGGCTCTCACGTCCAGATTACT      840
 841 CAGCCGCTAATTATCAACGCAGCCGGTAAAATCGTATACAACGGCCAACTGGTGAAAATT      900
 901 GTCACCGTTCAGGGTCATAGCATGGCTATCTATGATGCCAATGGTTCTCAGGTTGACTAT      960
 961 ATTGCTAACGTATTGAAGTACGATCCAGATCAATATTCAATAGAAGCTGATAAAAAATTT     1020
1021 AAGTATTCAGTAAAATTATCAGATTATCCAACATTGCAGGATGCAGCATCTGCTGCGGTT     1080
1081 GATGGCCTTCTTATCGATCGAGATTATAATTTTTATGGTGGAGAGACAGTTGATTTTGGC     1140
1141 GGAAAGGTTCTGACTATAGAATGTAAAGCTAAATTTATAGGAGATGGAAATCTTATTTTT     1200
1201 ACGAAATTAGGCAAAGGTTCCCGCATTGCCGGGGTTTTTATGGAAAGCACTACAACACCA     1260
1261 TGGGTTATCAAGCCTTGGACGGATGACAATCAGTGGCTAACGGATGCCGCAGCGGTCGTT     1320
1321 GCCACTTTAAAACAATCTAAAACTGATGGGTATCAGCCAACCGTAAGCGATTACGTTAAA     1380
1381 TTCCCAGGAATAGAAACGTTACTCCCACCTAATGCAAAAGGGCAAAACATAACGTCTACG     1440
```

-continued

INFORMAL SEQUENCE LISTING

```
1441 TTAGAAATTAGAGAATGTATAGGGGTCGAAGTTCATCGGGCTAGCGGTCTAATGGCTGGT        1500
1501 TTTTTGTTTAGAGGGTGTCACTTCTGCAAGATGGTAGACGCCAATAATCCAAGCGGAGGT        1560
1561 AAAGATGGCATTATAACCTTCGAAAACCTTAGCGGCGATTGGGGGAAGGGTAACTATGTC        1620
1621 ATTGGCGGACGAACCAGCTATGGGTCAGTAAGTAGCGCCCAGTTTTTACGTAATAATGGT        1680
1681 GGCTTTGAACGTGATGGTGGAGTTATTGGGTTTACTTCATATCGCGCTGGGGAGAGTGGC        1740
1741 GTTAAAACTTGGCAAGGTACTGTGGGCTCGACAACCTCTCGCAACTATAATCTGCAATTC        1800
1801 CGCGACTCGGTCGTTATTTACCCCGTATGGGACGGATTCGATTTAGGTGCTGACACTGAC        1860
1861 ATGAATCCGGAGTTGGACAGGCCAGGGGACTACCCTATAACCCAATACCCACTGCATCAG        1920
1921 TTACCCCTAAATCACCTGATTGATAATCTTCTGGTTCGCGGGGCGTTAGGTGTAGGTTTT        1980
1981 GGTATGGATGGTAAGGGCATGTATGTGTCTAATATTACCGTAGAAGATTGCGCTGGGTCT        2040
2041 GGCGCGTACCTACTCACCCACGAATCAGTATTTACCAATATAGCCATAATTGACACCAAT        2100
2101 ACTAAGGATTTCCAGGCGAATCAGATTTATATATCTGGGGCTTGCCGTGTGAACGGTTTA        2160
2161 CGTTTAATTGGGATCCGCTCAACCGATGGGCAGGGTCTAACCATAGACGCCCCTAACTCT        2220
2221 ACCGTAAGCGGTATAACCGGGATGGTAGACCCCTCTAGAATTAATGTTGCTAATTTGGCA        2280
2281 GAAGAAGGGTTAGGTAATATCCGCGCTAATAGTTTCGGCTATGATAGCGCAGCGATTAAA        2340
2341 CTGCGGATTCATAAGTTATCAAAGACATTAGATAGCGGAGCATTGTACTCCCACATTAAC        2400
2401 GGGGGGGCCGGTTCTGGCTCAGCGTATACTCAACTTACTGCTATTTCAGGTAGCACACCT        2460
2461 GACGCTGTATCATTAAAAGTTAACCACAAAGATTGCAGGGGGGCAGAGATACCATTTGTT        2520
2521 CCTGACATCGCGTCAGATGATTTTATAAAGGATTCCTCATGTTTTTTGCCATATTGGGAA        2580
2581 AATAATTCTACTTCTTTAAAGGCTTTAGTGAAAAAACCCAATGGAGAATTAGTTAGATTA        2640
2641 ACCTTGGCAACACTTCTCGAGCACCACCACCACCACCACTAG                          2682

SEQ ID NO: 23 GP36-P22 Tail Spike protein MTD polypeptide
  1  MGVALDRTRV DPQAVGNEVL KRNADKLNAM RGAEYGANVK VSGTDIRMNG GNSAGMLKQD    60
 61  VFNWRKELAQ FEAYRGEAYK DADGYSVGLG HYLGSGNAGA GTTVTPEQAA QWFAEDTDRA   120
121  LDQGVRLADE LGVTNNASIL GLAGMAFQMG EGRARQFRNT FQAIKDRNKE AFEAGVRNSK   180
181  WYTQTPNRAE AFIKRMAPHF DTPSQIGVDW YSAATAEKLT DITANVVVSN PRPIFTESRS   240
241  FKAVANGKIY IGQIDTDPVN PANQIPVYIE NEDGSHVQIT QPLIINAAGK IVYNGQLVKI   300
301  VTVQGHSMAI YDANGSQVDY IANVLKYDPD QYSIEADKKF KYSVKLSDYP TLQDAASAAV   360
361  DGLLIDRDYN FYGGETVDFG GKVLTIECKA KFIGDGNLIF TKLGKGSRIA GVFMESTTTP   420
421  WVIKPWTDDN QWLTDAAAVV ATLKQSKTDG YQPTVSDYVK FPGIETLLPP NAKGQNITST   480
481  LEIRECIGVE VHRASGLMAG FLFRGCHFCK MVDANNPSGG KDGIITFENL SGDWGKGNYV   540
541  IGGRTSYGSV SSAQFLRNNG GFERDGGVIG FTSYRAGESG VKTWQGTVGS TTSRNYNLQF   600
601  RDSVVIYPVW DGFDLGADTD MNPELDRPGD YPITQYPLHQ LPLNHLIDNL LVRGALGVGF   660
661  GMDGKGMYVS NITVEDCAGS GAYLLTHESV FTNIAIIDTN TKDFQANQIY ISGACRVNGL   720
721  RLIGIRSTDG QGLTIDAPNS TVSGITGMVD PSRINVANLA EEGLGNIRAN SFGYDSAAIK   780
781  LRIHKLSKTL DSGALYSHIN GGAGSGSAYT QLTAISGSTP DAVSLKVNHK DCRGAEIPFV   840
841  PDIASDDFIK DSSCFLPYWE NNSTSLKALV KKPNGELVRL TLATLLEHHH HHH          893
```

What is claimed is:

1. A chimeric polypeptide comprising a muralytic domain (MD) from a virion-associated muralytic enzyme, wherein the MD comprises a sequence at least 90% identical to amino acids 683-898 of SEQ ID NO:2 and is capable of lysing chloroform-treated *Pseudomonas aeruginosa* bacteria and a membrane traversing domain (MTD) segment, wherein the segment comprises a sequence at least 80% identical to amino acids 16-39 of SEQ ID NO:4 and is capable of traversing the outer membrane of *Pseudomonas aeruginosa* bacteria.

2. The chimeric polypeptide of claim 1, which comprises a sequence having at least 90% identity to a sequence selected from: SEQ ID NO:9, SEQ ID NO:11, and SEQ ID NO: 13.

3. The chimeric polypeptide of claim 2, wherein the chimeric polypeptide comprises SEQ ID NO: 9.

4. The chimeric polypeptide of claim 2, wherein the chimeric polypeptide comprises SEQ ID NO: 11.

5. The chimeric polypeptide of claim 2, wherein the chimeric polypeptide comprises SEQ ID NO: 13.

6. The chimeric polypeptide of claim 1, wherein the chimeric polypeptide is attached to polyethylene glycol.

7. A pharmaceutical composition comprising the chimeric polypeptide of claim 1 and a pharmaceutically acceptable excipient.

8. An antibacterial formulation comprising the chimeric polypeptide of claim 1 and an agent that reduces oxidation.

* * * * *

SEQUENCE LISTING

```
<160> NUMBER OF SEQ ID NOS: 35

<210> SEQ ID NO 1
<211> LENGTH: 2697
<212> TYPE: DNA
<213> ORGANISM: Pseudomonas phage P134
<220> FEATURE:
<223> OTHER INFORMATION: Pseudomonas phage P134 GP36 full length DNA,
      homolog of Pseudomonas phage phiKMV ORF36 structural protein
      containing C-terminal lysozyme domain

<400> SEQUENCE: 1

atggcggaat cgcaacgtgc ttcccaagag cttgggatca acgtcggaca ggcgcaactc      60

cagccgggcc agagtgcccg gcgcggagtg cgcgactccg aggtcaacta cagcggtccg     120

agtgtaggct cgcagattct cgacggcatc ctgggtgccg gtcagcagat cgctggcaaa     180

tggttcgagc acaacgtgca gcaggaagtt ctgcgcggtg agcgtgcccg tatggccggc     240

gaggctgagg aggcagtaga cagcaacgta ctggccaaac cattcgtgaa gggtggttgg     300

cgtaagcagg actaccgtat cgcccaggcg gacttcagcc tgaagatgca gcgattcatc     360

gccaacaagg gccgggagat gactcccgag gagttccgca agtacctgtc ccaggaggct     420

acgcacgtcc tggactcgac cgagggcatg aaccccaacg atgccctaca ggcgatggca     480

cagcagcaga aggccgagga acagctcttt ggcatgcagg ctaaggcgta catggattgg     540

tccatcgacc aggccgcacg gggcttccgc acccagggta acagcatcct ggccaaggcc     600
```

```
gtacatgccc aggccaccgg cgacgagcta tcccggcaac tcagcctgga agaggccggc    660
ctgttctata ccaacatcat gacctccgag gatatcccgc tggaggtacg tgacaaggtg    720
ggtatgcagt tcctggcggc cagcctggac atgaaccagc ggggcatcta tgagggcctg    780
cgcgatgccg ggttcctgga cagtatgtcc tttgacgacc ggcgtgcgct caacggcctc    840
tatgaaaaat cgaaggcaca gacccgtgcc aaggaatcga tggctaccct gcgggccgac    900
gcggacttcc agcagcgggt ggccaacggc gccatcacag accttgccga ggttgaggcg    960
tactcacgag gcatggtcga ggagggccgc tggagcgacg ctcaggccat ctcgttcatg   1020
accaaggcca tgaccggcct gggcaacgct cagcgcatgc agggcatcat ggcggccttg   1080
gaagccggag acatcaacgc cctccacacg ctgggtacca acgtcaccga ggcgctggag   1140
cagtgggaca agatgcaggc cgccaacggc tcaagcctga ctgaccgtct cgtgcagggc   1200
acacagctcg gcctgcgcct ggggaccttc cccaagacct acggcgagtc cgtgggcagc   1260
gcggtgcgca tgatccaggc cgccaaggaa ggcgaggcaa acccggagct ggtcaacacg   1320
ctgaacagca tcttcgaaca ggtggcctcg gcccaggaga tcaacccatc cgccggcaac   1380
gtgatgctat ccggcatccc ggaagccgag cagggcgccg tggcctgggc actcaagcag   1440
atgaagatgg gcatcgcacc agctcaagct ctgcgcgagt ttagcgccaa cgccgaagtc   1500
gtgaagcaga tggacgagtt cgagaaaggc cagaacacca aggcattcaa ggacaacctc   1560
ggtaagcagg tcaacgacaa gttcgtgaac aacatcttcg gtcgagcctg gaacatgctg   1620
accggcgaga gcgacctgag caacaacgag gccgtcctga gcatgtatcg ccgggcgacc   1680
atcgacgagg cgaactggct ggccagcgac cgcaagcatg cgggtctgct caccagcgac   1740
acgggccgcg aggccctgct ggagatcgcc gccgccaacg tgcgtaaccg caccatccag   1800
gtaggcgaag gtcggaacct gaaggaaggg gacctattca gccgccgcga tagcgcgccg   1860
ctgatcctgc ctcgcggcac caccgccgag cagctattcg ggaccaacga caccgagacc   1920
atcggaaccg tcctggccga gcagcacaag ccgcatgtcg aaggactcct cggctacaag   1980
tcggtagtcg ccttcgagta cgaccgcacc agtggcagcc tcctcgccgt cgagtacgac   2040
gagaacggtg tggccctgga ccgcacgcgg gttgatcccc aggcagtcgg caacgaggtg   2100
ctcaagcgca acgcggataa gctgaatgcg atgcggggcg ccgagtacgg tgccaacgtc   2160
aaggtcagcg gcacggacat tcgcatgaac gggggtaaca gtgccggcat gctgaagcag   2220
gacgtgttca actggcggaa ggaactggct cagttcgagg cttaccgagg ggaggcgtat   2280
aaggatgccg atggttatag tgtgggcctg gggcattacc tgggcagtgg caatgctggg   2340
gcaggtacta cagtcacgcc tgagcaagcc gcgcagtggt tcgccgagga caccgaccgc   2400
gcactcgacc agggtgtgag gttggccgac gagctgggcg ttacgaacaa tgcctctatc   2460
ctgggattgg ccggtatggc cttccagatg ggcgaaggac gtgcccggca gttccgtaac   2520
accttccagg cgatcaagga tcgcaacaag gaagccttcg aggctggtgt gcgaaacagc   2580
aagtggtaca cgcagacgcc caccggggcc gaggcattca tcaagcgcat ggcgccccac   2640
ttcgatacac cgagtcaaat cggtgtcgat tggtacagcg ccgcaacagc ggagtaa      2697
```

<210> SEQ ID NO 2
<211> LENGTH: 898
<212> TYPE: PRT
<213> ORGANISM: Pseudomonas phage P134
<220> FEATURE:
<223> OTHER INFORMATION: Pseudomonas phage P134 GP36, homolog of
Pseudomonas phage phiKMV ORF36 structural protein containing -continued

```
      C-terminal lysozyme domain
<220> FEATURE:
<221> NAME/KEY: DOMAIN
<222> LOCATION: (683)...(898)
<223> OTHER INFORMATION: GP36 muralytic fragment domain segment
<220> FEATURE:
<221> NAME/KEY: DOMAIN
<222> LOCATION: (736)...(875)
<223> OTHER INFORMATION: GP36 catalytic domain (CD) in 24Kda construct

<400> SEQUENCE: 2

Met Ala Glu Ser Gln Arg Ala Ser Gln Glu Leu Gly Ile Asn Val Gly
 1               5                  10                  15

Gln Ala Gln Leu Gln Pro Gly Gln Ser Ala Arg Arg Gly Val Arg Asp
            20                  25                  30

Ser Glu Val Asn Tyr Ser Gly Pro Ser Val Gly Ser Gln Ile Leu Asp
        35                  40                  45

Gly Ile Leu Gly Ala Gly Gln Gln Ile Ala Gly Lys Trp Phe Glu His
    50                  55                  60

Asn Val Gln Gln Glu Val Leu Arg Gly Glu Arg Ala Arg Met Ala Gly
65                  70                  75                  80

Glu Ala Glu Glu Ala Val Asp Ser Asn Val Leu Ala Lys Pro Phe Val
                85                  90                  95

Lys Gly Gly Trp Arg Lys Gln Asp Tyr Arg Ile Ala Gln Ala Asp Phe
            100                 105                 110

Ser Leu Lys Met Gln Arg Phe Ile Ala Asn Lys Gly Arg Glu Met Thr
        115                 120                 125

Pro Glu Glu Phe Arg Lys Tyr Leu Ser Gln Glu Ala Thr His Val Leu
    130                 135                 140

Asp Ser Thr Glu Gly Met Asn Pro Asn Asp Ala Leu Gln Ala Met Ala
145                 150                 155                 160

Gln Gln Gln Lys Ala Glu Glu Gln Leu Phe Gly Met Gln Ala Lys Ala
                165                 170                 175

Tyr Met Asp Trp Ser Ile Asp Gln Ala Ala Arg Gly Phe Arg Thr Gln
            180                 185                 190

Gly Asn Ser Ile Leu Ala Lys Ala Val His Ala Gln Ala Thr Gly Asp
        195                 200                 205

Glu Leu Ser Arg Gln Leu Ser Leu Glu Glu Ala Gly Leu Phe Tyr Thr
    210                 215                 220

Asn Ile Met Thr Ser Glu Asp Ile Pro Leu Glu Val Arg Asp Lys Val
225                 230                 235                 240

Gly Met Gln Phe Leu Ala Ala Ser Leu Asp Met Asn Gln Arg Gly Ile
                245                 250                 255

Tyr Glu Gly Leu Arg Asp Ala Gly Phe Leu Asp Ser Met Ser Phe Asp
            260                 265                 270

Asp Arg Arg Ala Leu Asn Gly Leu Tyr Glu Lys Ser Lys Ala Gln Thr
        275                 280                 285

Arg Ala Lys Glu Ser Met Ala Thr Leu Arg Ala Asp Ala Asp Phe Gln
    290                 295                 300

Gln Arg Val Ala Asn Gly Ala Ile Thr Asp Leu Ala Glu Val Glu Ala
305                 310                 315                 320

Tyr Ser Arg Gly Met Val Glu Glu Gly Arg Trp Ser Asp Ala Gln Ala
                325                 330                 335

Ile Ser Phe Met Thr Lys Ala Met Thr Gly Leu Gly Asn Ala Gln Arg
            340                 345                 350

Met Gln Gly Ile Met Ala Ala Leu Glu Ala Gly Asp Ile Asn Ala Leu
```

```
        355                 360                 365

His Thr Leu Gly Thr Asn Val Thr Glu Ala Leu Glu Gln Trp Asp Lys
    370                 375                 380

Met Gln Ala Ala Asn Gly Ser Ser Leu Thr Asp Arg Leu Val Gln Gly
385                 390                 395                 400

Thr Gln Leu Gly Leu Arg Leu Gly Thr Phe Pro Lys Thr Tyr Gly Glu
                405                 410                 415

Ser Val Gly Ser Ala Val Arg Met Ile Gln Ala Ala Lys Glu Gly Glu
            420                 425                 430

Ala Asn Pro Glu Leu Val Asn Thr Leu Asn Ser Ile Phe Glu Gln Val
        435                 440                 445

Ala Ser Ala Gln Glu Ile Asn Pro Ser Ala Gly Asn Val Met Leu Ser
    450                 455                 460

Gly Ile Pro Glu Ala Glu Gln Gly Ala Val Ala Trp Ala Leu Lys Gln
465                 470                 475                 480

Met Lys Met Gly Ile Ala Pro Ala Gln Ala Leu Arg Glu Phe Ser Ala
                485                 490                 495

Asn Ala Glu Val Val Lys Gln Met Asp Glu Phe Glu Lys Gly Gln Asn
            500                 505                 510

Thr Lys Ala Phe Lys Asp Asn Leu Gly Lys Gln Val Asn Asp Lys Phe
        515                 520                 525

Val Asn Asn Ile Phe Gly Arg Ala Trp Asn Met Leu Thr Gly Glu Ser
    530                 535                 540

Asp Leu Ser Asn Asn Glu Ala Val Leu Ser Met Tyr Arg Arg Ala Thr
545                 550                 555                 560

Ile Asp Glu Ala Asn Trp Leu Ala Ser Asp Arg Lys His Ala Gly Leu
                565                 570                 575

Leu Thr Ser Asp Thr Gly Arg Glu Ala Leu Leu Glu Ile Ala Ala Ala
            580                 585                 590

Asn Val Arg Asn Arg Thr Ile Gln Val Gly Glu Gly Arg Asn Leu Lys
        595                 600                 605

Glu Gly Asp Leu Phe Ser Arg Arg Asp Ser Ala Pro Leu Ile Leu Pro
    610                 615                 620

Arg Gly Thr Thr Ala Glu Gln Leu Phe Gly Thr Asn Asp Thr Glu Thr
625                 630                 635                 640

Ile Gly Thr Val Leu Ala Glu Gln His Lys Pro His Val Glu Gly Leu
                645                 650                 655

Leu Gly Tyr Lys Ser Val Val Ala Phe Glu Tyr Asp Arg Thr Ser Gly
            660                 665                 670

Ser Leu Leu Ala Val Glu Tyr Asp Glu Asn Gly Val Ala Leu Asp Arg
        675                 680                 685

Thr Arg Val Asp Pro Gln Ala Val Gly Asn Glu Val Leu Lys Arg Asn
    690                 695                 700

Ala Asp Lys Leu Asn Ala Met Arg Gly Ala Glu Tyr Gly Ala Asn Val
705                 710                 715                 720

Lys Val Ser Gly Thr Asp Ile Arg Met Asn Gly Gly Asn Ser Ala Gly
                725                 730                 735

Met Leu Lys Gln Asp Val Phe Asn Trp Arg Lys Glu Leu Ala Gln Phe
            740                 745                 750

Glu Ala Tyr Arg Gly Glu Ala Tyr Lys Asp Ala Asp Gly Tyr Ser Val
        755                 760                 765

Gly Leu Gly His Tyr Leu Gly Ser Gly Asn Ala Gly Ala Gly Thr Thr
    770                 775                 780
```

-continued

Val Thr Pro Glu Gln Ala Ala Gln Trp Phe Ala Glu Asp Thr Asp Arg
785 790 795 800

Ala Leu Asp Gln Gly Val Arg Leu Ala Asp Glu Leu Gly Val Thr Asn
805 810 815

Asn Ala Ser Ile Leu Gly Leu Ala Gly Met Ala Phe Gln Met Gly Glu
820 825 830

Gly Arg Ala Arg Gln Phe Arg Asn Thr Phe Gln Ala Ile Lys Asp Arg
835 840 845

Asn Lys Glu Ala Phe Glu Ala Gly Val Arg Asn Ser Lys Trp Tyr Thr
850 855 860

Gln Thr Pro Thr Gly Ala Glu Ala Phe Ile Lys Arg Met Ala Pro His
865 870 875 880

Phe Asp Thr Pro Ser Gln Ile Gly Val Asp Trp Tyr Ser Ala Ala Thr
885 890 895

Ala Glu

<210> SEQ ID NO 3
<211> LENGTH: 1493
<212> TYPE: DNA
<213> ORGANISM: Homo sapiens
<220> FEATURE:
<223> OTHER INFORMATION: human FLJ96367 cDNA, similar to
bactericidal/permeability-increasing protein (BPI)

<400> SEQUENCE: 3
aggccttgag gttttggcag ctctggagga tgagagagaa catggccagg ggcccttgca 60
acgcgccgag atgggcgtcc ctgatggtgc tggtcgccat aggcaccgcc gtgacagcgg 120
ccgtcaaccc tggcgtcgtg gtcaggatct cccagaaggg cctggactac gccagccagc 180
aggggacggc cgctctgcag aaggagctga agaggatcaa gattcctgac tactcagaca 240
gctttaagat caagcatctt gggaaggggc attatagctt ctacagcatg gacatccgtg 300
aattccagct tcccagttcc cagataagca tggtgcccaa tgtgggcctt aagttctcca 360
tcagcaacgc caatatcaag atcagcggga aatggaaggc acaaaagaga ttcttaaaaa 420
tgagcggcaa ttttgacctg agcatagaag gcatgtccat ttcggctgat ctgaagctgg 480
gcagtaaccc cacgtcaggc aagcccacca tcacctgctc cagctgcagc agccacatca 540
acagtgtcca cgtgcacatc tcaaagagca aagtggggtg gctgatccaa ctcttccaca 600
aaaaaattga gtctgcgctt cgaaacaaga tgaacagcca ggtctgcgag aaagtgacca 660
attctgtatc ctccgagctg caaccttatt tccagactct gccagtaatg accaaaatag 720
attctgtggc tggaatcaac tatggtctgg tggcacctcc agcaaccacg gctgagaccc 780
tggatgtaca gatgaagggg gagttttaca gtgagaacca ccacaatcca cctccctttg 840
ctccaccagt gatggagttt cccgctgccc atgaccgcat ggtatacctg ggcctctcag 900
actacttctt caacacagcc gggcttgtat accaagaggc tggggtcttg aagatgaccc 960
ttagagatga catgattcca aaggagtcca aatttcgact gacaaccaag ttctttggaa 1020
ccttcctacc tgaggtggcc aagaagtttc ccaacatgaa gatacagatc catgtctcag 1080
cctccacccc gccacacctg tctgtgcagc ccaccggcct taccttctac cctgccgtgg 1140
atgtccaggc ctttgccgtc ctccccaact cctccctggc ttccctcttc ctgattggca 1200
tgcacacaac tggttccatg gaggtcagcg ccgagtccga caggcttgtt ggagagctca 1260
agctggatag gctgctcctg gaactgaagc actcaaatat tggccccttc ccggttgaat 1320

```
tgctgctgga tatcatgaac tacattgtac ccattcttgt gctgcccagg gttaacgaga   1380

aactacagaa aggcttccct ctcccgacgc cggccagagt ccagctctac aacgtagtgc   1440

ttcagcctca ccagaacttc ctgctgttcg gtgcagacgt tgtctataaa tga          1493


<210> SEQ ID NO 4
<211> LENGTH: 487
<212> TYPE: PRT
<213> ORGANISM: Homo sapiens
<220> FEATURE:
<223> OTHER INFORMATION: human FLJ96367, similar to
      bactericidal/permeability-increasing protein (BPI)
<220> FEATURE:
<221> NAME/KEY: DOMAIN
<222> LOCATION: (16)...(39)
<223> OTHER INFORMATION: transmembrane domain (TMD)

<400> SEQUENCE: 4

Met Arg Glu Asn Met Ala Arg Gly Pro Cys Asn Ala Pro Arg Trp Ala
 1               5                  10                  15

Ser Leu Met Val Leu Val Ala Ile Gly Thr Ala Val Thr Ala Ala Val
            20                  25                  30

Asn Pro Gly Val Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
    50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
    130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Glu Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
    290                 295                 300

Gly Val Leu Lys Met Thr Leu Arg Asp Asp Met Ile Pro Lys Glu Ser
```

-continued

```
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
        355                 360                 365

Ala Val Asp Val Gln Ala Phe Ala Val Leu Pro Asn Ser Ser Leu Ala
    370                 375                 380

Ser Leu Phe Leu Ile Gly Met His Thr Thr Gly Ser Met Glu Val Ser
385                 390                 395                 400

Ala Glu Ser Asp Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430

Leu Asp Ile Met Asn Tyr Ile Val Pro Ile Leu Val Leu Pro Arg Val
        435                 440                 445

Asn Glu Lys Leu Gln Lys Gly Phe Pro Leu Pro Thr Pro Ala Arg Val
    450                 455                 460

Gln Leu Tyr Asn Val Val Leu Gln Pro His Gln Asn Phe Leu Leu Phe
465                 470                 475                 480

Gly Ala Asp Val Val Tyr Lys
                485
```

<210> SEQ ID NO 5
<211> LENGTH: 654
<212> TYPE: DNA
<213> ORGANISM: Artificial Sequence
<220> FEATURE:
<223> OTHER INFORMATION: synthetic Pseudomonas phage P134 GP36 catalytic domain (CD), 24Kda construct, first CHCl3 test constuct

<400> SEQUENCE: 5

```
atgggtgtgg ccctggaccg cacgcgggtt gatccccagg cagtcggcaa cgaggtgctc      60

aagcgcaacg cggataagct gaatgcgatg cggggcgccg agtacggtgc caacgtcaag     120

gtcagcggca cggacattcg catgaacggg ggtaacagtg ccggcatgct gaagcaggac     180

gtgttcaact ggcggaagga actggctcag ttcgaggctt accgagggga ggcgtataag     240

gatgccgatg gttatagtgt gggcctgggg cattacctgg gcagtggcaa tgctggggca     300

ggtactacag tcacgcctga gcaagccgcg cagtggttcg ccgaggacac cgaccgcgca     360

ctcgaccagg gtgtgaggtt ggccgacgag ctgggcgtta cgaacaatgc ctctatcctg     420

ggattggccg gtatggcctt ccagatgggc gaaggacgtg cccggcagtt ccgtaacacc     480

ttccaggcga tcaaggatcg caacaaggaa gccttcgagg ctggtgtgcg aaacagcaag     540

tggtacacgc agacgcccac cggggccgag gcattcatca agcgcatggc gccccacttc     600

gatacaccga gtcaaatcgg tgtcgattgg tacagcgccg caacagcgga gtaa           654
```

<210> SEQ ID NO 6
<211> LENGTH: 217
<212> TYPE: PRT
<213> ORGANISM: Artificial Sequence
<220> FEATURE:
<223> OTHER INFORMATION: synthetic Pseudomonas phage P134 GP36 catalytic domain (CD), 24Kda construct, first CHCl3 test constuct
<220> FEATURE:
<221> NAME/KEY: DOMAIN
<222> LOCATION: (56)...(194)

<223> OTHER INFORMATION: Pseudomonas phage P134 GP36 catalytic domain
(CD)

<400> SEQUENCE: 6

Met Gly Val Ala Leu Asp Arg Thr Arg Val Asp Pro Gln Ala Val Gly
1 5 10 15

Asn Glu Val Leu Lys Arg Asn Ala Asp Lys Leu Asn Ala Met Arg Gly
20 25 30

Ala Glu Tyr Gly Ala Asn Val Lys Val Ser Gly Thr Asp Ile Arg Met
35 40 45

Asn Gly Gly Asn Ser Ala Gly Met Leu Lys Gln Asp Val Phe Asn Trp
50 55 60

Arg Lys Glu Leu Ala Gln Phe Glu Ala Tyr Arg Gly Glu Ala Tyr Lys
65 70 75 80

Asp Ala Asp Gly Tyr Ser Val Gly Leu Gly His Tyr Leu Gly Ser Gly
85 90 95

Asn Ala Gly Ala Gly Thr Thr Val Thr Pro Glu Gln Ala Ala Gln Trp
100 105 110

Phe Ala Glu Asp Thr Asp Arg Ala Leu Asp Gln Gly Val Arg Leu Ala
115 120 125

Asp Glu Leu Gly Val Thr Asn Asn Ala Ser Ile Leu Gly Leu Ala Gly
130 135 140

Met Ala Phe Gln Met Gly Glu Gly Arg Ala Arg Gln Phe Arg Asn Thr
145 150 155 160

Phe Gln Ala Ile Lys Asp Arg Asn Lys Glu Ala Phe Glu Ala Gly Val
165 170 175

Arg Asn Ser Lys Trp Tyr Thr Gln Thr Pro Thr Gly Ala Glu Ala Phe
180 185 190

Ile Lys Arg Met Ala Pro His Phe Asp Thr Pro Ser Gln Ile Gly Val
195 200 205

Asp Trp Tyr Ser Ala Ala Thr Ala Glu
210 215

<210> SEQ ID NO 7
<211> LENGTH: 230
<212> TYPE: PRT
<213> ORGANISM: Artificial Sequence
<220> FEATURE:
<223> OTHER INFORMATION: synthetic Pseudomonas phage P134 GP36 catalytic
domain (CD), 24Kda construct, first CHCl3 test
constuct with 13 aa C-terminal extension
<220> FEATURE:
<221> NAME/KEY: DOMAIN
<222> LOCATION: (56)...(194)
<223> OTHER INFORMATION: Pseudomonas phage P134 GP36 catalytic domain
(CD)
<220> FEATURE:
<221> NAME/KEY: DOMAIN
<222> LOCATION: (218)...(230)
<223> OTHER INFORMATION: 13 aa C-terminal extension with 6xHis tag for
purification

<400> SEQUENCE: 7

Met Gly Val Ala Leu Asp Arg Thr Arg Val Asp Pro Gln Ala Val Gly
1 5 10 15

Asn Glu Val Leu Lys Arg Asn Ala Asp Lys Leu Asn Ala Met Arg Gly
20 25 30

Ala Glu Tyr Gly Ala Asn Val Lys Val Ser Gly Thr Asp Ile Arg Met
35 40 45

Asn Gly Gly Asn Ser Ala Gly Met Leu Lys Gln Asp Val Phe Asn Trp

-continued

```
    50                  55                  60

Arg Lys Glu Leu Ala Gln Phe Glu Ala Tyr Arg Gly Glu Ala Tyr Lys
65                  70                  75                  80

Asp Ala Asp Gly Tyr Ser Val Gly Leu Gly His Tyr Leu Gly Ser Gly
                85                  90                  95

Asn Ala Gly Ala Gly Thr Thr Val Thr Pro Glu Gln Ala Ala Gln Trp
            100                 105                 110

Phe Ala Glu Asp Thr Asp Arg Ala Leu Asp Gln Gly Val Arg Leu Ala
        115                 120                 125

Asp Glu Leu Gly Val Thr Asn Asn Ala Ser Ile Leu Gly Leu Ala Gly
    130                 135                 140

Met Ala Phe Gln Met Gly Glu Gly Arg Ala Arg Gln Phe Arg Asn Thr
145                 150                 155                 160

Phe Gln Ala Ile Lys Asp Arg Asn Lys Glu Ala Phe Glu Ala Gly Val
                165                 170                 175

Arg Asn Ser Lys Trp Tyr Thr Gln Thr Pro Thr Gly Ala Glu Ala Phe
            180                 185                 190

Ile Lys Arg Met Ala Pro His Phe Asp Thr Pro Ser Gln Ile Gly Val
        195                 200                 205

Asp Trp Tyr Ser Ala Ala Thr Ala Glu Lys Leu Ala Ala Ala Leu Glu
    210                 215                 220

His His His His His His
225                 230


<210> SEQ ID NO 8
<211> LENGTH: 807
<212> TYPE: DNA
<213> ORGANISM: Artificial Sequence
<220> FEATURE:
<223> OTHER INFORMATION: synthetic chimeric P225 construct, GP36 segment
      linked to BPI segment, vector seq-GP36 muralytic domain-RRR-BPI
      TMD-RRR
<220> FEATURE:
<221> NAME/KEY: misc_feature
<222> LOCATION: (1)...(66)
<223> OTHER INFORMATION: Part 1 N terminal extension including poly His
      for purification
<220> FEATURE:
<221> NAME/KEY: misc_feature
<222> LOCATION: (67)...(714)
<223> OTHER INFORMATION: Part 2 GP36 muralytic fragment domain segment
<220> FEATURE:
<221> NAME/KEY: misc_feature
<222> LOCATION: (715)...(804)
<223> OTHER INFORMATION: Part 3 linker (RRR) with BPI TMD domain segment
      with RRR C terminus

<400> SEQUENCE: 8

atgggccatc atcatcatca tcatcatcat catcacagca gcggccatat cgaaggtcgt      60

catatgggtg tggccctgga ccgcacgcgg gttgatcccc aggcagtcgg caacgaggtg     120

ctcaagcgca acgcggataa gctgaatgcg atgcggggcg ccgagtacgg tgccaacgtc     180

aaggtcagcg gcacggacat tcgcatgaac gggggtaaca gtgccggcat gctgaagcag     240

gacgtgttca actggcggaa ggaactggct cagttcgagg cttaccgagg ggaggcgtat     300

aaggatgccg atggttatag tgtgggcctg gggcattacc tgggcagtgg caatgctggg     360

gcaggtacta cagtcacgcc tgagcaagcc gcgcagtggt tcgccgagga caccgaccgc     420

gcactcgacc agggtgtgag gttggccgac gagctgggcg ttacgaacaa tgcctctatc     480

ctgggattgg ccggtatggc cttccagatg ggcgaaggac gtgcccggca gttccgtaac     540
```

```
accttccagg cgatcaagga tcgcaacaag gaagccttcg aggctggtgt gcgaaacagc    600

aagtggtaca cgcagacgcc caccggggcc gaggcattca tcaagcgcat ggcgccccac    660

ttcgatacac cgagtcaaat cggtgtcgat tggtacagcg ccgcaacagc ggagcgccgt    720

cgcgcgtccc tgatggtgct ggtcgccata ggcaccgccg tgacagcggc cgtcaaccct    780

ggcgtcgtgg tcaggcgccg tcgctaa                                        807


<210> SEQ ID NO 9
<211> LENGTH: 268
<212> TYPE: PRT
<213> ORGANISM: Artificial Sequence
<220> FEATURE:
<223> OTHER INFORMATION: synthetic chimeric P225 construct, GP36 segment
      linked to BPI segment, vector seq-GP36 muralytic domain-RRR-BPI
      TMD-RRR
<220> FEATURE:
<221> NAME/KEY: DOMAIN
<222> LOCATION: (1)...(22)
<223> OTHER INFORMATION: Part 1 N terminal extension including poly His
      for purification
<220> FEATURE:
<221> NAME/KEY: DOMAIN
<222> LOCATION: (23)...(238)
<223> OTHER INFORMATION: Part 2 GP36 muralytic fragment domain segment
<220> FEATURE:
<221> NAME/KEY: DOMAIN
<222> LOCATION: (239)...(268)
<223> OTHER INFORMATION: Part 3 linker (RRR) with BPI TMD domain segment
      with RRR C terminus

<400> SEQUENCE: 9

Met Gly His His His His His His His His His His Ser Ser Gly His
 1               5                   10                  15

Ile Glu Gly Arg His Met Gly Val Ala Leu Asp Arg Thr Arg Val Asp
            20                  25                  30

Pro Gln Ala Val Gly Asn Glu Val Leu Lys Arg Asn Ala Asp Lys Leu
        35                  40                  45

Asn Ala Met Arg Gly Ala Glu Tyr Gly Ala Asn Val Lys Val Ser Gly
    50                  55                  60

Thr Asp Ile Arg Met Asn Gly Gly Asn Ser Ala Gly Met Leu Lys Gln
65                  70                  75                  80

Asp Val Phe Asn Trp Arg Lys Glu Leu Ala Gln Phe Glu Ala Tyr Arg
                85                  90                  95

Gly Glu Ala Tyr Lys Asp Ala Asp Gly Tyr Ser Val Gly Leu Gly His
            100                 105                 110

Tyr Leu Gly Ser Gly Asn Ala Gly Ala Gly Thr Thr Val Thr Pro Glu
        115                 120                 125

Gln Ala Ala Gln Trp Phe Ala Glu Asp Thr Asp Arg Ala Leu Asp Gln
    130                 135                 140

Gly Val Arg Leu Ala Asp Glu Leu Gly Val Thr Asn Asn Ala Ser Ile
145                 150                 155                 160

Leu Gly Leu Ala Gly Met Ala Phe Gln Met Gly Glu Gly Arg Ala Arg
                165                 170                 175

Gln Phe Arg Asn Thr Phe Gln Ala Ile Lys Asp Arg Asn Lys Glu Ala
            180                 185                 190

Phe Glu Ala Gly Val Arg Asn Ser Lys Trp Tyr Thr Gln Thr Pro Thr
        195                 200                 205

Gly Ala Glu Ala Phe Ile Lys Arg Met Ala Pro His Phe Asp Thr Pro
    210                 215                 220

Ser Gln Ile Gly Val Asp Trp Tyr Ser Ala Ala Thr Ala Glu Arg Arg
```

-continued 225 230 235 240

Arg Ala Ser Leu Met Val Leu Val Ala Ile Gly Thr Ala Val Thr Ala
245 250 255

Ala Val Asn Pro Gly Val Val Val Arg Arg Arg Arg
260 265

<210> SEQ ID NO 10
<211> LENGTH: 765
<212> TYPE: DNA
<213> ORGANISM: Artificial Sequence
<220> FEATURE:
<223> OTHER INFORMATION: synthetic chimeric P266 construct, GP36 segment linked to BPI MTD segment, P225 variant, 6xHis tag-GP36 CD-RRR-BPI TMD-RRR, vector seq-his6-GP36 muralytic domain-RRR-BPI TMD-RRR
<220> FEATURE:
<221> NAME/KEY: misc_feature
<222> LOCATION: (1)...(6)
<223> OTHER INFORMATION: start codon and bases generated due to cloning enzyme (NheI) site
<220> FEATURE:
<221> NAME/KEY: misc_feature
<222> LOCATION: (7)...(24)
<223> OTHER INFORMATION: 6xHis tag
<220> FEATURE:
<221> NAME/KEY: misc_feature
<222> LOCATION: (25)...(672)
<223> OTHER INFORMATION: GP36 catalytic (muralytic) domain (CD)
<220> FEATURE:
<221> NAME/KEY: misc_feature
<222> LOCATION: (673)...(681)
<223> OTHER INFORMATION: linker arginines (RRR)
<220> FEATURE:
<221> NAME/KEY: misc_feature
<222> LOCATION: (682)...(753)
<223> OTHER INFORMATION: BPI MTD
<220> FEATURE:
<221> NAME/KEY: misc_feature
<222> LOCATION: (754)...(762)
<223> OTHER INFORMATION: N-terminal arginines (RRR)
<220> FEATURE:
<221> NAME/KEY: misc_feature
<222> LOCATION: (763)...(765)
<223> OTHER INFORMATION: stop codon

<400> SEQUENCE: 10
atgggccatc atcatcatca tcatggtgta gctcttgatc gcacgcgggt tgatccccag 60
gcagtcggca acgaggtgct caagcgcaac gcggataagc tgaatgcgat gcggggcgcc 120
gagtacggtg ccaacgtcaa ggtcagcggc acggacattc gcatgaacgg gggtaacagt 180
gccggcatgc tgaagcagga cgtgttcaac tggcggaagg aactggctca gttcgaggct 240
taccgagggg aggcgtataa ggatgccgat ggttatagtg tgggcctggg gcattacctg 300
ggcagtggca atgctggggc aggtactaca gtcacgcctg agcaagccgc gcagtggttc 360
gccgaggaca ccgaccgcgc actcgaccag ggtgtgaggt tggccgacga gctgggcgtt 420
acgaacaatg cctctatcct gggattggcc ggtatggcct tccagatggg cgaaggacgt 480
gcccggcagt tccgtaacac cttccaggcg atcaaggatc gcaacaagga agccttcgag 540
gctggtgtgc gaaacagcaa gtggtacacg cagacgccca accgggccga ggcattcatc 600
aagcgcatgg cgccccactt cgatacaccg agtcaaatcg gtgtcgattg gtacagcgcc 660
gcaacagcgg agcgccgtcg cgcgtccctg atggtgctgg tcgccatagg caccgccgtg 720
acagcggccg tcaaccctgg cgtcgtggtc aggcgccgtc gctga 765

<210> SEQ ID NO 11
<211> LENGTH: 254
<212> TYPE: PRT

-continued

<213> ORGANISM: Artificial Sequence
<220> FEATURE:
<223> OTHER INFORMATION: synthetic chimeric P266 construct, GP36 segment linked to BPI MTD segment, P225 variant, 6xHis tag-GP36 CD-RRR-BPI TMD-RRR, vector seq-his6-GP36 muralytic domain-RRR-BPI TMD-RRR
<220> FEATURE:
<221> NAME/KEY: SITE
<222> LOCATION: (1)...(2)
<223> OTHER INFORMATION: start codon and amino acid generated due to cloning enzyme (NheI) site
<220> FEATURE:
<221> NAME/KEY: DOMAIN
<222> LOCATION: (3)...(8)
<223> OTHER INFORMATION: 6xHis tag
<220> FEATURE:
<221> NAME/KEY: DOMAIN
<222> LOCATION: (9)...(224)
<223> OTHER INFORMATION: GP36 catalytic (muralytic) domain (CD)
<220> FEATURE:
<221> NAME/KEY: DOMAIN
<222> LOCATION: (225)...(227)
<223> OTHER INFORMATION: linker arginines (RRR)
<220> FEATURE:
<221> NAME/KEY: DOMAIN
<222> LOCATION: (228)...(251)
<223> OTHER INFORMATION: BPI MTD
<220> FEATURE:
<221> NAME/KEY: DOMAIN
<222> LOCATION: (252)...(254)
<223> OTHER INFORMATION: N-terminal arginines (RRR)

<400> SEQUENCE: 11

```
Met Gly His His His His His His Gly Val Ala Leu Asp Arg Thr Arg
 1               5                  10                  15

Val Asp Pro Gln Ala Val Gly Asn Glu Val Leu Lys Arg Asn Ala Asp
            20                  25                  30

Lys Leu Asn Ala Met Arg Gly Ala Glu Tyr Gly Ala Asn Val Lys Val
        35                  40                  45

Ser Gly Thr Asp Ile Arg Met Asn Gly Gly Asn Ser Ala Gly Met Leu
    50                  55                  60

Lys Gln Asp Val Phe Asn Trp Arg Lys Glu Leu Ala Gln Phe Glu Ala
65                  70                  75                  80

Tyr Arg Gly Glu Ala Tyr Lys Asp Ala Asp Gly Tyr Ser Val Gly Leu
                85                  90                  95

Gly His Tyr Leu Gly Ser Gly Asn Ala Gly Ala Gly Thr Thr Val Thr
            100                 105                 110

Pro Glu Gln Ala Ala Gln Trp Phe Ala Glu Asp Thr Asp Arg Ala Leu
        115                 120                 125

Asp Gln Gly Val Arg Leu Ala Asp Glu Leu Gly Val Thr Asn Asn Ala
    130                 135                 140

Ser Ile Leu Gly Leu Ala Gly Met Ala Phe Gln Met Gly Glu Gly Arg
145                 150                 155                 160

Ala Arg Gln Phe Arg Asn Thr Phe Gln Ala Ile Lys Asp Arg Asn Lys
                165                 170                 175

Glu Ala Phe Glu Ala Gly Val Arg Asn Ser Lys Trp Tyr Thr Gln Thr
            180                 185                 190

Pro Thr Gly Ala Glu Ala Phe Ile Lys Arg Met Ala Pro His Phe Asp
        195                 200                 205

Thr Pro Ser Gln Ile Gly Val Asp Trp Tyr Ser Ala Ala Thr Ala Glu
    210                 215                 220

Arg Arg Arg Ala Ser Leu Met Val Leu Val Ala Ile Gly Thr Ala Val
225                 230                 235                 240

Thr Ala Ala Val Asn Pro Gly Val Val Val Arg Arg Arg Arg
```

245 250

<210> SEQ ID NO 12
<211> LENGTH: 765
<212> TYPE: DNA
<213> ORGANISM: Artificial Sequence
<220> FEATURE:
<223> OTHER INFORMATION: synthetic chimeric P275 construct, soluble P266 variant, BPI domain with V232E, V234D and I236K
<220> FEATURE:
<221> NAME/KEY: misc_feature
<222> LOCATION: (1)...(6)
<223> OTHER INFORMATION: start codon and bases generated due to cloning enzyme (NheI) site
<220> FEATURE:
<221> NAME/KEY: misc_feature
<222> LOCATION: (7)...(24)
<223> OTHER INFORMATION: 6xHis tag
<220> FEATURE:
<221> NAME/KEY: misc_feature
<222> LOCATION: (25)...(672)
<223> OTHER INFORMATION: GP36 catalytic (muralytic) domain (CD)
<220> FEATURE:
<221> NAME/KEY: misc_feature
<222> LOCATION: (673)...(681)
<223> OTHER INFORMATION: linker arginines (RRR)
<220> FEATURE:
<221> NAME/KEY: misc_feature
<222> LOCATION: (682)...(753)
<223> OTHER INFORMATION: BPI MTD
<220> FEATURE:
<221> NAME/KEY: misc_feature
<222> LOCATION: (754)...(762)
<223> OTHER INFORMATION: N-terminal arginines (RRR)
<220> FEATURE:
<221> NAME/KEY: misc_feature
<222> LOCATION: (763)...(765)
<223> OTHER INFORMATION: stop codon

<400> SEQUENCE: 12
atgggccatc atcatcatca tcatggtgta gctcttgatc gcacgcgggt tgatccccag 60
gcagtcggca acgaggtgct caagcgcaac gcggataagc tgaatgcgat gcggggcgcc 120
gagtacggtg ccaacgtcaa ggtcagcggc acggacattc gcatgaacgg gggtaacagt 180
gccggcatgc tgaagcagga cgtgttcaac tggcggaagg aactggctca gttcgaggct 240
taccgagggg aggcgtataa ggatgccgat ggttatagtg tgggcctggg gcattacctg 300
ggcagtggca atgctggggc aggtactaca gtcacgcctg agcaagccgc gcagtggttc 360
gccgaggaca ccgaccgcgc actcgaccag ggtgtgaggt tggccgacga gctgggcgtt 420
acgaacaatg cctctatcct gggattggcc ggtatggcct tccagatggg cgaaggacgt 480
gcccggcagt tccgtaacac cttccaggcg atcaaggatc gcaacaagga agccttcgag 540
gctggtgtgc gaaacagcaa gtggtacacg cagacgccca accgggccga ggcattcatc 600
aagcgcatgg cgccccactt cgatacaccg agtcaaatcg gtgtcgattg gtacagcgcc 660
gcaacagcgg agcgccgtcg cgcgtccctg atggagctgg acgccaaagg caccgccgtg 720
acagcggccg tcaaccctgg cgtcgtggtc aggcgccgtc gctga 765

<210> SEQ ID NO 13
<211> LENGTH: 254
<212> TYPE: PRT
<213> ORGANISM: Artificial Sequence
<220> FEATURE:
<223> OTHER INFORMATION: synthetic chimeric P275 construct, soluble P266 variant, BPI domain with V232E, V234D and I236K
<220> FEATURE:
<221> NAME/KEY: SITE
<222> LOCATION: (1)...(2)

<223> OTHER INFORMATION: start codon and amino acid generated due to cloning enzyme (NheI) site
<220> FEATURE:
<221> NAME/KEY: DOMAIN
<222> LOCATION: (3)...(8)
<223> OTHER INFORMATION: 6xHis tag
<220> FEATURE:
<221> NAME/KEY: DOMAIN
<222> LOCATION: (9)...(224)
<223> OTHER INFORMATION: GP36 catalytic (muralytic) domain (CD)
<220> FEATURE:
<221> NAME/KEY: DOMAIN
<222> LOCATION: (225)...(227)
<223> OTHER INFORMATION: linker arginines (RRR)
<220> FEATURE:
<221> NAME/KEY: DOMAIN
<222> LOCATION: (228)...(251)
<223> OTHER INFORMATION: BPI MTD
<220> FEATURE:
<221> NAME/KEY: DOMAIN
<222> LOCATION: (252)...(254)
<223> OTHER INFORMATION: N-terminal arginines (RRR)

<400> SEQUENCE: 13

```
Met Gly His His His His His His Gly Val Ala Leu Asp Arg Thr Arg
 1               5                  10                  15

Val Asp Pro Gln Ala Val Gly Asn Glu Val Leu Lys Arg Asn Ala Asp
            20                  25                  30

Lys Leu Asn Ala Met Arg Gly Ala Glu Tyr Gly Ala Asn Val Lys Val
        35                  40                  45

Ser Gly Thr Asp Ile Arg Met Asn Gly Gly Asn Ser Ala Gly Met Leu
    50                  55                  60

Lys Gln Asp Val Phe Asn Trp Arg Lys Glu Leu Ala Gln Phe Glu Ala
65                  70                  75                  80

Tyr Arg Gly Glu Ala Tyr Lys Asp Ala Asp Gly Tyr Ser Val Gly Leu
                85                  90                  95

Gly His Tyr Leu Gly Ser Gly Asn Ala Gly Ala Gly Thr Thr Val Thr
            100                 105                 110

Pro Glu Gln Ala Ala Gln Trp Phe Ala Glu Asp Thr Asp Arg Ala Leu
        115                 120                 125

Asp Gln Gly Val Arg Leu Ala Asp Glu Leu Gly Val Thr Asn Asn Ala
    130                 135                 140

Ser Ile Leu Gly Leu Ala Gly Met Ala Phe Gln Met Gly Glu Gly Arg
145                 150                 155                 160

Ala Arg Gln Phe Arg Asn Thr Phe Gln Ala Ile Lys Asp Arg Asn Lys
                165                 170                 175

Glu Ala Phe Glu Ala Gly Val Arg Asn Ser Lys Trp Tyr Thr Gln Thr
            180                 185                 190

Pro Thr Gly Ala Glu Ala Phe Ile Lys Arg Met Ala Pro His Phe Asp
        195                 200                 205

Thr Pro Ser Gln Ile Gly Val Asp Trp Tyr Ser Ala Ala Thr Ala Glu
    210                 215                 220

Arg Arg Arg Ala Ser Leu Met Glu Leu Asp Ala Lys Gly Thr Ala Val
225                 230                 235                 240

Thr Ala Ala Val Asn Pro Gly Val Val Val Arg Arg Arg Arg
                245                 250
```

<210> SEQ ID NO 14
<211> LENGTH: 804
<212> TYPE: DNA
<213> ORGANISM: Artificial Sequence
<220> FEATURE:

<223> OTHER INFORMATION: synthetic chimeric GP36 MD-P134 holin MTD
construct, GP36CD-RRR-P134 holinTMD-RRR,
10xHis-GP36 CD-RRR-P134 holin MTD-RRR
<220> FEATURE:
<221> NAME/KEY: misc_feature
<222> LOCATION: (1)...(66)
<223> OTHER INFORMATION: vector-10xHis
<220> FEATURE:
<221> NAME/KEY: misc_feature
<222> LOCATION: (67)...(714)
<223> OTHER INFORMATION: GP36 muralytic domain
<220> FEATURE:
<221> NAME/KEY: misc_feature
<222> LOCATION: (715)...(723)
<223> OTHER INFORMATION: RRR linker
<220> FEATURE:
<221> NAME/KEY: misc_feature
<222> LOCATION: (724)...(792)
<223> OTHER INFORMATION: P134 holin MTD
<220> FEATURE:
<221> NAME/KEY: misc_feature
<222> LOCATION: (793)...(801)
<223> OTHER INFORMATION: C terminal RRR
<220> FEATURE:
<221> NAME/KEY: misc_feature
<222> LOCATION: (802)...(804)
<223> OTHER INFORMATION: termination codon

<400> SEQUENCE: 14
atgggccatc atcatcatca tcatcatcat catcacagca gcggccatat cgaaggtcgt 60
catatgggtg tggccctgga ccgcacgcgg gttgatcccc aggcagtcgg caacgaggtg 120
ctcaagcgca acgcggataa gctgaatgcg atgcggggcg ccgagtacgg tgccaacgtc 180
aaggtcagcg gcacggacat tcgcatgaac gggggtaaca gtgccggcat gctgaagcag 240
gacgtgttca actggcggaa ggaactggct cagttcgagg cttaccgagg ggaggcgtat 300
aaggatgccg atggttatag tgtgggcctg gggcattacc tgggcagtgg caatgctggg 360
gcaggtacta cagtcacgcc tgagcaagcc gcgcagtggt tcgccgagga caccgaccgc 420
gcactcgacc agggtgtgag gttggccgac gagctgggcg ttacgaacaa tgcctctatc 480
ctgggattgg ccggtatggc cttccagatg ggcgaaggac gtgcccggca gttccgtaac 540
accttccagg cgatcaagga tcgcaacaag gaagccttcg aggctggtgt gcgaaacagc 600
aagtggtaca cgcagacgcc caccggggcc gaggcattca tcaagcgcat ggcgccccac 660
ttcgatacac cgagtcaaat cggtgtcgat tggtacagcg ccgcaacagc ggagcgccgt 720
cgcgagatcg ccagcctctg tgctgcggta ctcaccgcgc tctacgtggg cgcccagctc 780
atcaccctgc tccgccgtcg ctga 804

<210> SEQ ID NO 15
<211> LENGTH: 267
<212> TYPE: PRT
<213> ORGANISM: Artificial Sequence
<220> FEATURE:
<223> OTHER INFORMATION: synthetic chimeric GP36 MD-P134 holin MTD
construct, GP36CD-RRR-P134 holinTMD-RRR,
10xHis-GP36 CD-RRR-P134 holin MTD-RRR
<220> FEATURE:
<221> NAME/KEY: DOMAIN
<222> LOCATION: (1)...(22)
<223> OTHER INFORMATION: vector-10xHis
<220> FEATURE:
<221> NAME/KEY: DOMAIN
<222> LOCATION: (23)...(238)
<223> OTHER INFORMATION: GP36 muralytic domain
<220> FEATURE:
<221> NAME/KEY: DOMAIN
<222> LOCATION: (239)...(241)
<223> OTHER INFORMATION: RRR linker
<220> FEATURE:
<221> NAME/KEY: DOMAIN
<222> LOCATION: (242)...(264)
<223> OTHER INFORMATION: P134 holin MTD
<220> FEATURE:
<221> NAME/KEY: DOMAIN
<222> LOCATION: (265)...(267)
<223> OTHER INFORMATION: C terminal RRR

<400> SEQUENCE: 15

```
Met Gly His His His His His His His His His His Ser Ser Gly His
 1               5                  10                  15

Ile Glu Gly Arg His Met Gly Val Ala Leu Asp Arg Thr Arg Val Asp
            20                  25                  30

Pro Gln Ala Val Gly Asn Glu Val Leu Lys Arg Asn Ala Asp Lys Leu
        35                  40                  45

Asn Ala Met Arg Gly Ala Glu Tyr Gly Ala Asn Val Lys Val Ser Gly
    50                  55                  60

Thr Asp Ile Arg Met Asn Gly Gly Asn Ser Ala Gly Met Leu Lys Gln
65                  70                  75                  80

Asp Val Phe Asn Trp Arg Lys Glu Leu Ala Gln Phe Glu Ala Tyr Arg
                85                  90                  95

Gly Glu Ala Tyr Lys Asp Ala Asp Gly Tyr Ser Val Gly Leu Gly His
            100                 105                 110

Tyr Leu Gly Ser Gly Asn Ala Gly Ala Gly Thr Thr Val Thr Pro Glu
        115                 120                 125

Gln Ala Ala Gln Trp Phe Ala Glu Asp Thr Asp Arg Ala Leu Asp Gln
    130                 135                 140

Gly Val Arg Leu Ala Asp Glu Leu Gly Val Thr Asn Asn Ala Ser Ile
145                 150                 155                 160

Leu Gly Leu Ala Gly Met Ala Phe Gln Met Gly Glu Gly Arg Ala Arg
                165                 170                 175

Gln Phe Arg Asn Thr Phe Gln Ala Ile Lys Asp Arg Asn Lys Glu Ala
            180                 185                 190

Phe Glu Ala Gly Val Arg Asn Ser Lys Trp Tyr Thr Gln Thr Pro Thr
        195                 200                 205

Gly Ala Glu Ala Phe Ile Lys Arg Met Ala Pro His Phe Asp Thr Pro
    210                 215                 220

Ser Gln Ile Gly Val Asp Trp Tyr Ser Ala Ala Thr Ala Glu Arg Arg
225                 230                 235                 240

Arg Glu Ile Ala Ser Leu Cys Ala Ala Val Leu Thr Ala Leu Tyr Val
                245                 250                 255

Gly Ala Gln Leu Ile Thr Leu Leu Arg Arg Arg
            260                 265
```

<210> SEQ ID NO 16
<211> LENGTH: 825
<212> TYPE: DNA
<213> ORGANISM: Artificial Sequence
<220> FEATURE:
<223> OTHER INFORMATION: synthetic chimeric GP36 MD-lipopolysaccharide
      binding protein MTD construct, GP36CD-RRR-LBP
      peptide-RRR, 10xHis-GP36 CD-RRR-LPS BP peptide-RRR
<220> FEATURE:
<221> NAME/KEY: misc_feature
<222> LOCATION: (1)...(3)
<223> OTHER INFORMATION: initiation Met
<220> FEATURE:
<221> NAME/KEY: misc_feature
<222> LOCATION: (4)...(66)
<223> OTHER INFORMATION: vector segment-10xHis
<220> FEATURE:
<221> NAME/KEY: misc_feature
<222> LOCATION: (67)...(714)
<223> OTHER INFORMATION: GP36 muralytic domain
<220> FEATURE:
<221> NAME/KEY: misc_feature
<222> LOCATION: (715)...(723)
<223> OTHER INFORMATION: RRR linker
<220> FEATURE:
<221> NAME/KEY: misc_feature
<222> LOCATION: (724)...(813)
<223> OTHER INFORMATION: LPS BP MTD
<220> FEATURE:
<221> NAME/KEY: misc_feature
<222> LOCATION: (814)...(822)
<223> OTHER INFORMATION: C terminal RRR
<220> FEATURE:
<221> NAME/KEY: misc_feature
<222> LOCATION: (823)...(825)
<223> OTHER INFORMATION: termination codon

<400> SEQUENCE: 16
atgggccatc atcatcatca tcatcatcat catcacagca gcggccatat cgaaggtcgt 60
catatgggtg tggccctgga ccgcacgcgg gttgatcccc aggcagtcgg caacgaggtg 120
ctcaagcgca acgcggataa gctgaatgcg atgcggggcg ccgagtacgg tgccaacgtc 180
aaggtcagcg gcacggacat tcgcatgaac gggggtaaca gtgccggcat gctgaagcag 240
gacgtgttca actggcggaa ggaactggct cagttcgagg cttaccgagg ggaggcgtat 300
aaggatgccg atggttatag tgtgggcctg ggcattacc tgggcagtgg caatgctggg 360
gcaggtacta cagtcacgcc tgagcaagcc gcgcagtggt tcgccgagga caccgaccgc 420
gcactcgacc agggtgtgag gttggccgac gagctgggcg ttacgaacaa tgcctctatc 480
ctgggattgg ccggtatggc cttccagatg ggcgaaggac gtgcccggca gttccgtaac 540
accttccagg cgatcaagga tcgcaacaag gaagccttcg aggctggtgt gcgaaacagc 600
aagtggtaca cgcagacgcc caccggggcc gaggcattca tcaagcgcat ggcgccccac 660
ttcgatacac cgagtcaaat cggtgtcgat tggtacagcg ccgcaacagc ggagcgccgt 720
cgctccgact cctccatccg ggtccagggc cgttggaagg tgcgcgcgtc attcttcaaa 780
ctgcagggct ccttcgatgt cagtgtcaag ggccgccgtc gctga 825

<210> SEQ ID NO 17
<211> LENGTH: 274
<212> TYPE: PRT
<213> ORGANISM: Artificial Sequence
<220> FEATURE:
<223> OTHER INFORMATION: synthetic chimeric GP36 MD-lipopolysaccharide
binding protein MTD construct, GP36CD-RRR-LBP
peptide-RRR, 10xHis-GP36 CD-RRR-LPS BP peptide-RRR
<220> FEATURE:
<221> NAME/KEY: SITE
<222> LOCATION: (1)...(1)
<223> OTHER INFORMATION: initiation Met
<220> FEATURE:
<221> NAME/KEY: DOMAIN
<222> LOCATION: (2)...(22)
<223> OTHER INFORMATION: vector segment-10xHis
<220> FEATURE:
<221> NAME/KEY: DOMAIN
<222> LOCATION: (23)...(238)
<223> OTHER INFORMATION: GP36 muralytic domain
<220> FEATURE:
<221> NAME/KEY: DOMAIN
<222> LOCATION: (239)...(241)
<223> OTHER INFORMATION: RRR linker
<220> FEATURE:
<221> NAME/KEY: DOMAIN
<222> LOCATION: (242)...(271)

```
<223> OTHER INFORMATION: LPS BP MTD
<220> FEATURE:
<221> NAME/KEY: DOMAIN
<222> LOCATION: (272)...(274)
<223> OTHER INFORMATION: C terminal RRR

<400> SEQUENCE: 17

Met Gly His His His His His His His His His His Ser Ser Gly His
 1               5                  10                  15

Ile Glu Gly Arg His Met Gly Val Ala Leu Asp Arg Thr Arg Val Asp
            20                  25                  30

Pro Gln Ala Val Gly Asn Glu Val Leu Lys Arg Asn Ala Asp Lys Leu
        35                  40                  45

Asn Ala Met Arg Gly Ala Glu Tyr Gly Ala Asn Val Lys Val Ser Gly
    50                  55                  60

Thr Asp Ile Arg Met Asn Gly Gly Asn Ser Ala Gly Met Leu Lys Gln
65                  70                  75                  80

Asp Val Phe Asn Trp Arg Lys Glu Leu Ala Gln Phe Glu Ala Tyr Arg
                85                  90                  95

Gly Glu Ala Tyr Lys Asp Ala Asp Gly Tyr Ser Val Gly Leu Gly His
            100                 105                 110

Tyr Leu Gly Ser Gly Asn Ala Gly Ala Gly Thr Thr Val Thr Pro Glu
        115                 120                 125

Gln Ala Ala Gln Trp Phe Ala Glu Asp Thr Asp Arg Ala Leu Asp Gln
    130                 135                 140

Gly Val Arg Leu Ala Asp Glu Leu Gly Val Thr Asn Asn Ala Ser Ile
145                 150                 155                 160

Leu Gly Leu Ala Gly Met Ala Phe Gln Met Gly Glu Gly Arg Ala Arg
                165                 170                 175

Gln Phe Arg Asn Thr Phe Gln Ala Ile Lys Asp Arg Asn Lys Glu Ala
            180                 185                 190

Phe Glu Ala Gly Val Arg Asn Ser Lys Trp Tyr Thr Gln Thr Pro Thr
        195                 200                 205

Gly Ala Glu Ala Phe Ile Lys Arg Met Ala Pro His Phe Asp Thr Pro
    210                 215                 220

Ser Gln Ile Gly Val Asp Trp Tyr Ser Ala Ala Thr Ala Glu Arg Arg
225                 230                 235                 240

Arg Ser Asp Ser Ser Ile Arg Val Gln Gly Arg Trp Lys Val Arg Ala
                245                 250                 255

Ser Phe Phe Lys Leu Gln Gly Ser Phe Asp Val Ser Val Lys Gly Arg
            260                 265                 270

Arg Arg


<210> SEQ ID NO 18
<211> LENGTH: 1245
<212> TYPE: DNA
<213> ORGANISM: Artificial Sequence
<220> FEATURE:
<223> OTHER INFORMATION: synthetic chimeric GP36 MD-T4 phage, gp5 beta
      helix MTD construct, GP36 CD-T4 phage gp5 beta helix-LE-6xHis
<220> FEATURE:
<221> NAME/KEY: misc_feature
<222> LOCATION: (1)...(3)
<223> OTHER INFORMATION: initiation Met
<220> FEATURE:
<221> NAME/KEY: misc_feature
<222> LOCATION: (4)...(651)
<223> OTHER INFORMATION: GP36 muralytic domain
<220> FEATURE:
<221> NAME/KEY: misc_feature
```

<222> LOCATION: (652)...(657)
<223> OTHER INFORMATION: KL generated by restriction enzyme site HindIII
<220> FEATURE:
<221> NAME/KEY: misc_feature
<222> LOCATION: (658)...(1218)
<223> OTHER INFORMATION: T4 phage gp5 beta-helix
<220> FEATURE:
<221> NAME/KEY: misc_feature
<222> LOCATION: (1219)...(1224)
<223> OTHER INFORMATION: LE generated by restriction enzyme site XhoI
<220> FEATURE:
<221> NAME/KEY: misc_feature
<222> LOCATION: (1225)...(1242)
<223> OTHER INFORMATION: 6xHis
<220> FEATURE:
<221> NAME/KEY: misc_feature
<222> LOCATION: (1243)...(1245)
<223> OTHER INFORMATION: termination codon

<400> SEQUENCE: 18

```
atgggtgtgg ccctggaccg cacgcgggtt gatccccagg cagtcggcaa cgaggtgctc     60

aagcgcaacg cggataagct gaatgcgatg cggggcgccg agtacggtgc caacgtcaag    120

gtcagcggca cggacattcg catgaacggg ggtaacagtg ccggcatgct gaagcaggac    180

gtgttcaact ggcggaagga actggctcag ttcgaggctt accgaggggga ggcgtataag   240

gatgccgatg gttatagtgt gggcctgggg cattacctgg gcagtggcaa tgctggggca    300

ggtactacag tcacgcctga gcaagccgcg cagtggttcg ccgaggacac cgaccgcgca    360

ctcgaccagg gtgtgaggtt ggccgacgag ctgggcgtta cgaacaatgc ctctatcctg    420

ggattggccg gtatggcctt ccagatgggc gaaggacgtg cccggcagtt ccgtaacacc    480

ttccaggcga tcaaggatcg caacaaggaa gccttcgagg ctggtgtgcg aaacagcaag    540

tggtacacgc agacgcccaa ccgggccgag gcattcatca agcgcatggc gccccacttc    600

gatacaccga gtcaaatcgg tgtcgattgg tacagcgccg caacagcgga gaagctttat    660

gtgcatacaa tggaaactga aagcggacat attcaggaat ttgatgatac ccctgggcaa    720

gaacgatata gattagttca tccaactgga acttatgaag aagtatcacc atcaggaaga    780

agaacaagaa aaactgttga taatttgtat gatataacca atgctgatgg taattttttg    840

gtagccggtg ataaaaagac taacgtcggt ggttcagaaa tttattataa catggataat    900

cgtttacatc aaatcgatgg aagcaataca atatttgtac gtggagacga aacgaaaact    960

gttgaaggta atggaactat cctagttaaa ggtaatgtta ctattatagt tgaaggtaat   1020

gctgacatta cagttaaagg agatgctacc actttagttg aaggaaatca aactaacaca   1080

gtaaatggaa atctttcttg gaaagttgcc gggacagttg attgggatgt cggtggtgat   1140

tggacagaaa aaatggcatc tatgagttct atttcatctg gtcaatacac aattgatgga   1200

tcgaggattg acattggcct cgagcaccac caccaccacc actaa                   1245
```

<210> SEQ ID NO 19
<211> LENGTH: 414
<212> TYPE: PRT
<213> ORGANISM: Artificial Sequence
<220> FEATURE:
<223> OTHER INFORMATION: synthetic chimeric GP36 MD-T4 phage, gp5 beta
helix MTD construct, GP36 CD-T4 phage gp5 beta helix-LE-6xHis
<220> FEATURE:
<221> NAME/KEY: SITE
<222> LOCATION: (1)...(1)
<223> OTHER INFORMATION: initiation Met
<220> FEATURE:
<221> NAME/KEY: DOMAIN
<222> LOCATION: (2)...(217)
<223> OTHER INFORMATION: GP36 muralytic domain -continued
<220> FEATURE:
<221> NAME/KEY: SITE
<222> LOCATION: (218)...(219)
<223> OTHER INFORMATION: KL generated by restriction enzyme site HindIII
<220> FEATURE:
<221> NAME/KEY: DOMAIN
<222> LOCATION: (220)...(406)
<223> OTHER INFORMATION: T4 phage gp5 beta-helix
<220> FEATURE:
<221> NAME/KEY: SITE
<222> LOCATION: (407)...(408)
<223> OTHER INFORMATION: LE generated by restriction enzyme site XhoI
<220> FEATURE:
<221> NAME/KEY: DOMAIN
<222> LOCATION: (409)...(414)
<223> OTHER INFORMATION: 6xHis

<400> SEQUENCE: 19

```
Met Gly Val Ala Leu Asp Arg Thr Arg Val Asp Pro Gln Ala Val Gly
 1               5                  10                  15

Asn Glu Val Leu Lys Arg Asn Ala Asp Lys Leu Asn Ala Met Arg Gly
            20                  25                  30

Ala Glu Tyr Gly Ala Asn Val Lys Val Ser Gly Thr Asp Ile Arg Met
        35                  40                  45

Asn Gly Gly Asn Ser Ala Gly Met Leu Lys Gln Asp Val Phe Asn Trp
    50                  55                  60

Arg Lys Glu Leu Ala Gln Phe Glu Ala Tyr Arg Gly Glu Ala Tyr Lys
65                  70                  75                  80

Asp Ala Asp Gly Tyr Ser Val Gly Leu Gly His Tyr Leu Gly Ser Gly
                85                  90                  95

Asn Ala Gly Ala Gly Thr Thr Val Thr Pro Glu Gln Ala Ala Gln Trp
            100                 105                 110

Phe Ala Glu Asp Thr Asp Arg Ala Leu Asp Gln Gly Val Arg Leu Ala
        115                 120                 125

Asp Glu Leu Gly Val Thr Asn Asn Ala Ser Ile Leu Gly Leu Ala Gly
    130                 135                 140

Met Ala Phe Gln Met Gly Glu Gly Arg Ala Arg Gln Phe Arg Asn Thr
145                 150                 155                 160

Phe Gln Ala Ile Lys Asp Arg Asn Lys Glu Ala Phe Glu Ala Gly Val
                165                 170                 175

Arg Asn Ser Lys Trp Tyr Thr Gln Thr Pro Asn Arg Ala Glu Ala Phe
            180                 185                 190

Ile Lys Arg Met Ala Pro His Phe Asp Thr Pro Ser Gln Ile Gly Val
        195                 200                 205

Asp Trp Tyr Ser Ala Ala Thr Ala Glu Lys Leu Tyr Val His Thr Met
    210                 215                 220

Glu Thr Glu Ser Gly His Ile Gln Glu Phe Asp Asp Thr Pro Gly Gln
225                 230                 235                 240

Glu Arg Tyr Arg Leu Val His Pro Thr Gly Thr Tyr Glu Glu Val Ser
                245                 250                 255

Pro Ser Gly Arg Arg Thr Arg Lys Thr Val Asp Asn Leu Tyr Asp Ile
            260                 265                 270

Thr Asn Ala Asp Gly Asn Phe Leu Val Ala Gly Asp Lys Lys Thr Asn
        275                 280                 285

Val Gly Gly Ser Glu Ile Tyr Tyr Asn Met Asp Asn Arg Leu His Gln
    290                 295                 300

Ile Asp Gly Ser Asn Thr Ile Phe Val Arg Gly Asp Glu Thr Lys Thr
305                 310                 315                 320
```

-continued

```
Val Glu Gly Asn Gly Thr Ile Leu Val Lys Gly Asn Val Thr Ile Ile
                325                 330                 335

Val Glu Gly Asn Ala Asp Ile Thr Val Lys Gly Asp Ala Thr Thr Leu
            340                 345                 350

Val Glu Gly Asn Gln Thr Asn Thr Val Asn Gly Asn Leu Ser Trp Lys
        355                 360                 365

Val Ala Gly Thr Val Asp Trp Asp Val Gly Gly Asp Trp Thr Glu Lys
    370                 375                 380

Met Ala Ser Met Ser Ser Ile Ser Ser Gly Gln Tyr Thr Ile Asp Gly
385                 390                 395                 400

Ser Arg Ile Asp Ile Gly Leu Glu His His His His His His
                405                 410
```

<210> SEQ ID NO 20
<211> LENGTH: 1227
<212> TYPE: DNA
<213> ORGANISM: Artificial Sequence
<220> FEATURE:
<223> OTHER INFORMATION: synthetic chimeric GP36 MD-S type pyocin outer membrane translocation (OMT) domain construct, GP36 CD-S type pyocin OM binding domain-LE-6xHis
<220> FEATURE:
<221> NAME/KEY: misc_feature
<222> LOCATION: (1)...(3)
<223> OTHER INFORMATION: initiation Met
<220> FEATURE:
<221> NAME/KEY: misc_feature
<222> LOCATION: (4)...(651)
<223> OTHER INFORMATION: GP36 muralytic domain
<220> FEATURE:
<221> NAME/KEY: misc_feature
<222> LOCATION: (652)...(657)
<223> OTHER INFORMATION: KL generated by restriction enzyme site HindIII
<220> FEATURE:
<221> NAME/KEY: misc_feature
<222> LOCATION: (658)...(1200)
<223> OTHER INFORMATION: S type pyocin OM translocation domain
<220> FEATURE:
<221> NAME/KEY: misc_feature
<222> LOCATION: (1201)...(1206)
<223> OTHER INFORMATION: LE generated by restriction enzyme site XhoI
<220> FEATURE:
<221> NAME/KEY: misc_feature
<222> LOCATION: (1207)...(1224)
<223> OTHER INFORMATION: 6xHis
<220> FEATURE:
<221> NAME/KEY: misc_feature
<222> LOCATION: (1225)...(1227)
<223> OTHER INFORMATION: termination codon

<400> SEQUENCE: 20

```
atgggtgtgg ccctggaccg cacgcgggtt gatccccagg cagtcggcaa cgaggtgctc      60

aagcgcaacg cggataagct gaatgcgatg cggggcgccg agtacggtgc caacgtcaag     120

gtcagcggca cggacattcg catgaacggg ggtaacagtg ccggcatgct gaagcaggac     180

gtgttcaact ggcggaagga actggctcag ttcgaggctt accgaggggga ggcgtataag     240

gatgccgatg gttatagtgt gggcctgggg cattacctgg gcagtggcaa tgctggggca     300

ggtactacag tcacgcctga gcaagccgcg cagtggttcg ccgaggacac cgaccgcgca     360

ctcgaccagg gtgtgaggtt ggccgacgag ctgggcgtta cgaacaatgc ctctatcctg     420

ggattggccg gtatggcctt ccagatgggc gaaggacgtg cccggcagtt ccgtaacacc     480

ttccaggcga tcaaggatcg caacaaggaa gccttcgagg ctggtgtgcg aaacagcaag     540

tggtacacgc agacgcccaa ccgggccgag gcattcatca agcgcatggc gccccacttc     600

gatacaccga gtcaaatcgg tgtcgattgg tacagcgccg caacagcgga gaagcttcaa     660
```

```
gcgttgcaag atgctattaa atttactgcc gacttttata aggaagtaac tgagaaattt    720

ggcgcacgaa catcggagat ggcgcgccaa ctggccgaag gcgccagggg gaaaaatatc    780

aggagttcgg cggaagcaat caagtcgttt gaaaagcaca aggatgcgtt aaataaaaaa    840

cttagcctta aagataggca agccattgcc aaagcctttg attctctaga caagcagatg    900

atggcgaaga gccttgagaa atttagcaaa ggctttggag ttgtaggcaa agctattgac    960

gccgccagcc tgtaccaaga gttcaagata tctacggaaa ccggggactg gaaaccattc   1020

tttgtaaaaa ttgaaacact agctgctggt gcggccgcca gttggcttgt gggtattgca   1080

tttgccacgg caacagccac tcctataggc attctggggt tcgcactggt aatggcagtt   1140

accggggcga tgattgacga agaccttcta gaaaaagcaa acaatcttgt aatatccatt   1200

ctcgagcacc accaccacca ccactaa                                       1227
```

<210> SEQ ID NO 21
<211> LENGTH: 408
<212> TYPE: PRT
<213> ORGANISM: Artificial Sequence
<220> FEATURE:
<223> OTHER INFORMATION: synthetic chimeric GP36 MD-S type pyocin outer membrane translocation (OMT) domain construct, GP36 CD-S type pyocin OM binding domain-LE-6xHis
<220> FEATURE:
<221> NAME/KEY: SITE
<222> LOCATION: (1)...(1)
<223> OTHER INFORMATION: initiation Met
<220> FEATURE:
<221> NAME/KEY: DOMAIN
<222> LOCATION: (2)...(217)
<223> OTHER INFORMATION: GP36 muralytic domain
<220> FEATURE:
<221> NAME/KEY: SITE
<222> LOCATION: (218)...(219)
<223> OTHER INFORMATION: KL generated by restriction enzyme site HindIII
<220> FEATURE:
<221> NAME/KEY: DOMAIN
<222> LOCATION: (220)...(400)
<223> OTHER INFORMATION: S type pyocin OM translocation domain
<220> FEATURE:
<221> NAME/KEY: SITE
<222> LOCATION: (401)...(402)
<223> OTHER INFORMATION: LE generated by restriction enzyme site XhoI
<220> FEATURE:
<221> NAME/KEY: DOMAIN
<222> LOCATION: (403)...(408)
<223> OTHER INFORMATION: 6xHis

<400> SEQUENCE: 21

```
Met Gly Val Ala Leu Asp Arg Thr Arg Val Asp Pro Gln Ala Val Gly
 1               5                  10                  15

Asn Glu Val Leu Lys Arg Asn Ala Asp Lys Leu Asn Ala Met Arg Gly
            20                  25                  30

Ala Glu Tyr Gly Ala Asn Val Lys Val Ser Gly Thr Asp Ile Arg Met
        35                  40                  45

Asn Gly Gly Asn Ser Ala Gly Met Leu Lys Gln Asp Val Phe Asn Trp
    50                  55                  60

Arg Lys Glu Leu Ala Gln Phe Glu Ala Tyr Arg Gly Glu Ala Tyr Lys
65                  70                  75                  80

Asp Ala Asp Gly Tyr Ser Val Gly Leu Gly His Tyr Leu Gly Ser Gly
                85                  90                  95

Asn Ala Gly Ala Gly Thr Thr Val Thr Pro Glu Gln Ala Ala Gln Trp
            100                 105                 110

Phe Ala Glu Asp Thr Asp Arg Ala Leu Asp Gln Gly Val Arg Leu Ala
```

```
        115                 120                 125

Asp Glu Leu Gly Val Thr Asn Asn Ala Ser Ile Leu Gly Leu Ala Gly
    130                 135                 140

Met Ala Phe Gln Met Gly Glu Gly Arg Ala Arg Gln Phe Arg Asn Thr
145                 150                 155                 160

Phe Gln Ala Ile Lys Asp Arg Asn Lys Glu Ala Phe Glu Ala Gly Val
                165                 170                 175

Arg Asn Ser Lys Trp Tyr Thr Gln Thr Pro Asn Arg Ala Glu Ala Phe
            180                 185                 190

Ile Lys Arg Met Ala Pro His Phe Asp Thr Pro Ser Gln Ile Gly Val
        195                 200                 205

Asp Trp Tyr Ser Ala Ala Thr Ala Glu Lys Leu Gln Ala Leu Gln Asp
    210                 215                 220

Ala Ile Lys Phe Thr Ala Asp Phe Tyr Lys Glu Val Thr Glu Lys Phe
225                 230                 235                 240

Gly Ala Arg Thr Ser Glu Met Ala Arg Gln Leu Ala Glu Gly Ala Arg
                245                 250                 255

Gly Lys Asn Ile Arg Ser Ser Ala Glu Ala Ile Lys Ser Phe Glu Lys
            260                 265                 270

His Lys Asp Ala Leu Asn Lys Lys Leu Ser Leu Lys Asp Arg Gln Ala
        275                 280                 285

Ile Ala Lys Ala Phe Asp Ser Leu Asp Lys Gln Met Met Ala Lys Ser
    290                 295                 300

Leu Glu Lys Phe Ser Lys Gly Phe Gly Val Val Gly Lys Ala Ile Asp
305                 310                 315                 320

Ala Ala Ser Leu Tyr Gln Glu Phe Lys Ile Ser Thr Glu Thr Gly Asp
                325                 330                 335

Trp Lys Pro Phe Phe Val Lys Ile Glu Thr Leu Ala Ala Gly Ala Ala
            340                 345                 350

Ala Ser Trp Leu Val Gly Ile Ala Phe Ala Thr Ala Thr Ala Thr Pro
        355                 360                 365

Ile Gly Ile Leu Gly Phe Ala Leu Val Met Ala Val Thr Gly Ala Met
    370                 375                 380

Ile Asp Glu Asp Leu Leu Glu Lys Ala Asn Asn Leu Val Ile Ser Ile
385                 390                 395                 400

Leu Glu His His His His His His
                405


<210> SEQ ID NO 22
<211> LENGTH: 2682
<212> TYPE: DNA
<213> ORGANISM: Artificial Sequence
<220> FEATURE:
<223> OTHER INFORMATION: synthetic chimeric GP36 MD-P22 tail spike
      protein MTD construct, GP36 CD-P22 tail spike-LE-6xHis
<220> FEATURE:
<221> NAME/KEY: misc_feature
<222> LOCATION: (1)...(3)
<223> OTHER INFORMATION: initiation Met
<220> FEATURE:
<221> NAME/KEY: misc_feature
<222> LOCATION: (4)...(651)
<223> OTHER INFORMATION: GP36 muralytic domain
<220> FEATURE:
<221> NAME/KEY: misc_feature
<222> LOCATION: (652)...(657)
<223> OTHER INFORMATION: KL generated by restriction enzyme site HindIII
<220> FEATURE:
<221> NAME/KEY: misc_feature
<222> LOCATION: (658)...(2655)
```

<223> OTHER INFORMATION: Enterobacteria phage P22 tail spike protein
      domain
<220> FEATURE:
<221> NAME/KEY: misc_feature
<222> LOCATION: (2656)...(2661)
<223> OTHER INFORMATION: LE generated by restriction enzyme site XhoI
<220> FEATURE:
<221> NAME/KEY: misc_feature
<222> LOCATION: (2662)...(2679)
<223> OTHER INFORMATION: 6xHis
<220> FEATURE:
<221> NAME/KEY: misc_feature
<222> LOCATION: (2680)...(2682)
<223> OTHER INFORMATION: termination codon

<400> SEQUENCE: 22

```
atgggtgtgg ccctggaccg cacgcgggtt gatccccagg cagtcggcaa cgaggtgctc     60
aagcgcaacg cggataagct gaatgcgatg cggggcgccg agtacggtgc caacgtcaag    120
gtcagcggca cggacattcg catgaacggg ggtaacagtg ccggcatgct gaagcaggac    180
gtgttcaact ggcggaagga actggctcag ttcgaggctt accgagggga ggcgtataag    240
gatgccgatg gttatagtgt gggcctgggg cattacctgg gcagtggcaa tgctggggca    300
ggtactacag tcacgcctga gcaagccgcg cagtggttcg ccgaggacac cgaccgcgca    360
ctcgaccagg gtgtgaggtt ggccgacgag ctgggcgtta cgaacaatgc ctctatcctg    420
ggattggccg gtatggcctt ccagatgggc gaaggacgtg cccggcagtt ccgtaacacc    480
ttccaggcga tcaaggatcg caacaaggaa gccttcgagg ctggtgtgcg aaacagcaag    540
tggtacacgc agacgcccaa ccgggccgag gcattcatca agcgcatggc gccccacttc    600
gatacaccga gtcaaatcgg tgtcgattgg tacagcgccg caacagcgga gaagcttaca    660
gacatcactg caaacgtagt tgtttctaac cctcgtccaa tcttcactga atcccgttcg    720
tttaaagctg ttgctaatgg gaaaatttac attggtcaga ttgataccga tccggttaat    780
cctgccaatc agatacccgt atacattgaa aatgaggatg gctctcacgt ccagattact    840
cagccgctaa ttatcaacgc agccggtaaa atcgtataca acggccaact ggtgaaaatt    900
gtcaccgttc agggtcatag catggctatc tatgatgcca atggttctca ggttgactat    960
attgctaacg tattgaagta cgatccagat caatattcaa tagaagctga taaaaaattt   1020
aagtattcag taaaattatc agattatcca acattgcagg atgcagcatc tgctgcggtt   1080
gatggccttc ttatcgatcg agattataat ttttatggtg gagagacagt tgattttggc   1140
ggaaaggttc tgactataga atgtaaagct aaatttatag gagatggaaa tcttattttt   1200
acgaaattag gcaaaggttc ccgcattgcc ggggttttta tggaaagcac tacaacacca   1260
tgggttatca agccttggac ggatgacaat cagtggctaa cggatgccgc agcggtcgtt   1320
gccactttaa aacaatctaa aactgatggg tatcagccaa ccgtaagcga ttacgttaaa   1380
ttcccaggaa tagaaacgtt actcccacct aatgcaaaag ggcaaaacat aacgtctacg   1440
ttagaaatta gagaatgtat aggggtcgaa gttcatcggg ctagcggtct aatggctggt   1500
tttttgttta gagggtgtca cttctgcaag atggtagacg ccaataatcc aagcggaggt   1560
aaagatggca ttataacctt cgaaaacctt agcggcgatt gggggaaggg taactatgtc   1620
attggcggac gaaccagcta tgggtcagta agtagcgccc agtttttacg taataatggt   1680
ggctttgaac gtgatggtgg agttattggg tttacttcat atcgcgctgg ggagagtggc   1740
gttaaaactt ggcaaggtac tgtgggctcg acaacctctc gcaactataa tctgcaattc   1800
cgcgactcgg tcgttattta ccccgtatgg gacggattcg atttaggtgc tgacactgac   1860
```

atgaatccgg agttggacag gccaggggac taccctataa cccaataccc actgcatcag 1920
ttacccctaa atcacctgat tgataatctt ctggttcgcg gggcgttagg tgtaggtttt 1980
ggtatggatg gtaagggcat gtatgtgtct aatattaccg tagaagattg cgctgggtct 2040
ggcgcgtacc tactcaccca cgaatcagta tttaccaata tagccataat tgacaccaat 2100
actaaggatt tccaggcgaa tcagatttat atatctgggg cttgccgtgt gaacggttta 2160
cgtttaattg ggatccgctc aaccgatggg cagggtctaa ccatagacgc ccctaactct 2220
accgtaagcg gtataaccgg gatggtagac ccctctagaa ttaatgttgc taatttggca 2280
gaagaagggt taggtaatat ccgcgctaat agtttcggct atgatagcgc agcgattaaa 2340
ctgcggattc ataagttatc aaagacatta gatagcggag cattgtactc ccacattaac 2400 ggggggccg gttctggctc agcgtatact caacttactg ctatttcagg tagcacacct 2460
gacgctgtat cattaaaagt taaccacaaa gattgcaggg gggcagagat accatttgtt 2520
cctgacatcg cgtcagatga ttttataaag gattcctcat gtttttgcc atattgggaa 2580 aataattcta cttctttaaa ggctttagtg aaaaaaccca atggagaatt agttagatta 2640
accttggcaa cacttctcga gcaccaccac caccaccact ag 2682

<210> SEQ ID NO 23
<211> LENGTH: 893
<212> TYPE: PRT
<213> ORGANISM: Artificial Sequence
<220> FEATURE:
<223> OTHER INFORMATION: synthetic chimeric GP36 MD-P22 tail spike protein MTD construct, GP36 CD-P22 tail spike-LE-6xHis
<220> FEATURE:
<221> NAME/KEY: SITE
<222> LOCATION: (1)...(1)
<223> OTHER INFORMATION: initiation Met
<220> FEATURE:
<221> NAME/KEY: DOMAIN
<222> LOCATION: (2)...(217)
<223> OTHER INFORMATION: GP36 muralytic domain
<220> FEATURE:
<221> NAME/KEY: SITE
<222> LOCATION: (218)...(219)
<223> OTHER INFORMATION: KL generated by restriction enzyme site HindIII
<220> FEATURE:
<221> NAME/KEY: DOMAIN
<222> LOCATION: (220)...(885)
<223> OTHER INFORMATION: Enterobacteria phage P22 tail spike protein domain
<220> FEATURE:
<221> NAME/KEY: SITE
<222> LOCATION: (886)...(887)
<223> OTHER INFORMATION: LE generated by restriction enzyme site XhoI
<220> FEATURE:
<221> NAME/KEY: DOMAIN
<222> LOCATION: (888)...(893)
<223> OTHER INFORMATION: 6xHis

<400> SEQUENCE: 23

Met Gly Val Ala Leu Asp Arg Thr Arg Val Asp Pro Gln Ala Val Gly
1 5 10 15

Asn Glu Val Leu Lys Arg Asn Ala Asp Lys Leu Asn Ala Met Arg Gly
20 25 30

Ala Glu Tyr Gly Ala Asn Val Lys Val Ser Gly Thr Asp Ile Arg Met
35 40 45

Asn Gly Gly Asn Ser Ala Gly Met Leu Lys Gln Asp Val Phe Asn Trp
50 55 60

Arg Lys Glu Leu Ala Gln Phe Glu Ala Tyr Arg Gly Glu Ala Tyr Lys
65 70 75 80

-continued

```
Asp Ala Asp Gly Tyr Ser Val Gly Leu Gly His Tyr Leu Gly Ser Gly
                85                  90                  95

Asn Ala Gly Ala Gly Thr Thr Val Thr Pro Glu Gln Ala Ala Gln Trp
            100                 105                 110

Phe Ala Glu Asp Thr Asp Arg Ala Leu Asp Gln Gly Val Arg Leu Ala
        115                 120                 125

Asp Glu Leu Gly Val Thr Asn Asn Ala Ser Ile Leu Gly Leu Ala Gly
    130                 135                 140

Met Ala Phe Gln Met Gly Glu Gly Arg Ala Arg Gln Phe Arg Asn Thr
145                 150                 155                 160

Phe Gln Ala Ile Lys Asp Arg Asn Lys Glu Ala Phe Glu Ala Gly Val
                165                 170                 175

Arg Asn Ser Lys Trp Tyr Thr Gln Thr Pro Asn Arg Ala Glu Ala Phe
            180                 185                 190

Ile Lys Arg Met Ala Pro His Phe Asp Thr Pro Ser Gln Ile Gly Val
        195                 200                 205

Asp Trp Tyr Ser Ala Ala Thr Ala Glu Lys Leu Thr Asp Ile Thr Ala
    210                 215                 220

Asn Val Val Val Ser Asn Pro Arg Pro Ile Phe Thr Glu Ser Arg Ser
225                 230                 235                 240

Phe Lys Ala Val Ala Asn Gly Lys Ile Tyr Ile Gly Gln Ile Asp Thr
                245                 250                 255

Asp Pro Val Asn Pro Ala Asn Gln Ile Pro Val Tyr Ile Glu Asn Glu
            260                 265                 270

Asp Gly Ser His Val Gln Ile Thr Gln Pro Leu Ile Ile Asn Ala Ala
        275                 280                 285

Gly Lys Ile Val Tyr Asn Gly Gln Leu Val Lys Ile Val Thr Val Gln
    290                 295                 300

Gly His Ser Met Ala Ile Tyr Asp Ala Asn Gly Ser Gln Val Asp Tyr
305                 310                 315                 320

Ile Ala Asn Val Leu Lys Tyr Asp Pro Asp Gln Tyr Ser Ile Glu Ala
                325                 330                 335

Asp Lys Lys Phe Lys Tyr Ser Val Lys Leu Ser Asp Tyr Pro Thr Leu
            340                 345                 350

Gln Asp Ala Ala Ser Ala Ala Val Asp Gly Leu Leu Ile Asp Arg Asp
        355                 360                 365

Tyr Asn Phe Tyr Gly Gly Glu Thr Val Asp Phe Gly Gly Lys Val Leu
    370                 375                 380

Thr Ile Glu Cys Lys Ala Lys Phe Ile Gly Asp Gly Asn Leu Ile Phe
385                 390                 395                 400

Thr Lys Leu Gly Lys Gly Ser Arg Ile Ala Gly Val Phe Met Glu Ser
                405                 410                 415

Thr Thr Thr Pro Trp Val Ile Lys Pro Trp Thr Asp Asp Asn Gln Trp
            420                 425                 430

Leu Thr Asp Ala Ala Ala Val Val Ala Thr Leu Lys Gln Ser Lys Thr
        435                 440                 445

Asp Gly Tyr Gln Pro Thr Val Ser Asp Tyr Val Lys Phe Pro Gly Ile
    450                 455                 460

Glu Thr Leu Leu Pro Pro Asn Ala Lys Gly Gln Asn Ile Thr Ser Thr
465                 470                 475                 480

Leu Glu Ile Arg Glu Cys Ile Gly Val Glu Val His Arg Ala Ser Gly
                485                 490                 495

Leu Met Ala Gly Phe Leu Phe Arg Gly Cys His Phe Cys Lys Met Val
```

-continued

```
            500                 505                 510

Asp Ala Asn Asn Pro Ser Gly Gly Lys Asp Gly Ile Ile Thr Phe Glu
        515                 520                 525

Asn Leu Ser Gly Asp Trp Gly Lys Gly Asn Tyr Val Ile Gly Gly Arg
    530                 535                 540

Thr Ser Tyr Gly Ser Val Ser Ser Ala Gln Phe Leu Arg Asn Asn Gly
545                 550                 555                 560

Gly Phe Glu Arg Asp Gly Gly Val Ile Gly Phe Thr Ser Tyr Arg Ala
                565                 570                 575

Gly Glu Ser Gly Val Lys Thr Trp Gln Gly Thr Val Gly Ser Thr Thr
            580                 585                 590

Ser Arg Asn Tyr Asn Leu Gln Phe Arg Asp Ser Val Val Ile Tyr Pro
        595                 600                 605

Val Trp Asp Gly Phe Asp Leu Gly Ala Asp Thr Asp Met Asn Pro Glu
    610                 615                 620

Leu Asp Arg Pro Gly Asp Tyr Pro Ile Thr Gln Tyr Pro Leu His Gln
625                 630                 635                 640

Leu Pro Leu Asn His Leu Ile Asp Asn Leu Leu Val Arg Gly Ala Leu
                645                 650                 655

Gly Val Gly Phe Gly Met Asp Gly Lys Gly Met Tyr Val Ser Asn Ile
            660                 665                 670

Thr Val Glu Asp Cys Ala Gly Ser Gly Ala Tyr Leu Leu Thr His Glu
        675                 680                 685

Ser Val Phe Thr Asn Ile Ala Ile Ile Asp Thr Asn Thr Lys Asp Phe
    690                 695                 700

Gln Ala Asn Gln Ile Tyr Ile Ser Gly Ala Cys Arg Val Asn Gly Leu
705                 710                 715                 720

Arg Leu Ile Gly Ile Arg Ser Thr Asp Gly Gln Gly Leu Thr Ile Asp
                725                 730                 735

Ala Pro Asn Ser Thr Val Ser Gly Ile Thr Gly Met Val Asp Pro Ser
            740                 745                 750

Arg Ile Asn Val Ala Asn Leu Ala Glu Glu Gly Leu Gly Asn Ile Arg
        755                 760                 765

Ala Asn Ser Phe Gly Tyr Asp Ser Ala Ala Ile Lys Leu Arg Ile His
    770                 775                 780

Lys Leu Ser Lys Thr Leu Asp Ser Gly Ala Leu Tyr Ser His Ile Asn
785                 790                 795                 800

Gly Gly Ala Gly Ser Gly Ser Ala Tyr Thr Gln Leu Thr Ala Ile Ser
                805                 810                 815

Gly Ser Thr Pro Asp Ala Val Ser Leu Lys Val Asn His Lys Asp Cys
            820                 825                 830

Arg Gly Ala Glu Ile Pro Phe Val Pro Asp Ile Ala Ser Asp Asp Phe
        835                 840                 845

Ile Lys Asp Ser Ser Cys Phe Leu Pro Tyr Trp Glu Asn Asn Ser Thr
    850                 855                 860

Ser Leu Lys Ala Leu Val Lys Lys Pro Asn Gly Glu Leu Val Arg Leu
865                 870                 875                 880

Thr Leu Ala Thr Leu Leu Glu His His His His His His
                885                 890
```

<210> SEQ ID NO 24
<211> LENGTH: 6
<212> TYPE: PRT
<213> ORGANISM: Artificial Sequence -continued
<220> FEATURE:
<223> OTHER INFORMATION: synthetic polyhistidine purification tag, six
adjacent histidines, 6xHis, 6 N-proximal His tag

<400> SEQUENCE: 24

His His His His His His
1 5

<210> SEQ ID NO 25
<211> LENGTH: 24
<212> TYPE: PRT
<213> ORGANISM: Artificial Sequence
<220> FEATURE:
<223> OTHER INFORMATION: synthetic wild type BPI TMD

<400> SEQUENCE: 25

Ala Ser Leu Met Val Leu Val Ala Ile Gly Thr Ala Val Thr Ala Ala
1 5 10 15

Val Asn Pro Gly Val Val Val Arg
20

<210> SEQ ID NO 26
<211> LENGTH: 24
<212> TYPE: PRT
<213> ORGANISM: Artificial Sequence
<220> FEATURE:
<223> OTHER INFORMATION: synthetic BPI TMD variant

<400> SEQUENCE: 26

Ala Ser Leu Met Glu Leu Asp Ala Lys Gly Thr Ala Val Thr Ala Ala
1 5 10 15

Val Asn Pro Gly Val Val Val Arg
20

<210> SEQ ID NO 27
<211> LENGTH: 24
<212> TYPE: PRT
<213> ORGANISM: Artificial Sequence
<220> FEATURE:
<223> OTHER INFORMATION: synthetic BPI TMD variant

<400> SEQUENCE: 27

Ala Ser Leu Met Lys Leu Lys Ala Arg Gly Thr Ala Lys Thr Ala Ala
1 5 10 15

Lys Asn Pro Gly Lys Lys Arg Arg
20

<210> SEQ ID NO 28
<211> LENGTH: 24
<212> TYPE: PRT
<213> ORGANISM: Artificial Sequence
<220> FEATURE:
<223> OTHER INFORMATION: synthetic BPI TMD variant

<400> SEQUENCE: 28

Ala Ser Leu Met Lys Leu Lys Ala Arg Gly Thr Ala Lys Thr Ala Ala
1 5 10 15

Lys Asn Pro Gly Lys Val Arg Arg
20

<210> SEQ ID NO 29
<211> LENGTH: 24
<212> TYPE: PRT
<213> ORGANISM: Artificial Sequence
<220> FEATURE:

<223> OTHER INFORMATION: synthetic BPI TMD variant

<400> SEQUENCE: 29

Ala Ser Arg Met Val Leu Val Ala Arg Gly Thr Ala Lys Thr Ala Ala
1 5 10 15

Val Asn Pro Gly Val Val Arg Arg
20

<210> SEQ ID NO 30
<211> LENGTH: 10
<212> TYPE: PRT
<213> ORGANISM: Artificial Sequence
<220> FEATURE:
<223> OTHER INFORMATION: synthetic N-terminal 10xHis tag

<400> SEQUENCE: 30

His His His His His His His His His His
1 5 10

<210> SEQ ID NO 31
<211> LENGTH: 23
<212> TYPE: PRT
<213> ORGANISM: Artificial Sequence
<220> FEATURE:
<223> OTHER INFORMATION: synthetic wild type P134 TMD, wild type P134 MTD

<400> SEQUENCE: 31

Glu Ile Ala Ser Leu Cys Ala Ala Val Leu Thr Ala Leu Tyr Val Gly
1 5 10 15

Ala Gln Leu Ile Thr Leu Leu
20

<210> SEQ ID NO 32
<211> LENGTH: 23
<212> TYPE: PRT
<213> ORGANISM: Artificial Sequence
<220> FEATURE:
<223> OTHER INFORMATION: synthetic P134 TMD variant, P134 MTD variant

<400> SEQUENCE: 32

Glu Ile Ala Ser Leu Cys Ala Ala Arg Pro Thr Ala Leu Tyr Val Gly
1 5 10 15

Ala Gln Leu Ile Thr Leu Leu
20

<210> SEQ ID NO 33
<211> LENGTH: 23
<212> TYPE: PRT
<213> ORGANISM: Artificial Sequence
<220> FEATURE:
<223> OTHER INFORMATION: synthetic P134 TMD variant, P134 MTD variant

<400> SEQUENCE: 33

Glu Arg Ala Ser Leu Cys Ala Ala Arg Leu Thr Ala Leu Tyr Arg Gly
1 5 10 15

Ala Gln Leu Arg Thr Leu Leu
20

<210> SEQ ID NO 34
<211> LENGTH: 23
<212> TYPE: PRT
<213> ORGANISM: Artificial Sequence
<220> FEATURE:
<223> OTHER INFORMATION: synthetic P134 TMD variant, P134 MTD variant -continued

```
<400> SEQUENCE: 34

Glu Lys Ala Ser Leu Cys Lys Lys Arg Arg Thr Ala Leu Tyr Lys Gly
 1              5                   10                  15

Ala Gln Leu Asp Thr Leu Leu
            20


<210> SEQ ID NO 35
<211> LENGTH: 23
<212> TYPE: PRT
<213> ORGANISM: Artificial Sequence
<220> FEATURE:
<223> OTHER INFORMATION: synthetic P134 TMD variant, P134 MTD variant

<400> SEQUENCE: 35

Glu Ile Ala Ser Arg Cys Ala Ala Val Leu Thr Ala Leu Tyr Val Gly
 1              5                   10                  15

Ala Gln Leu Asn Thr Leu Lys
            20
```